: US006752992B2

(12) United States Patent
Schnepf et al.

(10) Patent No.: US 6,752,992 B2
(45) Date of Patent: *Jun. 22, 2004

(54) TOXINS ACTIVE AGAINST PESTS

(75) Inventors: H. Ernest Schnepf, San Diego, CA (US); Carol Wicker, San Diego, CA (US); Kenneth E. Narva, San Diego, CA (US); Michele Walz, Poway, CA (US); Brian A. Stockhoff, San Diego, CA (US); Judy Muller-Cohn, Del Mar, CA (US)

(73) Assignee: Mycogen Corporation, Indianapolis, IN (US)

( * ) Notice: Subject to any disclaimer, the term of this patent is extended or adjusted under 35 U.S.C. 154(b) by 39 days.

This patent is subject to a terminal disclaimer.

(21) Appl. No.: 10/099,285

(22) Filed: Mar. 15, 2002

(65) Prior Publication Data

US 2003/0105319 A1 Jun. 5, 2003

Related U.S. Application Data

(60) Division of application No. 09/002,285, filed on Dec. 31, 1997, now Pat. No. 6,369,213, which is a continuation-in-part of application No. 08/886,615, filed on Jul. 1, 1997, now abandoned, which is a continuation-in-part of application No. 08/674,002, filed on Jul. 1, 1996, now abandoned.

(51) Int. Cl.$^7$ .............................................. A61K 39/07
(52) U.S. Cl. ............................. 424/246.1; 424/185.1; 424/190.1; 424/236.1; 530/350
(58) Field of Search ....................... 530/350; 424/246.1, 424/185.1, 190.1, 236.1

(56) References Cited

U.S. PATENT DOCUMENTS

| | | | |
|---|---|---|---|
| 5,736,514 A | 4/1998 | Iizuka et al. | |
| 5,834,296 A | 11/1998 | Iizuka et al. | |
| 5,837,526 A | 11/1998 | Iizuka et al. | |
| 5,861,543 A | 1/1999 | Lambert et al. | |
| 5,885,571 A | 3/1999 | Lambert et al. | |
| 6,028,246 A | 2/2000 | Lambert et al. | |
| 6,143,550 A | 11/2000 | Lambert et al. | |
| 6,274,721 B1 | 8/2001 | Schnepf et al. | |

FOREIGN PATENT DOCUMENTS

| | | |
|---|---|---|
| EP | 0228838 | 7/1987 |
| EP | 0711834 | 5/1996 |
| JP | 8329309 | 12/1996 |
| JP | 9275497 | 10/1997 |
| WO | WO 91/16434 | 10/1991 |
| WO | WO 91/18094 | 11/1991 |
| WO | WO 93/14641 | 8/1993 |
| WO | WO 94/05771 | 3/1994 |
| WO | WO 94/24264 | 10/1994 |
| WO | WO 96/05314 | 2/1996 |
| WO | WO 96/10083 | 4/1996 |
| WO | WO 98/00546 | 1/1998 |
| WO | WO 98/26073 | 6/1998 |
| WO | WO 99/00407 | 1/1999 |
| WO | WO 99/00407 | 5/1999 |

OTHER PUBLICATIONS

Schnepf, H.E., H.R. Whiteley, "Cloning and Expression of the *Bacillus thuringiensis* Crystal Protein Gene in *Escherichia coli*," *Proc. Natl. Acad. Sci. USA*, 1981, pp. 2893–2897, vol. 78(5).

Shevelev et al., "Primary Structure of cryX, the Novel δ–endotoxin–related Gene from *Bacillus thuringiensis* spp. *galleriae*," *FEBS*, Dec. 1993, pp. 79–82, vol. 336(1).

Smulevitch, S. et al., "Nucleotide Sequence of a Novel Delta–endotoxin Gene cry1g of *Bacillus thuringiensis* ssp. *galleriae*," *FEBS Letters*, pp. 25–28, vol. 293.

Wasano et al., GenBank Accession No. AF093107, *Bacillus thuringiensis* Delta–endotoxin Gene, Partial cds. (Oct. 8, 1998).

Wasano et al., "Assignment of Delta–endotoxin Genes of the Four Lepidoptera–Specific *Bacillus thuringiensis* Strains that Produce Spherical Parasporal Inclusions," *Curr. Microbiol.* (Medline Abstract), Dec. 1998, pp. 408–411, vol. 37(6).

Wasano et al., GenBank Accession NO. AF042733, *Bacillus thuringiensis* Delta–endotoxin Gene, Partial cds. (Mar. 29, 1999).

Asano et al., "Cloning of Novel Enterotoxin Genes from *Bacillus Cereus* and *bacillus thuringlensis*," *Appl. Environ. Microbiol.*, 1997, pp. 1054–1057, vol. 63.

Beegle, C.C., "Use of Entomogenous Bacteria in Agroecosystems," *Developments in Industrial Microbiology*, 1978, pp. 61–76, vol. 22.

Carozzi et al., "Prediction of Insecticidal Activity of *Bacillus thuringiensis* Strains by Polymerase Chain Reaction Product Profiles," *Applied and Environmental Microbiology*, 1991, pp. 3057–3061, vol. 57.

(List continued on next page.)

Primary Examiner—Jennifer E. Graser
(74) Attorney, Agent, or Firm—Saliwanchik, Lloyd & Saliwanchik

(57) ABSTRACT

The subject invention concerns materials and methods useful in the control of non-mammalian pests and, particularly, plant pests. In a specific embodiment, the subject invention provides new *Bacillus thuringiensis* toxins useful for the control of lepidopterans. The subject invention further provides nucleotide sequences which encode the toxins of the subject invention. The nucleotide sequences of the subject invention can be used to transform hosts, such as plants, to express the pesticidal toxins of the subject invention. The subject invention further concerns novel nucleotide primers for the identification of genes encoding toxins active against pests. The primers are useful in PCR techniques to produce gene fragments which are characteristic of genes encoding these toxins. The primers are also useful as nucleotide probes to detect the toxin-encoding genes.

13 Claims, No Drawings

OTHER PUBLICATIONS

Couch, T.L., "Mosquito Pathogenicity of *Bacillus thuringensis* var. *israelensis," Developments in Industrial Microbiology*, 1980, pp. 61–76, vol. 22.

Feitelson, J.S. et al., "*Bacillus thuringiensis*: Insects and Beyond," *Bio./Technology*, 1992, pp. 271–275, vol. 10.

Gaertner, F., and L. Kim, "Current Applied Recombinant DNA Projects," *TIBTECH*, 1988, pp. 54–57, vol. 6(4).

Gaertner, F.H., "Cellular Delivery Systems for Insecticidal Proteins: Living and Non–Living Microorganisms," *Controlled Delivery of Crop–Protection Agents*, 1989, pp. 245–257.

Gleave et al., "Identification of an Insecticidal Crystal Protein from *Bacillus thuringiensis* DSIR517 with Significant Sequence Differences from Previously Described Toxins," *Journal of General Microbiology*, 1992, pp. 55–62, vol. 138.

Hofte et al., "Insecticidal Crystal Proteins of *Bacillus thuringiensis*," *Microbiological Reviews*, 1989, pp. 242–255, vol. 53(2).

Koziel, M.G. et al., "Transgenic Maize for the Control of European Corn Borer and other Maize Insect Pests," *Annals of the New York Academy of Sciences*, pp. 164–171, vol. 792.

Krieg, V.A. et al., "*Bacillus thuringiensis* var. *tenebrionis*: A New Pathotype Effective Against Larvae of Coleoptera," Z. ang. Ent., 1983, pp. 500–508, vol. 96.

Lambert et al., "A *Bacillus thuringiensis* Insecticidal Crystal Protein with a High Activity Against Members of the Family Noctuidae," *Applied and Environmental Microbiology*, 1996, pp. 80–86, vol. 62(1).

Midoh et al., GenBank Accession No. AB011496, *Bacillus thuringiensis* aizawai gene for Cry9 like protein, complete cds. (Feb. 5, 1999).

TOXINS ACTIVE AGAINST PESTS

CROSS-REFERENCE TO A RELATED APPLICATION

This application is a divisional of application Ser. No. 09/002,285, filed Dec. 31, 1997, now U.S. Pat. No. 6,369, 213, which is a continuation-in-part of Ser. No. 08/886,615, filed Jul. 1, 1997, now abandoned; which is a continuation-in-part of application Ser. No. 08/674,002, filed Jul. 1, 1996, now abandoned.

BACKGROUND OF THE INVENTION

The soil microbe *Bacillus thuringiensis* (*B.t.*) is a Gram-positive, spore-forming bacterium. Most strains of *B.t.* do not exhibit pesticidal activity. Some *B.t.* strains produce, and can be characterized by, parasporal crystalline protein inclusions. These "δ-endotoxins" are different from exotoxins, which have a non-specific host range. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering *B.t.* toxins to agricultural environments are under development, including the use of plants genetically engineered with *B.t.* toxin genes for insect resistance and the use of stabilized intact microbial cells as *B.t.* toxin delivery vehicles (Gaertner, F. H., L. Kim [1988] *TIBTECH* 6:S4–S7). Thus, isolated *B.t.* endotoxin genes are becoming commercially valuable.

Until the last fifteen years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis* var. *israelensis*," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) and Shevelev et al. ([1993] *FEBS Lett.* 336:79–82) describe the characterization of Cry9 toxins active against lepidopterans. Published PCT applications WO 94/05771 and WO 94/24264 also describe *B.t.* isolates active against lepidopteran pests. Gleave et al. ([1991] *JGM* 138:55–62) and Smulevitch et al. ([1991] *FEBS Lett.* 293:25–26) also describe *B.t.* toxins. A number of other classes of *B.t.* genes have now been identified.

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897.). U.S. Pat. Nos. 4,448,885 and 4,467,036 both disclose the expression of *B.t.* crystal protein in *E. coli*. U.S. Pat. Nos. 4,990,332; 5,039,523; 5,126,133; 5,164,180; and 5,169,629 are among those which disclose *B.t.* toxins having activity against lepidopterans. PCT application WO96/05314 discloses PS86W1, PS86V1, and other *B.t.* isolates active against lepidopteran pests. The PCT patent applications published as WO94/24264 and WO94/05771 describe *B.t.* isolates and toxins active against lepidopteran pests. *B.t.* proteins with activity against members of the family Noctuidae are described by Lambert et al., supra. U.S. Pat. Nos. 4,797,276 and 4,853,331 disclose *B. thuringiensis* strain *tenebrionis* which can be used to control coleopteran pests in various environments. U.S. Pat. No. 4,918,006 discloses *B.t.* toxins having activity against dipterans. U.S. Pat. Nos. 5,151,363 and 4,948,734 disclose certain isolates of *B.t.* which have activity against nematodes. Other U.S. patents which disclose activity against nematodes include U.S. Pat. Nos. 5,093,120; 5,236,843; 5,262,399; 5,270,448; 5,281,530; 5,322,932; 5,350,577; 5,426,049; and 5,439,881. As a result of extensive research and investment of resources, other patents have issued for new *B.t.* isolates and new uses of *B.t.* isolates. See Feitelson et al., supra, for a review. However, the discovery of new *B.t.* isolates and new uses of known *B.t.* isolates remains an empirical, unpredictable art.

Isolating responsible toxin genes has been a slow empirical process. Carozzi et al. (Carozzi, N. B., V. C. Kramer, G. W. Warren, S. Evola, G. Koziel (1991) *Appl. Env. Microbiol.* 57(11):3057–3061) describe methods for identifying novel *B.t.* isolates. This report does not disclose or suggest the specific primers, probes, toxins, and genes of the subject invention for lepidopteran-active toxin genes. U.S. Pat. No. 5,204,237 describes specific and universal probes for the isolation of *B.t.* toxin genes. This patent, however, does not describe the probes, primers, toxins, and genes of the subject invention.

WO 94/21795 and Estruch, J. J. et al. ([1996] *PNAS* 93:5389–5394) describe toxins obtained from Bacillus microbes. These toxins are reported to be produced during vegetative cell growth and were thus termed vegetative insecticidal proteins (VIP). These toxins were reported to be distinct from crystal-forming δ-endotoxins. Activity of these toxins against lepidopteran pests was reported.

Black cutworm (*Agrotis ipsilon* (Hufnagel); Lepidoptera: Noctuidae) is a serious pest of many crops including maize, cotton, cole crops (Brassica, broccoli, cabbages, Chinese cabbages), and turf. Secondary host plants include beetroots, Capsicum (peppers), chickpeas, faba beans, lettuces, lucerne, onions, potatoes, radishes, rape (canola), rice, soybeans, strawberries, sugarbeet, tobacco, tomatoes, and forest trees. In North America, pests of the genus Agrotis feed on clover, corn, tobacco, hemp, onion, strawberries, blackberries, raspberries, alfalfa, barley, beans, cabbage, oats, peas, potatoes, sweetpotatoes, tomato, garden flowers, grasses, luceme, maize, asparagus, grapes, almost any kind of leaf, weeds, and many other crops and garden plants. Other cutworms in the Tribe Agrotini are pests, in particular those in the genus Feltia (e.g., *F. jaculifera* (Guenée); equivalent to *ducens subgothica*) and Euxoa (e.g., *E. messoria* (Harris), *E. scandens* (Riley), *E. auxiliaris* Smith, *E. detersa* (Walker), *E. tessellata* (Harris), *E. ochrogaster* (Guenée). Host plants include various crops, including rape.

Cutworms are also pests outside North America, and the more economically significant pests attack chickpeas, wheat, vegetables, sugarbeet, luceme, maize, potatoes, turnips, rape, lettuces, strawberries, loganberries, flax, cotton, soybeans, tobacco, beetroots, Chinese cabbages, tomatoes, aubergines, sugarcane, pastures, cabbages, groundnuts, Cucurbita, turnips, sunflowers, Brassica, onions, leeks, celery, sesame, asparagus, rhubarb, chicory, greenhouse crops, and spinach. The black cutworm *A. ipsilon* occurs as a pest outside North America, including Central America, Europe, Asia, Australasia, Africa, India, Taiwan, Mexico, Egypt, and New Zealand.

Cutworms progress through several instars as larvae. Although seedling cutting by later instar larvae produces the most obvious damage and economic loss, leaf feeding commonly results in yield loss in crops such as maize. Upon reaching the fourth larval instar, larvae begin to cut plants and plant parts, especially seedlings. Because of the shift in feeding behavior, economically damaging populations may build up unexpectedly with few early warning signs. Their nocturnal habit and behavior of burrowing into the ground also makes detection problematic. Large cutworms can destroy several seedlings per day, and a heavy infestation can remove entire stands of crops.

Cultural controls for *A. ipsilon* such as peripheral weed control can help prevent heavy infestations; however, such methods are not always feasible or effective. Infestations are very sporadic, and applying an insecticide prior to planting or at planting has not been effective in the past. Some baits are available for control of cutworms in crops. To protect turfgrass such as creeping bentgrass, chemical insecticides have been employed. Use of chemical pesticides is a particular concern in turf because of the close contact the public has with treated areas (e.g., golf greens, athletic fields, parks and other recreational areas, professional landscaping, home lawns). Natural products (e.g., nematodes, azadirachtin) generally perform poorly. To date, *Bacillus thuringiensis* products have not been widely used to control black cutworm because highly effective toxins have not been available.

BRIEF SUMMARY OF THE INVENTION

The subject invention concerns materials and methods useful in the control of non-mammalian pests and, particularly, plant pests. In a specific embodiment, the subject invention provides new toxins useful for the control of lepidopterans. In a particularly preferred embodiment, the toxins of the subject invention are used to control black cutworm. The subject invention further provides nucleotide sequences which encode the lepidopteran-active toxins of the subject invention. The subject invention further provides nucleotide sequences and methods useful in the identification and characterization of genes which encode pesticidal toxins. The subject invention further provides new *Bacillus thuringiensis* isolates having pesticidal activities.

In one embodiment, the subject invention concerns unique nucleotide sequences which are useful as primers in PCR techniques. The primers produce characteristic gene fragments which can be used in the identification and isolation of specific toxin genes. The nucleotide sequences of the subject invention encode toxins which are distinct from previously-described δ-endotoxins.

In one embodiment of the subject invention, *B.t.* isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

A further aspect of the subject invention is the use of the disclosed nucleotide sequences as probes to detect, identify, and characterize genes encoding *B.t.* toxins which are active against lepidopterans.

Further aspects of the subject invention include the genes and isolates identified using the methods and nucleotide sequences disclosed herein. The genes thus identified encode toxins active against lepidopterans. Similarly, the isolates will have activity against these pests.

New pesticidal *B.t.* isolates of the subject invention include PS31G1, PS185U2, PS11B, PS218G2, PS213E5, PS28C, PS86BB1, PS89J3, PS94R1, PS27J2, PS101DD, and PS202S.

As described herein, the toxins useful according to the subject invention may be chimeric toxins produced by combining portions of multiple toxins.

In a preferred embodiment, the subject invention concerns plants cells transformed with at least one polynucleotide sequence of the subject invention such that the transformed plant cells express pesticidal toxins in tissues consumed by the target pests. Such transformation of plants can be accomplished using techniques well known to those skilled in the art and would typically involve modification of the gene to optimize expression of the toxin in plants.

Alternatively, the *B.t.* isolates of the subject invention, or recombinant microbes expressing the toxins described herein, can be used to control pests. In this regard, the invention includes the treatment of substantially intact *B.t.* cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer useful according to the subject invention.

SEQ ID NO. 2 is a reverse primer useful according to the subject invention.

SEQ ID NO. 3 is a forward primer useful according to the subject invention.

SEQ ID NO. 4 is a reverse primer useful according to the subject invention.

SEQ ID NO. 5 is a forward primer useful according to the subject invention.

SEQ ID NO. 6 is a reverse primer useful according to the subject invention.

SEQ ID NO. 7 is an amino acid sequence of the toxin designated 11B1AR.

SEQ ID NO. 8 is a nucleotide sequence encoding an amino acid sequence of toxin 11B1AR (SEQ ID NO. 7).

SEQ ID NO. 9 is an amino acid sequence of the toxin designated 11B1AR.

SEQ ID NO. 10 is a nucleotide sequence encoding an amino acid sequence of toxin 11B1BR (SEQ ID NO. 9).

SEQ ID NO. 11 is an amino acid sequence of the toxin designated 1291A.

SEQ ID NO. 12 is a nucleotide sequence encoding an amino acid sequence of toxin 1291A (SEQ ID NO. 11).

SEQ ID NO. 13 is an amino acid sequence of the toxin designated 1292A.

SEQ ID NO. 14 is a nucleotide sequence encoding an amino acid sequence of toxin 1292A (SEQ ID NO. 13).

SEQ ID NO. 15 is an amino acid sequence of the toxin designated 1292B.

SEQ ID NO. 16 is a nucleotide sequence encoding an amino acid sequence of toxin 1292B (SEQ ID NO. 15).

SEQ ID NO. 17 is an amino acid sequence of the toxin designated 31GA.

SEQ ID NO. 18 is a nucleotide sequence encoding an amino acid sequence of toxin 31GA (SEQ ID NO. 17).

SEQ ID NO. 19 is an amino acid sequence of the toxin designated 31GBR.

SEQ ID NO. 20 is a nucleotide sequence encoding an amino acid sequence of toxin 31GBR (SEQ ID NO. 19).

SEQ ID NO. 21 is an amino acid sequence of the toxin designated 85N1R identified by the method of the subject invention.

SEQ ID NO. 22 is a nucleotide sequence encoding an amino acid sequence of toxin 85N1R (SEQ ID NO. 21).

SEQ ID NO. 23 is an amino acid sequence of the toxin designated 85N2.

SEQ ID NO. 24 is a nucleotide sequence encoding an amino acid sequence of toxin 85N2 (SEQ ID NO. 23).

SEQ ID NO. 25 is an amino acid sequence of the toxin designated 85N3.

SEQ ID NO. 26 is a nucleotide sequence encoding an amino acid sequence of toxin 85N3 (SEQ ID NO. 25).

SEQ ID NO. 27 is an amino acid sequence of the toxin designated 86V1C1.

SEQ ID NO. 28 is a nucleotide sequence encoding an amino acid sequence of toxin 86V1C1 (SEQ ID NO. 27).

SEQ ID NO. 29 is an amino acid sequence of the toxin designated 86V1C2.

SEQ ID NO. 30 is a nucleotide sequence encoding an amino acid sequence of toxin 86V1C2 (SEQ ID NO. 29).

SEQ ID NO. 31 is an amino acid sequence of the toxin designated 86V1C3R.

SEQ ID NO. 32 is a nucleotide sequence encoding an amino acid sequence of toxin 86V1C3R (SEQ ID NO. 31).

SEQ ID NO. 33 is an amino acid sequence of the toxin designated F525A.

SEQ ID NO. 34 is a nucleotide sequence encoding an amino acid sequence of toxin F252A (SEQ ID NO. 33).

SEQ ID NO. 35 is an amino acid sequence of the toxin designated F525B.

SEQ ID NO. 36 is a nucleotide sequence encoding an amino acid sequence of toxin F525B (SEQ ID NO. 35).

SEQ ID NO. 37 is an amino acid sequence of the toxin designated F525C.

SEQ ID NO. 38 is a nucleotide sequence encoding an amino acid sequence of toxin F525C (SEQ ID NO. 37).

SEQ ID NO. 39 is an amino acid sequence of the toxin designated F573A.

SEQ ID NO. 40 is a nucleotide sequence encoding an amino acid sequence of toxin F573A (SEQ ID NO. 39).

SEQ ID NO. 41 is an amino acid sequence of the toxin designated F573B.

SEQ ID NO. 42 is a nucleotide sequence encoding an amino acid sequence of toxin F573B (SEQ ID NO. 41).

SEQ ID NO. 43 is an amino acid sequence of the toxin designated F573C.

SEQ ID NO. 44 is a nucleotide sequence encoding an amino acid sequence of toxin F573C (SEQ ID NO. 43).

SEQ ID NO. 45 is an amino acid sequence of the toxin designated FBB1A.

SEQ ID NO. 46is a nucleotide sequence encoding an amino acid sequence of toxin FBB1A (SEQ ID NO. 45).

SEQ ID NO. 47 is an amino acid sequence of the, toxin designated FBB1BR.

SEQ ID NO. 48 is a nucleotide sequence encoding an amino acid sequence of toxin FBB1BR (SEQ ID NO. 47).

SEQ ID NO. 49 is an amino acid sequence of the toxin designated FBB1C.

SEQ ID NO. 50 is a nucleotide sequence encoding an amino acid sequence of toxin FBB1C (SEQ ID NO. 49).

SEQ ID NO. 51 is an amino acid sequence of the toxin designated FBB1D.

SEQ ID NO. 52 is a nucleotide sequence encoding an amino acid sequence of toxin FBB1D (SEQ ID NO. 51).

SEQ ID NO. 53 is an amino acid sequence of the toxin designated J31AR.

SEQ ID NO. 54 is a nucleotide sequence encoding an amino acid sequence of toxin J31AR (SEQ ID NO. 53).

SEQ ID NO. 55 is an amino acid sequence of the toxin designated J32AR.

SEQ ID NO. 56 is a nucleotide sequence encoding an amino acid sequence of toxin J32AR (SEQ ID NO. 55).

SEQ ID NO. 57 is an amino acid sequence of the toxin designated W1FAR.

SEQ ID NO. 58 is a nucleotide sequence encoding an amino acid sequence of toxin W1FAR (SEQ ID NO. 57).

SEQ ID NO. 59 is an amino acid sequence of the toxin designated W1FBR.

SEQ ID NO. 60 is a nucleotide sequence encoding an amino acid sequence of toxin W1FBR (SEQ ID NO. 59).

SEQ ID NO. 61 is an amino acid sequence of the toxin designated W1FC.

SEQ ID NO. 62 is a nucleotide sequence encoding an amino acid sequence of toxin W1FC (SEQ ID NO. 61).

SEQ ID NO. 63 is an oligonucleotide useful as a PCR primer or hybridization probe according to the subject invention.

SEQ ID NO. 64 is an oligonucleotide useful as a PCR primer or hybridization probe according to the subject invention.

SEQ ID NO. 65 is an oligonucleotide useful as a PCR primer or hybridization probe according to the subject invention.

SEQ ID NO. 66 is an oligonucleotide useful as a PCR primer or hybridization probe according to the subject invention.

SEQ ID NO. 67 is an oligonucleotide useful as a PCR primer or hybridization probe according to the subject invention.

SEQ ID NO. 68 is an oligonucleotide useful as a PCR primer or hybridization probe according to the subject invention.

SEQ ID NO. 69 is an oligonucleotide useful as a PCR primer or hybridization probe according to the subject invention.

SEQ ID NO. 70 is an amino acid sequence of the toxin designated 86BB1(a).

SEQ ID NO. 71 is a nucleotide sequence encoding an amino acid sequence of toxin 86BB1(a).

SEQ ID NO. 72 is an amino acid sequence of the toxin designated 86BB1(b).

SEQ ID NO. 73 is a nucleotide sequence encoding an amino acid sequence of toxin 86BB1(b).

SEQ ID NO. 74 is an amino acid sequence of the toxin designated 31G1(a).

SEQ ID NO. 75 is a nucleotide sequence encoding an amino acid sequence of toxin 31G1(a).

SEQ ID NO. 76 is an amino acid sequence of the toxin designated 129HD chimeric.

SEQ ID NO. 77 is a nucleotide sequence encoding an amino acid sequence of toxin 129HD chimeric.

SEQ ID NO. 78 is an amino acid sequence of the toxin designated 11B(a).

SEQ ID NO. 79 is a nucleotide sequence encoding an amino acid sequence of toxin 11B(a).

SEQ ID NO. 80 is an amino acid sequence of the toxin designated 31G1(b).

SEQ ID NO. 81 is a nucleotide sequence encoding an amino acid sequence of toxin 3G1(b).

SEQ ID NO. 82 is an amino acid sequence of the toxin designated 86BB1(c).

SEQ ID NO. 83 is a nucleotide sequence encoding an amino acid sequence of toxin 86BB1(c).

SEQ ID NO. 84 is an amino acid sequence of the toxin designated 86V1(a).

SEQ ID NO. 85 is a nucleotide sequence encoding an amino acid sequence of toxin 86V1(a).

SEQ ID NO. 86 is an amino acid sequence of the toxin designated 86W1(a).

SEQ ID NO. 87 is a nucleotide sequence encoding an amino acid sequence of toxin 86W1(a).

SEQ ID NO. 88 is a partial amino acid sequence of the toxin designated 94R1(a).

SEQ ID NO. 89 is a partial nucleotide sequence encoding an amino acid sequence of toxin 94R1(a).

SEQ ID NO. 90 is an amino acid sequence of the toxin designated 185U2(a).

SEQ ID NO. 91 is a nucleotide sequence encoding an amino acid sequence of toxin 185U2(a).

SEQ ID NO. 92 is an amino acid sequence of the toxin designated 202S(a).

SEQ ID NO. 93 is a nucleotide sequence encoding an amino acid sequence of toxin 202S(a).

SEQ ID NO. 94 is an amino acid sequence of the toxin designated 213E5(a).

SEQ ID NO. 95 is a nucleotide sequence encoding an amino acid sequence of toxin 213E5(a).

SEQ ID NO. 96 is an amino acid sequence of the toxin designated 218G2(a).

SEQ ID NO. 97 is a nucleotide sequence encoding an amino acid sequence of toxin 218G2(a).

SEQ ID NO. 98 is an amino acid sequence of the toxin designated 29HD(a).

SEQ ID NO. 99 is a nucleotide sequence encoding an amino acid sequence of toxin 29HD(a).

SEQ ID NO. 100 is an amino acid sequence of the toxin designated 110HD(a).

SEQ ID NO. 101 is a nucleotide sequence encoding an amino acid sequence of toxin 110HD(a).

SEQ ID NO. 102 is an amino acid sequence of the toxin designated 129HD(b).

SEQ ID NO. 103 is a nucleotide sequence encoding an amino acid sequence of toxin 129HD(b).

SEQ ID NO. 104 is a partial amino acid sequence of the toxin designated 573HD(a).

SEQ ID NO. 105 is a partial nucleotide sequence encoding an amino acid sequence of toxin 573HD(a).

DETAILED DISCLOSURE OF THE INVENTION

The subject invention concerns materials and methods for the control of non-mammalian pests. In specific embodiments, the subject invention pertains to new *Bacillus thuringiensis* isolates and toxins which have activity against lepidopterans. In a particularly preferred embodiment, the toxins and methodologies described herein can be used to control black cutworm. The subject invention further concerns novel genes which encode pesticidal toxins and novel methods for identifying and characterizing *B.t.* genes which encode toxins with useful properties. The subject invention concerns not only the polynucleotide sequences which encode these toxins, but also the use of these polynucleotide sequences to produce recombinant hosts which express the toxins.

Certain proteins of the subject invention are distinct from the crystal or "Cry" proteins which have previously been isolated from *Bacillus thuringiensis*.

A further aspect of the subject invention concerns novel isolates and the toxins and genes obtainable from these isolates. The novel *B.t.* isolates of the subject invention have been designated PS31G1, PS185U2, PS11B, PS218G2, PS213E5, PS28C, PS86BB1, PS89J3, PS94R1, PS202S, PS101DD, and PS27J2.

The new toxins and polynucleotide sequences provided here are defined according to several parameters. One critical characteristic of the toxins described herein is pesticidal activity. In a specific embodiment, these toxins have activity against lepidopteran pests. The toxins and genes of the subject invention can be further defined by their amino acid and nucleotide sequences. The sequences of the molecules can be defined in terms of homology to certain exemplified sequences as well as in terms of the ability to hybridize with, or be amplified by, certain exemplified probes and primers. The toxins provided herein can also be identified based on their immunoreactivity with certain antibodies.

Methods have been developed for making useful chimeric toxins by combining portions of *B.t.* crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J. Biol. Chem.* 266:17954–17958; Schnepf, H. E., K. Tomczak, J. P. Ortega, H. R. Whiteley (1990) *J. Biol. Chem.* 265:20923–20930; Honee, G., D. Convents, J. Van Rie, S. Jansens, M. Peferoen, B. Visser(1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Stickema (1994) *Biotechnology* 12:915–918. A number of other methods are known in the art by which such chimeric DNAs can be made. The subject invention is meant to include chimeric proteins that utilize the novel sequences identified in the subject application.

With the teachings provided herein, one skilled in the art could readily produce and use the various toxins and polynucleotide sequences described herein.

*B.t.* isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the *B.t.* strains are as follows:

| Culture | Repository No. | Deposit Date |
|---|---|---|
| B.t. PS11B (MT274) | NRRL B-21556 | Apr. 18, 1996 |
| B.t. PS86BB1 (MT275) | NRRL B-21557 | Apr. 18, 1996 |
| B.t. PS86V1 (MT276) | NRRL B-21558 | Apr. 18, 1996 |
| B.t. PS86W1 (MT277) | NRRL B-21559 | Apr. 18, 1996 |
| B.t. PS31G1 (MT278) | NRRL B-21560 | Apr. 18, 1996 |
| B.t. PS89J3 (MT279) | NRRL B-21561 | Apr. 18, 1996 |
| B.t. PS185U2 (MT280) | NRRL B-21562 | Apr. 18, 1996 |
| B.t PS27J2 | NRRL B-21799 | Jul. 1, 1997 |
| B.t. PS28C | NRRL B-21800 | Jul. 1, 1997 |
| B.t. PS94R1 | NRRL B-21801 | Jul. 1, 1997 |
| B.t. PS101DD | NRRL B-21802 | Jul. 1, 1997 |
| B.t. PS202S | NRRL B-21803N | Oct. 17, 1997 |
| B.t. PS213E5 | NRRL B-21804 | Jul. 1, 1997 |
| B.t. PS218G2 | NRRL B-21805 | Jul. 1, 1997 |
| E. coli NM522 (MR 922) (pMYC2451) | NRRL B-21794 | Jun. 27, 1997 |
| E. coli NM522 (MR 923) (pMYC2453) | NRRL B-21795 | Jun. 27, 1997 |
| E. coli NM522 (MR 924) (pMYC2454) | NRRL B-21796 | Jun. 27, 1997 |

Cultures which have been deposited for the purposes of this patent application were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, ie., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Following is a table which provides characteristics of certain isolates useful according to the subject invention.

TABLE 1

Description of B.t. strains toxic to lepidopterans

| Culture | Crystal Description | Approx. MW (kDa) | Serotype |
|---|---|---|---|
| PS185U2 | small bipyramid | 130 kDa doublet, 70 kDa | ND |
| PS11B | bipyramid tort | 130 kDa, 70 kDa | ND |
| PS218G2 | amorphic | 135 kDa, 127 kDa | ND |
| PS213E5 | amorphic | 130 kDa | ND |
| PS86W1 | multiple amorphic | 130 kDa doublet | 5a5b gatteriae |
| PS28C | amorphic | 130 kDa triplet | 5a5b gatteriae |
| PS86BB1 | BP without | 130 kDa doublet | 5a5b gatteriae |
| PS89J3 | spherical/amorphic | 130 kDa doublet | ND |
| PS86V1 | BP | 130 kDa doublet | ND |
| PS94R1 | BP and amorphic | 130 kDa doublet | ND |
| HD525 | BP and amorphic | 130 kDa | not motile |
| HD573 | multiple amorphic | 135 kDa, 79 kDa doublet, 72 kDa | not motile |
| PS27J2 | lemon-shaped | 130 kDa 50 kDa | 4 (sotto or kenyae) |

ND = not determined

In one embodiment, the subject invention concerns materials and methods including nucleotide primers and probes for isolating and identifying *Bacillus thuringiensis* (*B.t.*) genes encoding protein toxins which are active against lepidopteran pests. The nucleotide sequences described herein can also be used to identify new pesticidal *B.t.* isolates. The invention further concerns the genes, isolates, and toxins identified using the methods and materials disclosed herein.

Genes and toxins.

The genes and toxins useful according to the subject invention include not only the full length sequences but also fragments of these sequences, variants, mutants, and fusion proteins which retain the characteristic pesticidal activity of the toxins specifically exemplified herein. Chimeric genes and toxins, produced by combining portions from more than one *B.t.* toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from *B.t.* isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other *B.t.* toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. Probes provide a rapid method for identifying toxin-encoding genes of the subject invention. The nucleotide segments which are used as probes according to the invention can be synthesized using a DNA synthesizer and standard procedures.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid identity will typically be greater than 60%, preferably be greater than 75%, more preferably greater than 80%, more preferably greater than 90%, and can be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

As used herein, reference to "isolated" polynucleotides and/or "purified" toxins refers to these molecules when they are not associated with the other molecules with which they would be found in nature. Thus, "purified" toxins would include, for example, the subject toxins expressed in plants. Reference to "isolated and purified" signifies the involvement of the "hand of man" as described herein. Chimeric toxins and genes also involve the "hand of man."

Recombinant hosts.

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a *B.t.* gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Control of lepidopterans, including black cutworm, using the isolates, toxins, and genes of the subject invention can be accomplished by a variety of methods known to those skilled in the art. These methods include, for example, the application of *B.t.* isolates to the pests (or their location), the application of recombinant microbes to the pests (or their locations), and the transformation of plants with genes which encode the pesticidal toxins of the subject invention. Recombinant microbes may be, for example, a *B.t., E. coli,* or Pseudomonas. Transformations can be made by those skilled in the art using standard techniques. Materials necessary for these transformations are disclosed herein or are otherwise readily available to the skilled artisan.

Synthetic genes which are functionally equivalent to the toxins of the subject invention can also be used to transform hosts. Methods for the production of synthetic genes can be found in, for example, U.S. Pat. No. 5,380,831.

Treatment of cells.

As mentioned above, *B.t.* or recombinant cells expressing a *B.t.* toxin can be treated to prolong the toxin activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques,* W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells.

The cellular host containing the *B.t.* insecticidal gene maybe grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Methods and formulations for control of pests.

Control of lepidopterans using the isolates, toxins, and genes of the subject invention can be accomplished by a variety of methods known to those skilled in the art. These methods include, for example, the application of *B.t.* isolates to the pests (or their location), the application of recombinant microbes to the pests (or their locations), and the transformation of plants with genes which encode the pesticidal toxins of the subject invention. Recombinant microbes may be, for example, a *B.t., E. coli,* or Pseudomonas. Transformations can be made by those skilled in the art using standard techniques. Materials necessary for these transformations are disclosed herein or are otherwise readily available to the skilled artisan.

Formulated bait granules containing an attractant and spores and crystals of the *B.t.* isolates, or recombinant microbes comprising the genes obtainable from the *B.t.* isolates disclosed herein, can be applied to the soil. Formulated product can also be applied as a seed-coating or root treatment or total plant treatment at later stages of the crop cycle. Plant and soil treatments of *B.t.* cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and maybe 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants.

Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (–). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Polynucleotide Drobes.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The probes may be RNA or DNA. The probe will normally have at least about 10 bases, more usually at least about 18 bases, and may have up to about 50 bases or more, usually not having more than about 200 bases if the probe is made synthetically. However, longer probes can readily be utilized, and such probes can be, for example, several kilobases in length. The probe sequence is designed to be at least substantially complementary to a gene encoding a toxin of interest. The probe need not have perfect complementarity to the sequence to which it hybridizes. The probes may be labelled utilizing techniques which are well known to those skilled in this art.

One approach for the use of the subject invention as probes entails first identifying by Southern blot analysis of a gene bank of the *B.t.* isolate all DNA segments homologous with the disclosed nucleotide sequences. Thus, it is possible, without the aid of biological analysis, to know in advance the probable activity of many new *B.t.* isolates, and of the individual endotoxin gene products expressed by a given *B.t.* isolate. Such a probe analysis provides a rapid method for identifying potentially commercially valuable insecticidal endotoxin genes within the multifarious subspecies of *B.t.*

One hybridization procedure useful according to the subject invention typically includes the initial steps of isolating the DNA sample of interest and purifying it chemically.

Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) *DNA Probes,* Stockton Press, New York, N.Y., pp. 169–170.

As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis, T., E. F. Fritsch, J. Sambrook [1982] *Molecular Cloning: A Laboratory Manual,* Cold Spring Harbor Laboratory, Cold Spring Harbor, N.Y.). In general, hybridization and subsequent washes were carried out under stringent conditions that allowed for detection of target sequences with homology to the exemplified toxin genes. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu, L. Grossman and K. Moldave [eds.] Academic Press, New York 100:266–285).

$$Tm=81.5°\ C.+16.6\ Log[Na+]+0.41(\%G+C)-0.61(\%formamide)-600/length\ of\ duplex\ in\ base\ pairs.$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm(°C.)=2(number\ T/A\ base\ pairs)+4(number\ G/C\ base\ pairs)$$

(Suggs, S. V., T. Miyake, E. H. Kawashime, M. J. Johnson, K. Itakura, and R. B. Wallace [1981] *ICN-UCLA Symp. Dev. Biol. Using Purified Genes,* D. D. Brown [ed.], Academic Press, New York, 23:683–693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

PCR technology.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350–1354.). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus,* the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

Following are examples which illustrate procedures for practicing the invention. These examples should not be construed as limiting. All percentages are by weight and all solvent mixture proportions are by volume unless otherwise noted.

EXAMPLE 1

Culturing of *B.t.* Isolates Useful According to the Invention

A subculture of *B.t.* isolates, or mutants thereof, can be used to inoculate the following peptone, glucose, salts medium:

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

Alternatively, a subculture of *B.t.* isolates, or mutants thereof, can be used to inoculate the following medium, known as TB broth:

| | |
|---|---|
| Tryptone | 12 g/l |
| Yeast Extract | 24 g/l |
| Glycerol | 4 g/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24–36 hours.

The above procedure can be readily scaled up to large fermentors by procedures well known in the art.

The *B.t.* obtained in the above fermentation, can be isolated by procedures well known in the art. A frequently-used procedure is to subject the harvested fermentation broth to separation techniques, e.g., centrifugation. In a specific embodiment, B.t. proteins useful according the present invention can be obtained from the supernatant. The culture supernatant containing the active protein(s) was used in bioassays as discussed below.

EXAMPLE 2

Identification of Genes Encoding Novel Lepidopteran-Active *Bacillus thuringiensis* Toxins Two primer pairs useful for the identification and classification of novel toxin genes by PCR amplification of polymorphic DNA fragments near the 3' ends of B.t. toxin genes were designed. These oligonucleotide primers allow the discrimination of genes encoding toxins in the Cry7, Cry8, or Cry9 subfamilies from genes for the more common lepidopteran-active toxins in the CryI subfamily based on size differences for the amplified DNA. The sequences of these primers are:

| | |
|---|---|
| Forward 1 5' CGTGGCTATATCCTTCGTGTY AC 3' | (SEQ ID NO. 1) |
| Reverse 1 5' ACRATRAATGTTCCTTCYGTT TC 3' | (SEQ ID NO. 2) |
| Forward 2 5' GGATATGTMTTACGTGTAAC WGC 3' | (SEQ ID NO. 3) |
| Reverse 2 5' CTACACTTTCTATRTTGAATR YACCTTC 3' | (SEQ ID NO. 4) |

Standard PCR amplification (Perkin Elmer, Foster City, Calif.) using primer pair 1 (SEQ ID NOS. 1 and 2) of the subject invention yields DNA fragments approximately 415–440 base pairs in length from B.t. toxin genes related to the cry1 subfamily.

PCR amplification using primer pair 2 (SEQ ID NOS. 3 and 4) according to the subject invention yields DNA fragments approximately 230–290 base pairs in length from cry7, cry8, or cry9 subfamily toxin genes.

These primers can be used according to the subject invention to identify genes encoding novel toxins. Crude DNA templates for PCR were prepared from B.t. strains. A loopful of cells was scraped from an overnight plate culture of *Bacillus thuringiensis* and resuspended in 300 ml TE buffer (10 mM Tris-Cl, 1 mM EDTA, pH 8.0). Proteinase K was added to 0.1 mg/ml and the cell suspension was heated to 55° C. for 15 minutes. The suspension was then boiled for 15 minutes. Cellular debris was pelleted in a microfuge and the supernatant containing the DNA was transferred to a clean tube.

PCR was carried out using the primer pair consisting of the Forward 2 (SEQ ID NO. 3) and Reverse 2 (SEQ ID NO. 4) oligonucleotides described above. Strains were identified that contained genes characterized by amplification of DNA fragments approximately 230–290 bp in length. Spore-crystal preparations from these strains were subsequently tested for bioactivity against *Agrotis ipsilon* and additional lepidopteran targets.

PS185U2 was examined using both primer pairs 1 and 2 (SEQ ID NOS. 1 and 2 and SEQ ID NOS. 3 and 4, respectively). In this strain, primer pair 1 (SEQ ID NOS. 1 and 2) yielded a DNA band of the size expected for toxin genes related to the cry1 subfamily.

EXAMPLE 3

Restriction Fragment Length Polymorphism (RFLP) Analysis of *Bacillus thuringiensis* Toxin Genes Present in Lepidopteran-Active Strains Total cellular DNA was prepared from *Bacillus thuringiensis* (B.t.) strains grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 g/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

Two types of PCR-amplified, $^{32}$P-labeled DNA probes were used in standard Southern hybridizations of total cellular B.t. DNA to characterize toxin genes by RFLP. The first probe (A) was a DNA fragment amplified using the following primers:

| | |
|---|---|
| Forward 3: 5' CCAGWTTTAYAGGAGG 3' | (SEQ ID NO. 5) |
| Reverse 3: 5' GTAAACAAGCTCGCCACCGC 3' | (SEQ ID NO. 6) |

The second probe (B) was either the 230–290 bp or 415–440 bp DNA fragment amplified with the primers described in the previous example.

Hybridization of immobilized DNA on Southern blots with the aforementioned $^{32}$P-labeled probes was performed by standard methods (Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under moderate stringency. For double-stranded DNA gene probes, hybridization was carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] In *Methods in Enzymology*, R. Wu, L. Grossman and K. Moldave (eds.), Academic Press, New York. 100:266–285):

$Tm=81.5°$ C.$+16.6$ Log[Na+]$+0.41(\%G+C)-0.61(\%$formamide$)-600$/length of duplex in base pairs.

Washes were typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS (moderate stringency wash).

RFLP data was obtained for the ten strains most active on *Agrotis ipsilon* (Tables 3 and 4). The hybridizing DNA bands described here contain all or part of the novel toxin genes under investigation.

TABLE 3

RFLP data for *Bacillus thuringiensis* strains using probe A

| | Approximate size (base pairs) *Bacillus thuringiensis* strain | | | | | | | | | |
|---|---|---|---|---|---|---|---|---|---|---|
| Digest | PS185U2 | PS89J3 | PS11B | HD129 | PS86BB1 | PS86W1 | PS86V1 | PS31G1 | HD573 | HD525 |
| EcoRI | 8410 | 11837 | 11168 | 11132 | 8267 | 8718 | 10356 | 11687 | 9816 | 9570 |
| | 3631 | 9769 | 7347 | 5876 | 5585 | 5159 | 7105 | 7419 | 5908 | 5760 |
| | 1900 | 7225 | | 3684 | | | | 3659 | 3838 | 3742 |
| | 925 | 4921 | | 628 | | | | 1716 | | |
| | 661 | | | | | | | 846 | | |
| | | | | | | | | 498 | | |
| Sac1 | | 8997 | | 6326 | 10057 | 9165 | 12170 | 10564 | 6708 | 6216 |
| | | 5645 | | | 5450 | 5993 | 6046 | 6063 | 5204 | 5074 |
| | | 3741 | | | | 4120 | | 4710 | | |
| | | 2548 | | | | 3291 | | | | |
| HinDIII | 5331 | 11837 | 5603 | 11409 | 8682 | 10384 | 10356 | 5620 | | |
| | 3997 | 9505 | | 5458 | 5724 | 5993 | 7105 | 2570 | | |
| | 1993 | 6129 | | 1945 | 3868 | | 3436 | 936 | | |
| | | | | 1190 | 3027 | | | | | |
| KpnI | | 12852 | | 4596 | | 9878 | | 4258 | | |
| | | 5802 | | | | 8938 | | | | |
| | | | | | | 6300 | | | | |
| Xbal | 2658 | | 1596 | 5876 | | | | 9312 | | |
| | 763 | | | 3870 | | | | 5911 | | |
| | 630 | | | 3258 | | | | 2827 | | |
| | | | | 2093 | | | | 2636 | | |
| | | | | 1521 | | | | 1760 | | |
| | | | | | | | | 1010 | | |
| | | | | | | | | 625 | | |
| | | | | | | | | 359 | | |

TABLE 4

RFLP data for *Bacillus thuringiensis* strains using probe B

| | Approximate size (base pairs) *Bacillus thuringiensis* Strain | | | | | | | | | |
|---|---|---|---|---|---|---|---|---|---|---|
| Digest | PS185U2 | PS89J3 | PS11B | HD129 | PS86BB1 | PS86W1 | PS86V1 | PS31G1 | HD573 | HD525 |
| EcoRI | 10493 | 10838 | 9874 | 4922 | 8286 | 7334 | 9791 | 8603 | 9741 | 9741 |
| | 4387 | 6217 | 7347 | 3048 | 5567 | 6638 | 6412 | 4228 | 6146 | 5840 |
| | | | 3686 | | | | | | 3685 | 3878 |
| SacI | | 10252 | | 5177 | 9619 | 11487 | 11475 | 10646 | 5840 | 5840 |
| | | 6217 | | | 5297 | 6638 | 6081 | 6789 | | |
| | | | | | | | | 5486 | | |
| HinDIII | 7197 | 5880 | 7718 | 5177 | 5567 | 6316 | 6412 | 6475 | 5840 | 5840 |
| | 5553 | 3985 | 6033 | 4022 | 3740 | 4239 | 4199 | 3183 | 4522 | 4522 |
| | | 2700 | 2882 | | 2513 | 2845 | 3057 | | | |
| KpnI | 3548 | 12113 | 1446 | 10491 | 10624 | 12074 | 12756 | 1528 | 10791 | 10791 |
| | | 7345 | 1076 | | 7884 | 8953 | 9286 | | 4082 | 4296 |
| | | | | | | | | | 1994 | 2099 |
| Xbal | | 5262 | | 5048 | 4563 | 5716 | 4921 | 9684 | 5549 | 5840 |
| | | 3985 | | 3048 | 3386 | 4455 | 3583 | 6630 | 3501 | 3685 |

EXAMPLE 4

DNA Sequencing of Toxin Genes

PCR-amplified segments of toxin genes present in *B.t.* strains active on *Agrotis epsilon* were sequenced. To accomplish this, amplified DNA fragments obtained using primers Forward 3 (SEQ ID NO. 5) and Reverse 3 (SEQ ID NO. 6) were first cloned into the PCR DNA TA-cloning plasmid vector, pCRII, as described by the supplier (Invitrogen, San Diego, Calif.). Several individual pCRII clones from the mixture of amplified DNA fragments from each *B.t.* strain were chosen for sequencing. Colonies were lysed by boiling to release crude plasmid DNA. DNA templates for automated sequencing were amplified by PCR using vector-specific primers flanking the plasmid multiple cloning sites. These DNA templates were sequenced using Applied Biosystems (Foster City, Calif.) automated sequencing methodologies. Toxin gene sequences and their corresponding nucleotide sequences, described below (SEQ ID NO. 7 through SEQ ID NO. 62), were identified by this method. These sequences are listed in Table 5. The polypeptide sequences deduced from these nucleotide sequences are also shown.

From these partial gene sequences, seven oligonucleotides useful as PCR primers or hybridization probes were designed. The sequences of these oligonucleotides are the following:

5'GTTCATTGGTATAAGAGTTGGTG 3' (SEQ ID NO. 63)

5'CCACTGCAAGTCCGGACCAAATTCG 3' (SEQ ID NO. 64)

5'GAATATATTCCCGTCYATCTCTGG 3'   (SEQ ID NO. 65)

5'GCACGAATTACTGTAGCGATAGG 3'   (SEQ ID NO. 66)

5'GCTGGTAACTTTGGAGATATGCGTG 3'   (SEQ ID NO. 67)

5'GATTTCTTTGTAACACGTGGAGG 3'   (SEQ ID NO. 68)

5'CACTACTAATCAGAGCGATCTG 3'   (SEQ ID NO. 69)

Specific gene toxin sequences and the oligonucleotide probes that enable identification of these genes by hybridization, or by PCR in combination with the Reverse 3 primer described above, are listed in Table 5.

TABLE 5

Sequence ID reference numbers

| Strain | Toxin | Peptide | Nucleotide | Probe used |
|---|---|---|---|---|
| PS11B | 11B1AR | SEQ ID NO. 7 | SEQ ID NO. 8 | |
| | 11B1BR | SEQ ID NO. 9 | SEQ ID NO. 10 | SEQ ID NO. 65 |
| HD129 | 1291A | SEQ ID NO. 11 | SEQ ID NO. 12 | SEQ ID NO. 63 |
| | 1292A | SEQ ID NO. 13 | SEQ ID NO. 14 | SEQ ID NO. 64 |
| | 1292B | SEQ ID NO. 15 | SEQ ID NO. 16 | |
| PS31G1 | 31GA | SEQ ID NO. 17 | SEQ ID NO. 18 | SEQ ID NO. 65 |
| | 31GBR | SEQ ID NO. 19 | SEQ ID NO. 20 | |
| PS185U2 | 85N1R | SEQ ID NO. 21 | SEQ ID NO. 22 | |
| | 85N2 | SEQ ID NO. 23 | SEQ ID NO. 24 | |
| | 85N3 | SEQ ID NO. 25 | SEQ ID NO. 26 | SEQ ID NO. 66 |
| PS86V1 | 86V1C1 | SEQ ID NO. 27 | SEQ ID NO. 28 | SEQ ID NO. 68 |
| | 86V1C2 | SEQ ID NO. 29 | SEQ ID NO. 30 | SEQ ID NO. 64 |
| | 86V1C3R | SEQ ID NO. 31 | SEQ ID NO. 32 | SEQ ID NO. 69 |
| HD525 | F525A | SEQ ID NO. 33 | SEQ ID NO. 34 | SEQ ID NO. 64 |
| | F525B | SEQ ID NO. 35 | SEQ ID NO. 36 | SEQ ID NO. 63 |
| | F525C | SEQ ID NO. 37 | SEQ ID NO. 38 | |
| HD573 | F573A | SEQ ID NO. 39 | SEQ ID NO. 40 | SEQ ID NO. 63 |
| | F573B | SEQ ID NO. 41 | SEQ ID NO. 42 | SEQ ID NO. 67 |
| | F573C | SEQ ID NO. 43 | SEQ ID NO. 44 | SEQ ID NO. 64 |
| PS86BB1 | FBB1A | SEQ ID NO. 45 | SEQ ID NO. 46 | SEQ ID NO. 68 |
| | FBB1BR | SEQ ID NO. 47 | SEQ ID NO. 48 | SEQ ID NO. 69 |
| | FBB1C | SEQ ID NO. 49 | SEQ ID NO. 50 | SEQ ID NO. 64 |
| | FBB1D | SEQ ID NO. 51 | SEQ ID NO. 52 | SEQ ID NO. 63 |
| PS89J3 | J31AR | SEQ ID NO. 53 | SEQ ID NO. 54 | SEQ ID NO. 68 |
| | J32AR | SEQ ID NO. 55 | SEQ ID NO. 56 | SEQ ID NO. 64 |
| PS86W1 | W1FAR | SEQ ID NO. 57 | SEQ ID NO. 58 | SEQ ID NO. 68 |
| | W1FBR | SEQ ID NO. 59 | SEQ ID NO. 60 | SEQ ID NO. 69 |
| | W1FC | SEQ ID NO. 61 | SEQ ID NO. 62 | SEQ ID NO. 64 |

EXAMPLE 5

Isolation and DNA Sequencing of Full-Length Toxin Genes

Total cellular DNA was extracted from *B.t.* strains using standard procedures known in the art. See, e.g., Example 3, above. Gene libraries of size-fractionated Sau3A partial restriction fragments of total cellular DNA were constructed in the bacteriophage vector, Lambda-Gem11. Recombinant phage were packaged and plated on *E. coli* KW251 cells. Plaques were screened by hybridization with radiolabeled gene-specific probes derived from DNA fragments PCR-amplified with oligonucleotide primers SEQ ID NOS. 5 and 6. Hybridizing phage were plaque-purified and used to infect liquid cultures of *E. coli* KW251 cells for isolation of DNA by standard procedures (Maniatis, T., E. F. Fritsch, J. Sambrook [1982] *Molecular Cloning: A Laboratory Manual,* Cold Spring Harbor Laboratory, Cold Spring Harbor, N.Y.). Toxin genes were subsequently subcloned into pBluescipt vectors (Stratagene) for DNA sequence analysis.

The full-length toxin genes listed below were sequenced using Applied Biosystems (Foster City, Calif.) automated sequencing methodologies. The toxin gene sequences and the respective predicted polypeptide sequences are listed below.

| Source Strain | Peptide SEQ ID | Nucleotide SEQ ID | Toxin designation |
|---|---|---|---|
| PS86BB1 | SEQ ID NO. 70 | SEQ ID NO. 71 | 86BB1(a) |
| PS86BB1 | SEQ ID NO. 72 | SEQ ID NO. 73 | 86BB1(b) |
| PS31G1 | SEQ ID NO. 74 | SEQ ID NO. 75 | 31G1(a) |

Recombinant *E. coli* NM522 strains containing these plasmids encoding these toxins were deposited with NRRL on Jun. 27, 1997.

| Strain | Plasmid | Toxin designation | NRRL number |
|---|---|---|---|
| MR922 | pMYC2451 | 86BB1(a) | B-21794 |
| MR923 | pMYC2453 | 86BB1(b) | B-21795 |
| MR924 | pMYC2454 | 31G1(a) | B-21796 |

EXAMPLE 6

Heterologous Expression of Novel *B.t.* Toxins in *Pseudomonas fluorescens* (*P.f.*)

Full-length toxin genes were engineered into plasmid vectors by standard DNA cloning methods, and transformed into *Psuedomonas flourescens* for expression. Recombinant bacterial strains (Table 6) were grown in shake flasks for production of toxin for expression and quantitative bioassay against a variety of lepidopteran insect pests.

TABLE 6

Recombinant *Pseudomonas fluorescens* strains for heterologous expression of novel toxins

| Source Strain | Plasmid | Toxin | Recombinant P.f. Strain |
|---|---|---|---|
| PS86BB1 | pMYC2804 | 86BB1(a) | MR1259 |
| PS86BB1 | pMYC2805 | 86BB1(b) | MR1260 |
| PS31G1 | pMYC2430 | 31G1(a) | MR1264 |

EXAMPLE 7

Processing of Endotoxins with Trypsin

Cultures of *Pseudomonas fluorescens* were grown for 48 hrs. as per standard procedures. Cell pellets were harvested by centrifugation and washed three times with water and stored at −70° C. Endotoxin inclusions were isolated from cells treated with lysozyme and DNAse by differential centrifugation. Toxins isolated in this manner were then processed to limit peptides by trypsinolysis and were then used for bioassays on lepidopteran pests.

Detailed protocols follow. Toxin inclusion bodies were prepared from the washed crude cell pellets as follows:

|  | gm |
|---|---|
| Tris base | 24.22 |
| NaCl | 46.75 |
| Glycerol | 252 |
| Dithiothreitol | 0.62 |
| EDTA Disodium salt | 29.78 |
| Triton X-100 | 20 mls |

Adjust pH to 7.5 with HCl and bring up to final volume (4 L) with distilled water.

1. Thaw frozen cell pellet in 37° C. water bath.
2. Add the lysis buffer until the 500 ml polycarbonate centrifuge bottles are as full as possible ~400 ml total volume. Disperse by inversion of the bottle or using the Polytron at low rpm.
3. Centrifuge (10,000×g) for 20 minutes at 4° C.
4. Decant and discard supernatant.
5. Resuspend pellet in 5 ml of lysis buffer for every gram of pellet, using the Polytron at low rpm to disperse the pellet.
6. Add 25 mg/ml lysosyme solution to the suspension to a final concentration of 0.6 mg/ml.
7. Incubate at 37° C. for 4 minutes. Invert every 30 seconds.
8. Place suspension on ice for 1 hour.
9. Add 2.5M MgCl.6H$_2$O to the tubes to a final concentration of 60 mM. Add a 40 mg/ml deoxyribonuclease I (Sigma) solution to get a final concentration of 0.5 mg/ml.
10. Incubate overnight at 4° C.
11. Homogenize the lysate using the Polytron at low rpm.
12. Centrifuge at 10,000 g at 4° C. for 20 minutes. Decant and discard supernatant.
13. Resuspend the inclusion pellet in lysis buffer. Check microscopically for complete cell lysis.
14. Wash the inclusion pellet in lysis buffer 5 times (repeat steps 2–5).
15. Store as a suspension of 10 mM Tris-Cl pH 7.5, 0.1 mM PMSF and stored at −70° C. in 1.5 ml Eppitubes.

Digestion of inclusions with trypsin is performed as follows:
Digestion solution:

1. 2 ml 1M NaCAPS pH 10.5
2. Inclusion preparation (as much as 100 mg protein)
3. Trypsin at a 1:100 ratio with the amount of protein to be cleaved (added during the procedure)
4. H$_2$O to a final volume of 10 ml
Trypsin treatment is performed as follows:

1. Incubate the digestion solution, minus trypsin, at 37° C. for 15 minutes.
2. Add trypsin at 1:100 (trypsin:toxin protein wt/wt)
3. Incubate solution for 2 hours at 37° C. with occasional mixing by inversion.
4. Centrifuge the digestion solution for 15 minutes at 15,000 g at 4° C.
5. Remove and save the supernatant.
6. Supernatant is analyzed by SDS-PAGE and used for bioassay as discussed below.

EXAMPLE 8

Expression of a Gene from *B.t.* strain HD129 in a Chimeric Construct

A gene was isolated from *B.t.* strain HD129. This gene appears to be a pseudogene with no obvious translational initiation codon. To express this gene from HD129, we designed and constructed a gene fusion with the first 28 codons of cry1Ac in Pseudomonas expression system. The nucleotide and peptide sequences of this chimeric toxin are shown in SEQ ID NOS. 76 and 77. Upon induction, recombinant *P. fluorescens* containing this novel chimeric toxin expressed the polypeptide of the predicted size.

EXAMPLE 9

Further Sequencing of Toxin Genes

DNA of soluble toxins from the isolates listed in Table 7 were sequenced. The SEQ ID NOs. of the sequences thus obtained are also reported in Table 7.

TABLE 7

| Source Isolate | Protein SEQ ID NO. | Nucleotide SEQ ID NO. | Toxin Name |
|---|---|---|---|
| PS11B | 78 | 79 | 11B(a) |
| PS31G1 | 80 | 81 | 31G1(b) |
| PS86BB1 | 82 | 83 | 86BB1(c) |
| PS86V1 | 84 | 85 | 86V1(a) |
| PS86W1 | 86 | 87 | 86W1(a) |
| PS94R1 | 88 | 89 | 94R1(a) |
| PS185U2 | 90 | 91 | 185U2(a) |
| PS202S | 92 | 93 | 202S(a) |
| PS213E5 | 94 | 95 | 213E5(a) |
| PS218G2 | 96 | 97 | 218G2(a) |
| HD29 | 98 | 99 | 29HD(a) |
| HD110 | 100 | 101 | 110HD(a) |
| HD129 | 102 | 103 | 129HD(b) |
| HD573 | 104 | 105 | 573HD(a) |

EXAMPLE 10

Black Cutworm Bioassay

Suspensions of powders containing *B.t.* isolates were prepared by mixing an appropriate amount of powder with distilled water and agitating vigorously. Suspensions were mixed with black cutworm artificial diet (BioServ, Frenchtown, N.J.) amended with 28 grams alfalfa powder (BioServ) and 1.2 ml formalin per liter of finished diet. Suspensions were mixed with finished artificial diet at a rate of 3 ml suspension plus 27 ml diet. After vortexing, this mixture was poured into plastic trays with compartmentalized 3 ml wells (Nutrend Container Corporation, Jacksonville, Fla.). A water blank containing no *B.t.* served as the control. Early first-instar *Agrotis ipsilon* larvae (French Agricultural Services, Lamberton, Minn.) were placed singly onto the diet mixture. Wells were then sealed with "MYLAR" sheeting (ClearLam Packaging, Ill.) using a tacking iron, and several pinholes were made in each well to provide gas exchange. Larvae were held at 29° C. for four days in a 14:10 (light:dark) holding room. Mortality was recorded after four days.

The following *B.t.* isolates were found to have activity against black cutworm: PS185U2, PS11B, PS218G2, PS213E5, PS86W1, PS28C, PS86BB1, PS89J3, PS86V1, PS94R1, HD525, HD573, PS27J2, HD110 HD10, PS202S, HD29, PS101DD, HD129, and PS31G1. Bioassay results are shown in Table 8.

TABLE 8

Percentage black cutworm mortality associated with B.t. isolates

| | Estimated toxin concentration ($\mu$g toxin/mL diet) | | | |
|---|---|---|---|---|
| Sample | 200 | 100 | 50 | 25 |
| PS86BB1 | 51 | 25 | 9 | 1 |
| PS31G1 | 30 | 20 | 7 | 5 |
| PS11B | 37 | 16 | 3 | 0 |
| HD573 | 11 | 13 | 3 | 0 |
| HD129 | 87 | 73 | 43 | 7 |
| PS86V1 | 73 | 29 | 19 | 3 |
| PS89J3 | 68 | 27 | 15 | 3 |
| PS86W1 | 61 | 23 | 12 | 15 |
| PS185U2 | 69 | 32 | 14 | 16 |
| HD525 | 67 | 20 | 11 | 4 |
| water control | 1 | | | |

EXAMPLE 11

Activity of B.t. Isolates Against *Agrotis ipsilon*

Strains were tested as supernatant cultures. Samples were applied to black cutworm artificial diet (BioServ, Frenchtown, N.J.) and allowed to air dry before larval infestation. A water blank containing no B.t. served as the control. Eggs were applied to each treated well and were then sealed with "MYLAR" sheeting (ClearLam Packaging, Ill.) using a tacking iron, and several pinholes were made in each well to provide gas exchange. Bioassays were held at 25° C. for 7 days in a 14.10 (light:dark) holding room. Mortality was recorded after seven days. Strains exhibiting mortality against *A. ipsilon* (greater than water control) are reported in Table 9.

TABLE 9

Larvacidal activity of B.t. concentrated supernatants in a top load bioassay on *A. ipsilon* neonates

| Strain | Activity |
|---|---|
| PS86W1 | + |
| PS28C | + |
| PS86BB1 | + |
| PS89J3 | + |
| PS86V1 | + |
| PS94R1 | + |
| HD573 | + |

EXAMPLE 12

Activity of B.t. Isolates *Pseudomonas fluorescens* Clones Against *Heliothis virescens* (Fabricius) and *Helicoverpa zea* (Boddie)

Strains were tested as either frozen *Pseudomonas fluorescens* clones or B.t. supernatant culture samples. Suspensions of clones were prepared by individually mixing samples with distilled water and agitating vigorously. For diet incorporation bioassays, suspensions were mixed with the artificial diet at a rate of 6 mL suspension plus 54 mL diet. After vortexing, this mixture was poured into plastic trays with compartmentalized 3-ml wells (Nutrend Container Corporation, Jacksonville, Fla.). Supernatant samples were mixed at a rate of 3–6 ml with the diet as outlined above. In top load bioassays, suspensions or supernatants were applied to the top of the artificial diet and allowed to air dry before larval infestataion. A water blank served as the control. First instar larvae (USDA-ARS, Stoneville, Miss.) were placed singly onto the diet mixture. Wells were then sealed with "MYLAR" sheeting (ClearLam Packaging) using a tacking iron, and several pinholes were made in each well to provide gas exchange. Larvae were held at 25° C. for 6 days in a 14:10 (light:dark) holding room. Mortality was recorded after six days.

Results are as follows:

TABLE 10

Larvacidal activity of B.t. concentrated supernatants in a top load bioassay

| | Total Protein | H. virescens | | H. zea | |
|---|---|---|---|---|---|
| Strain | ($\mu$g/cm$^2$) | % Mortality | Stunting | % Mortality | Stunting |
| HD129 | 44.4 | 100 | yes | 50 | yes |
| | 44.4 | 81 | yes | 50 | yes |
| | 47.6 | 100 | yes | 36 | no |
| PS185U2 | 23.4 | 100 | yes | 100 | yes |
| | 23.4 | 100 | yes | 95 | yes |
| | 21.2 | 100 | yes | 96 | yes |
| | 21.2 | — | — | 100 | yes |
| PS31G1 | 8.3 | 70 | yes | 39 | yes |
| | 8.3 | 17 | yes | 30 | yes |
| | 3.6 | 29 | yes | 30 | yes |
| | 3.6 | — | — | 0 | no |

TABLE 11

Strains tested in diet incorporation bioassay on *H. virescens* and *H. zea*

| | H. virescens | | H. zea | |
|---|---|---|---|---|
| Strain | Total protein ($\mu$g/ml diet) | % Mortality | Total protein ($\mu$g/ml diet) | % Mortality |
| PS11B | NA[1] | 45 | 268 | 96 |
| PS185U2 | 55 | 100 | 55 | 100 |
| PS31G1 | 0 | 50 | 43.4 | 13 |
| PS86BB1 | 23.3 | 100 | 23.3 | 100 |
| PS86V1 | 17 | 100 | 17 | 92 |
| PS86W1 | 18 | 100 | 18 | 83 |
| PS89J3 | 13 | 100 | 13 | 81 |
| HD129 | NA | 100 | 138.3 | 13 |
| HD525 | 3 | 96 | 171.7 | 0 |
| HD573 | 3 | 96 | 78.3 | 21 |

[1]Protein information not available.

TABLE 12

*H. virescens* dose response in diet incorporation bioassays using frozen spore crystal preparations

| MR# | LC50 ($\mu$g/ml) |
|---|---|
| 1259 | 13.461 |
| 1259 trypsin | 1.974 |
| 1260 | 12.688 |
| 1260 trypsin | 0.260 |
| 1264 | 95.0 |
| 1264 trypsin | 2.823 |

EXAMPLE 13

Activity Against *Ostrinia nubilalis* (European Corn Borer)

Isolates and toxins of the subject invention can be used to control *Ostrinia nubilalis*, the European corn borer (ECB).

Activity against ECB can be readily ascertained by, for example, standard artificial diet incorporation insect bioassay procedures, using, for example, first instar larvae. In a specific embodiment, trypsin-treated clones expressing the 31G1(a) gene were found to have an LC50 value of 0.284 (μg/ml).

EXAMPLE 14

Insertion of Toxin Genes into Plants

One aspect of the subject invention is the transformation of plants with genes encoding the insecticidal toxin. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. Also, advantageously, plants encoding a truncated toxin will be used. The truncated toxin typically will encode about 55% to about 80% of the full length toxin. Methods for creating synthetic *B.t.* genes for use in plants are known in the art.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated protein that is pesticidal and that is encoded by an isolated polynucleotide, wherein said polynucleotide hybridizes with the full-length complement of a nucleotide sequence encoding amino acids 44–651 of SEQ ID NO:74, wherein hybridization occurs at 42° C. in 50% formamide, 5×Standard Saline Citrate, 1×Denhardt's solution, 31 mM KH$_2$PO$_4$, 0.25% Sodium Dodecyl Sulfate, 30 μg/ml sheared and denatured DNA, and 5% dextran sulfate, and wash occurs at 55° C. in 0.1×Standard Saline Citrate and 0.1% Sodium Dodecyl Sulfate.

2. The protein of claim 1 wherein said protein comprises a pesticidal portion of SEQ ID NO:74.

3. The protein of claim 1 wherein said protein comprises SEQ ID NO:74.

4. The protein of claim 1 wherein said protein comprises amino acids 44–651 of SEQ ID NO:74.

5. An isolated protein that is pesticidal and that is encoded by an isolated polynucleotide, wherein said polynucleotide hybridizes with the full-length complement of a nucleic acid sequence comprising nucleotides 130–1910 of SEQ ID NO:75, wherein hybridization occurs at 42° C. in 50% formamide, 5×Standard Saline Citrate, 1×Denhardt's solution, 31 mM KH$_2$PO$_4$, 0.25% Sodium Dodecyl Sulfate, 30 μg/ml sheared and denatured DNA, and 5% dextran sulfate, and wash occurs at 55° C. in 0.1×Standard Saline Citrate and 0.1% Sodium Dodecyl Sulfate.

6. A method of controlling a lepidopteran pest wherein said method comprises contacting said pest with a protein according to claim 1.

7. The method of claim 6 wherein said protein comprises a pesticidal portion of SEQ ID NO:74.

8. The method of claim 6 wherein said protein comprises SEQ ID NO:74.

9. The method of claim 6 wherein said protein comprises amino acids 44–651 of SEQ ID NO:74.

10. The method according to claim 6 wherein said protein is produced by and present in a plant.

11. The method according to claim 6 wherein said protein is produced by and present in a plant cell.

12. The method according to claim 6 wherein said protein is produced by and present in a microbial cell.

13. A method of controlling a lepidopteran pest wherein said method comprises contacting said pest with a protein of claim 5.

* * * * *

UNITED STATES PATENT AND TRADEMARK OFFICE
CERTIFICATE OF CORRECTION

PATENT NO. : 6,752,992 B2
DATED : June 22, 2004
INVENTOR(S) : Brian A. Stockhoff et al.

It is certified that error appears in the above-identified patent and that said Letters Patent is hereby corrected as shown below:

Column 2,
Line 42, "of$B.t.$" should read -- of $B.t.$ --.

Column 3,
Lines 8 and 18, "luceme" should read -- lucerne --.

Column 5,
Line 8, "11B1AR" should read -- 11B1BR --.

Column 6,
Line 20, "NO. 46is" should read -- NO. 46 is --.
Line 22, "the, toxin" should read -- the toxin --.

Column 7,
Line 35, "3G1(b)" should read -- 31G1(b) --.

Column 9,
Line 60, "ie.," should read -- i.e., --.

Column 14,
Line 42, "maybe" should read -- may be --.

Column 15,
Line 28, "maybe" should read -- may be --.

Column 16,
Line 11, "Drobes." should read -- probes. --.

Column 20,
Line 27, "$MgSO_4.7H_2O$" should read -- $MgSO_4 \cdot 7H_2O$ --.
Line 28, "$MnSO_4.H_2O$" should read -- $MnSo_4 \cdot H_2O$ --.
Line 29, "$ZnSO_4.7H_2O$" should read -- $ZnSO_4 \cdot 7H_2O$ --.
Line 30, "$FeSO_4.7H_2O$" should read -- $FeSO_4 \cdot 7H_2O$ --.
Line 33, "$CaCl_2.2H_2O$" should read -- $CaCl_2 \cdot 2H_2O$ --.

UNITED STATES PATENT AND TRADEMARK OFFICE
CERTIFICATE OF CORRECTION

PATENT NO.    : 6,752,992 B2
DATED         : June 22, 2004
INVENTOR(S)   : Brian A. Stockhoff et al.

It is certified that error appears in the above-identified patent and that said Letters Patent is hereby corrected as shown below:

Column 23,
Line 14 (Table 3), "Sac 1" should read -- SacI --.
Line 23 (Table 3), "XbaI" should read -- XbaI --.
Line 48 (Table 4), "XbaI" should read -- XbaI --.
Line 57, "*epsilon*" should read -- *ipsilon* --.

Column 27,
Line 10, "as follows:" should read -- as follows: 4L of Lysis Buffer (prepare day of use) --.
Line 36, "$MgCl.6H_2O$" should read -- $MgCl \cdot 6H_2O$ --.

Column 29,
Line 2, "HD110 HD10," should read -- HD110, HD10, --.
Line 35, "14.10" should read -- 14:10 --.

Column 30,
Line 46, "HD573" should read -- HD573A --.

Signed and Sealed this

Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,752,992 B2
APPLICATION NO. : 10/099285
DATED : June 22, 2004
INVENTOR(S) : Brian A. Stockoff et al.

It is certified that error appears in the above-identified patent and that said Letters Patent is hereby corrected as shown below:

Column 2,
Line 42, "of*B.t.*" should read -- of *B.t.* --.

Column 3,
Line 8, "luceme" should read -- lucerne --.
Line 18, "luceme" should read -- lucerne--.

Column 5,
Line 8, "11B1AR" should read -- 11B1BR--.

Column 6,
Line 20, "NO. 46is" should read    --NO. 46 is --.
Line 22, "the, toxin" should read -- the toxin --.

Column 7,
Line 35, "3G1(b)" should read -- 31G1(b) --.

Column 9,
Line 60, "ie.," should read -- i.e., --.

Column 14,
Line 42, "maybe" should read -- may be --.

Column 15,
Line 28, "maybe" should read -- may be --.

Column 16,
Line 11, "Drobes." should read -- probes. --.

Column 20,
Line 27, "MgSO$_4$.7H$_2$O" should read -- MgSO$_4$·7H$_2$O --.
Line 28, "MnSO$_4$.H$_2$O" should read -- MnSO$_4$·H$_2$O --.
Line 29, "ZnSO$_4$.7H$_2$O" should read -- ZnSO$_4$·7H$_2$O --.
Line 30, "FeSO$_4$.7H$_2$O" should read -- FeSO$_4$·7H$_2$O --.
Line 33, "CaCl$_2$.2H$_2$O" should read -- CaCl$_2$·2H$_2$O --.

Column 23,
Line 14 (Table 3), "Sac1" should read -- SacI --.
Line 23 (Table 3), "XbaI" should read -- XbaI --.
Line 48 (Table 4), "XbaI" should read -- XbaI --.
Line 57, "*epsilon*" should read -- *ipsilon* --.

UNITED STATES PATENT AND TRADEMARK OFFICE
CERTIFICATE OF CORRECTION

PATENT NO. : 6,752,992 B2
APPLICATION NO. : 10/099285
DATED : June 22, 2004
INVENTOR(S) : Brian A. Stockoff et al.

It is certified that error appears in the above-identified patent and that said Letters Patent is hereby corrected as shown below:

Column 27,
Line 10, "as follows:" should read
-- as follows: 4L of Lysis Buffer (prepare day of use) --.
Line 36, "MgCl.6H$_2$O" should read -- MgCl·6H$_2$O --.

Column 29,
Line 2, "HD110 HD10," should read -- HD110, HD10,--.
Line 35, "14.10" should read -- 14:10 --.

Column 30,
Line 46, "HD573" should read -- HD573A --.

Signed and Sealed this

Fourteenth Day of August, 2007

JON W. DUDAS
*Director of the United States Patent and Trademark Office*

SEQUENCE LISTING (1) GENERAL INFORMATION:

(iii) NUMBER OF SEQUENCES: 105

(2) INFORMATION FOR SEQ ID NO: 1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

CGTGGCTATA TCCTTCGTGT YAC                                                 23

(2) INFORMATION FOR SEQ ID NO: 2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

ACRATRAATG TTCCTTCYGT TTC                                                 23

(2) INFORMATION FOR SEQ ID NO: 3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GGATATGTMT TACGTGTAAC WGC                                                 23

(2) INFORMATION FOR SEQ ID NO: 4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CTACACTTTC TATRTTGAAT RYACCTTC                                        28

(2) INFORMATION FOR SEQ ID NO: 5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

CCAGWTTTAY AGGAGG                                                             16

(2) INFORMATION FOR SEQ ID NO: 6:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GTAAACAAGC TCGCCACCGC                                                      20

(2) INFORMATION FOR SEQ ID NO: 7:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Pro Gly Phe Xaa Gly Gly Asp Ile Leu Arg Arg Thr Ser Pro Xaa Gln
1               5                  10                  15

Ile Ser Xaa Leu Arg Val Asn Ile Thr Ala Pro Leu Ser Gln Arg Tyr
            20                  25                  30

Arg Val Arg Ile Xaa Xaa Ala Ser Thr Thr Xaa Xaa Gln Phe His Thr
        35                  40                  45

Ser Ile Xaa Gly Arg Pro Ile Asn Gln Gly Asn Phe Ser Xaa Thr Met
    50                  55                  60

Ser Ser Gly Ser Asn Leu Gln Ser Gly Xaa Phe Arg Thr Val Gly Phe
65                  70                  75                  80

Thr Thr Pro Xaa Asn Phe Ser Asn Gly Ser Val Phe Thr Leu Ser
                85                  90                  95

Xaa His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Xaa Lys Ala Val Ala Ser Leu Phe
    130                 135

(2) INFORMATION FOR SEQ ID NO: 8:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CCAGGATTTA YAGGAGGAGA TATTCTTCGA AGAACTTCAC CTGKSCAGAT TTCAWCCTTA           60

AGAGTAAATA TTACTGCACC ATTATCACAA AGATATCGGG TAAGAATTCR CWACGCTTCT          120

ACYACAWATT TWCAATTCCA TACATCAATT GRCGGAAGAC CTATTAATCA GGGKAATTTT          180

TCASCAACTA TGAGTAGTGG GAGTAATTTA CAGTCCGGAA KCTTTAGGAC TGTAGGTTTT          240

ACTACTCCGT KTAACTTTTC AAATGGATCA AGTGTATTTA CGTTAAGTKC TCATGTCTTC          300

AATTCAGGCA ATGAAGTTTA TAGATCGA ATTGAATTTG TTCCGGCAGA AGTAACCTTT           360

GAGGCAGAAT ATGATTTAGA AAGAGCACMA AAGGCGGTGG CGAGCTTGTT TAC                413
```

(2) INFORMATION FOR SEQ ID NO: 9:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Pro Gly Phe Thr Gly Gly Asp Ile Leu Arg Arg Thr Asp Gly Gly Xaa
1               5                   10                  15

Val Gly Thr Ile Arg Ala Asn Val Asn Ala Pro Leu Thr Gln Gln Tyr
            20                  25                  30

Arg Ile Arg Leu Arg Tyr Ala Ser Thr Thr Ser Phe Val Val Asn Leu
        35                  40                  45

Phe Val Asn Asn Ser Ala Ala Gly Phe Thr Leu Pro Ser Thr Met Ala
    50                  55                  60

Gln Asn Gly Ser Leu Thr Xaa Glu Ser Phe Asn Thr Leu Glu Val Thr
65                  70                  75                  80

His Xaa Ile Arg Phe Ser Gln Ser Asp Thr Thr Leu Arg Leu Asn Ile
        85                  90                  95

Phe Pro Ser Ile Ser Gly Gln Xaa Val Tyr Val Asp Lys Xaa Glu Ile
            100                 105                 110

Val Pro Xaa Asn Pro Thr Arg Glu Ala Glu Glu Asp Leu Glu Asp Xaa
        115                 120                 125

Lys Lys Ala Val Ala Ser Leu Phe
130                 135
```

(2) INFORMATION FOR SEQ ID NO: 10:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
CCAGGWTTTA CAGGAGGGGA TATACTTCGA AGAACGGACG GTGGTRCAGT TGGAACGATT    60
AGAGCTAATG TTAATGCCCC ATTAACACAA CAATATCGTA TAAGATTACG CTATGCTTCG   120
ACAACAAGTT TTGTTGTTAA TTTATTTGTT AATAATAGTG CGGCTGGCTT TACTTTACCG   180
AGTACAATGG CTCAAAATGG TTCTTTAACA YRCGAGTCGT TTAATACCTT AGAGGTAACT   240
CATWCTATTA GATTTTCACA GTCAGATACT ACACTTAGGT TGAATATATT CCCGTCYATC   300
TCTGGTCAAG RAGTGTATGT AGATAAACWT GAAATCGTTC CAWTTAACCC GACACGAGAA   360
GCGGAAGAAG ATTTAGAAGA TSCAAAGAAA GCGGTGGCGA GCTTGTTTAC              410
```

(2) INFORMATION FOR SEQ ID NO: 11:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Pro Gly Phe Xaa Gly Gly Asp Ile Leu Arg Arg Thr Gly Val Gly Thr
 1               5                  10                  15

Phe Gly Thr Ile Arg Val Arg Xaa Thr Ala Pro Leu Thr Gln Arg Tyr
                20                  25                  30

Arg Ile Arg Phe Arg Phe Ala Xaa Thr Thr Asn Leu Phe Ile Gly Ile
            35                  40                  45

Arg Val Gly Asp Arg Gln Val Asn Tyr Phe Asp Phe Gly Arg Thr Met
    50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
                85                  90                  95

Ala Asn Ala Phe Ser Ala Gly Gln Glu Val Tyr Phe Asp Arg Ile Glu
                100                 105                 110

Ile Ile Pro Val Asn Pro Ala Arg Glu Ala Lys Glu Asp Leu Glu Ala
            115                 120                 125

Ala Lys Lys Ala Val Ala Ser Leu Phe
    130                 135
```

(2) INFORMATION FOR SEQ ID NO: 12:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
CCAGGTTTTA YAGGAGGGGA TATACTCCGA AGAACAGGGG TTGGTACATT TGGAACAATA    60
AGGGTAAGGA YTACTGCCCC CTTAACACAA AGATATCGCA TAAGATTCCG TTTCGCTTYT   120
ACCACAAATT TGTTCATTGG TATAAGAGTT GGTGATAGAC AAGTAAATTA TTTTGACTTC   180
GGAAGAACAA TGAACAGAGG AGATGAATTA AGGTACGAAT CTTTTGCTAC AAGGGAGTTT   240
ACTACTGATT TTAATTTTAG ACAACCTCAA GAATTAATCT CAGTGTTTGC AAATGCATTT   300
AGCGCTGGTC AAGAAGTTTA TTTTGATAGA ATTGAGATTA TCCCCGTTAA TCCCGCACGA   360
GAGGCGAAAG AGGATYTAGA AGCAGCAAAG AAAGCGGTGG CGAGCTTGTT TAC          413
```

(2) INFORMATION FOR SEQ ID NO: 13:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

```
Gly Phe Ile Gly Gly Ala Leu Leu Gln Arg Thr Asp His Gly Ser Leu
 1               5                  10                  15

Gly Val Leu Arg Val Gln Phe Pro Leu His Leu Arg Gln Gln Tyr Arg
                20                  25                  30

Ile Xaa Val Arg Tyr Ala Xaa Thr Thr Asn Ile Arg Leu Ser Val Asn
            35                  40                  45

Gly Ser Phe Gly Thr Ile Ser Gln Asn Leu Pro Ser Thr Met Arg Leu
    50                  55                  60
```

```
Gly Glu Asp Leu Arg Tyr Gly Ser Phe Ala Ile Arg Glu Phe Asn Thr
 65                  70                  75                  80

Ser Ile Arg Pro Thr Ala Ser Pro Asp Gln Ile Arg Leu Thr Ile Glu
                 85                  90                  95

Pro Ser Phe Ile Arg Gln Glu Val Tyr Val Asp Arg Ile Glu Phe Ile
                100                 105                 110

Pro Val Asn Pro Thr Arg Glu Ala Lys Glu Asp Leu Glu Ala Ala Lys
            115                 120                 125

Lys Ala Val Ala Ser Leu Phe
    130                 135

(2) INFORMATION FOR SEQ ID NO: 14:

(i) SEQUENCE CHARACTERISTICS:
        (A) LENGTH: 407 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:
```

| | | | | | |
|---|---|---|---|---|---|
| GGMTTTATAG | GAGGAGCTCT | ACTTCAAAGG | ACTGACCATG | GTTCGCTTGG | AGTATTGAGG |     60 |
| GTCCAATTTC | CACTTCACTT | AAGACAACAA | TATCGTATTA | SAGTCCGTTA | TGCTTYTACA |    120 |
| ACAAATATTC | GATTGAGTGT | GAATGGCAGT | TTCGGTACTA | TTTCTCAAAA | TCTCCCTAGT |    180 |
| ACAATGAGAT | TAGGAGAGGA | TTTAAGATAC | GGATCTTTTG | CTATAAGAGA | GTTTAATACT |    240 |
| TCTATTAGAC | CCACTGCAAG | TCCGGACCAA | ATTCGATTGA | CAATAGAACC | ATCTTTTATT |    300 |
| AGACAAGAGG | TCTATGTAGA | TAGAATTGAG | TTCATTCCAG | TTAATCCGAC | GCGAGAGGCG |    360 |
| AAAGAGGATC | TAGAAGCAGC | AAAAAAAGCG | GTGGCGAGCT | TGTTTAC |  |    407 |

```
(2) INFORMATION FOR SEQ ID NO: 15:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Pro Gly Phe Thr Gly Gly Asp Ile Leu Arg Arg Thr Ser Pro Gly Gln
  1               5                  10                  15

Ile Ser Thr Leu Arg Val Asn Ile Thr Ala Pro Leu Ser Gln Arg Tyr
                 20                  25                  30

Arg Val Arg Ile Arg Tyr Ala Ser Thr Thr Asn Leu Gln Phe His Thr
             35                  40                  45

Ser Ile Asp Gly Arg Pro Ile Asn Gln Gly Asn Phe Ser Ala Thr Met
     50                  55                  60

Ser Ser Gly Ser Asn Leu Gln Ser Gly Ser Phe Arg Thr Val Gly Phe
 65                  70                  75                  80

Thr Thr Pro Phe Asn Phe Ser Asn Gly Ser Ser Val Phe Thr Leu Ser
                 85                  90                  95

Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
            115                 120                 125
```

```
Ala Gln Lys Ala Val Ala Ser Leu Phe
    130                 135

(2) INFORMATION FOR SEQ ID NO: 16:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CCAGGATTTA CAGGAGGAGA TATTCTTCGA AGAACTTCAC CTGGCCAGAT TTCAACCTTA      60

AGAGTAAATA TTACTGCACC ATTATCACAA AGATATCGGG TAAGAATTCG CTACGCTTCT     120

ACCACAAATT TACAATTCCA TACATCAATT GACGGAAGAC CTATTAATCA GGGGAATTTT     180

TCAGCAACTA TGAGTAGTGG GAGTAATTTA CAGTCCGGAA GCTTTAGGAC TGTAGGTTTT     240

ACTACTCCGT TTAACTTTTC AAATGGATCA AGTGTATTTA CGTTAAGTGC TCATGTCTTC     300

AATTCAGGCA ATGAAGTTTA TATAGATCGA ATTGAATTTG TTCCGGCAGA AGTAACCTTT     360

GAGGCAGAAT ATGATTTAGA AAGAGCGCAA AAGGCGGTGG CGAGCTTGTT TAC            413

(2) INFORMATION FOR SEQ ID NO: 17:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

Pro Gly Phe Xaa Gly Gly Asp Ile Leu Arg Arg Thr Asp Gly Gly Ala
1               5                   10                  15

Val Gly Thr Ile Arg Ala Asn Val Asn Ala Pro Leu Thr Gln Gln Tyr
            20                  25                  30

Arg Ile Arg Leu Arg Tyr Ala Ser Thr Thr Ser Phe Val Val Asn Leu
        35                  40                  45

Phe Val Asn Asn Ser Ala Ala Gly Phe Thr Leu Pro Ser Thr Met Ala
    50                  55                  60

Gln Asn Gly Ser Leu Thr Tyr Glu Ser Phe Asn Thr Leu Glu Val Thr
65                  70                  75                  80

His Thr Ile Arg Phe Ser Gln Ser Asp Thr Thr Leu Arg Leu Asn Ile
                85                  90                  95

Phe Pro Ser Ile Ser Gly Gln Glu Val Tyr Val Asp Lys Leu Glu Ile
            100                 105                 110

Val Pro Ile Asn Pro Thr Arg Glu Ala Glu Asp Leu Glu Asp Ala
        115                 120                 125

Lys Lys Ala Val Ala Ser Leu Phe
    130                 135

(2) INFORMATION FOR SEQ ID NO: 18:

(i) SEQUENCE CHARACTERISTICS:
        (A) LENGTH: 410 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 18:

```
CCAGGWTTTA YAGGAGGGGA TATACTTCGA AGAACGGACG GTGGTGCAGT TGGAACGATT      60

AGAGCTAATG TTAATGCCCC ATTAACACAA CAATATCGTA TAAGATTACG CTATGCTTCG     120

ACAACAAGTT TTGTTGTTAA TTTATTTGTT AATAATAGTG CGGCTGGCTT TACTTTACCG     180

AGTACAATGG CTCAAAATGG TTCTTTAACA TACGAGTCGT TTAATACCTT AGAGGTAACT     240

CATACTATTA GATTTTCACA GTCAGATACT ACACTTAGGT TGAATATATT CCCGTCTATC     300

TCTGGTCAAG AAGTGTATGT AGATAAACTT GAAATCGTTC CAATTAACCC GACACGAGAA     360

GCGGAAGAAG ATTTAGAAGA TGCAAAGAAA GCGGTGGCGA GCTTGTTTAC                410
```

(2) INFORMATION FOR SEQ ID NO: 19:

(i) SEQUENCE CHARACTERISTICS:
             (A) LENGTH: 137 amino acids
             (B) TYPE: amino acid
             (C) STRANDEDNESS: single
             (D) TOPOLOGY: linear (ii) MOLECULE TYPE: protein (xi) SEQUENCE DESCRIPTION: SEQ ID NO: 19:

```
Pro Gly Phe Xaa Gly Gly Asp Ile Leu Arg Arg Thr Ser Pro Gly Gln
  1               5                  10                  15

Ile Ser Thr Leu Arg Val Asn Ile Thr Ala Pro Leu Ser Gln Arg Tyr
             20                  25                  30

Arg Val Arg Ile Arg Tyr Ala Xaa Thr Thr Asn Leu Gln Phe His Thr
         35                  40                  45

Ser Ile Asp Gly Arg Pro Ile Asn Gln Gly Asn Phe Ser Ala Thr Met
     50                  55                  60

Ser Ser Gly Ser Asn Leu Gln Ser Gly Ser Phe Arg Thr Val Gly Phe
 65                  70                  75                  80

Thr Thr Pro Phe Asn Phe Ser Asn Gly Ser Ser Val Phe Thr Leu Ser
                 85                  90                  95

Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125

Ala Gln Lys Ala Val Ala Ser Leu Phe
    130                 135
```

(2) INFORMATION FOR SEQ ID NO: 20:

(i) SEQUENCE CHARACTERISTICS:
             (A) LENGTH: 413 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 20:

```
CCAGGWTTTA YAGGAGGAGA TATTCTTCGA AGAACTTCAC CTGGCCAGAT TTCAACCTTA      60

AGAGTAAATA TTACTGCACC ATTATCACAA AGATATCGGG TAAGAATTCG CTACGCTTYT     120

ACYACAAATT TACAATTCCA TACATCAATT GACGGAAGAC CTATTAATCA GGKAATTTT     180

TCAGCAACTA TGAGTAGTGG GAGTAATTTA CAGTCCGGAA GCTTTAGGAC TGTAGGTTTT     240
```

```
ACTACTCCGT TTAACTTTTC AAATGGATCA AGTGTATTTA CGTTAAGTGC TCATGTCTTC        300

AATTCAGGCA ATGAAGTTTA TATAGATCGA ATTGAATTTG TTCCGGCAGA AGTAACCTTT        360

GAGGCAGAAT ATGATTTAGA AAGAGCACAA AAGGCGGTGG CGAGCTTGTT TAC              413
```

(2) INFORMATION FOR SEQ ID NO: 21:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

```
Phe Thr Gly Gly Asp Ile Leu Arg Arg Asn Thr Ile Gly Glu Phe Val
1               5                   10                  15

Ser Leu Gln Val Asn Ile Asn Ser Pro Ile Thr Gln Arg Tyr Arg Leu
            20                  25                  30

Arg Phe Arg Tyr Ala Ser Ser Arg Asp Ala Arg Ile Thr Val Ala Ile
        35                  40                  45

Gly Gly Gln Ile Arg Val Asp Met Thr Leu Glu Lys Thr Met Glu Ile
    50                  55                  60

Gly Glu Ser Leu Thr Xaa Arg Thr Phe Ser Tyr Thr Asn Phe Ser Asn
65                  70                  75                  80

Pro Phe Ser Phe Arg Ala Asn Pro Asp Ile Ile Arg Ile Ala Glu Glu
            85                  90                  95

Leu Pro Ile Arg Gly Gly Glu Leu Val Tyr
            100                 105
```

(2) INFORMATION FOR SEQ ID NO: 22:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
TTTACAGGAG GGGATATCCT TCGAAGAAAT ACCATTGGTG AGTTTGTGTC TTTACAAGTC        60

AATATTAACT CACCAATTAC CCAAAGATAC CGTTTAAGAT TTCGTTATGC TTCCAGTAGG       120

GATGCACGAA TTACTGTAGC GATAGGAGGA CAAATTAGAG TAGATATGAC CCTTGAAAAA       180

ACCATGGAAA TTGGGGAGAG CTTAACATYT AGAACATTTA GCTATACCAA TTTTAGTAAT       240

CCTTTTTCAT TTAGGGCTAA TCCAGATATA ATTAGAATAG CTGAAGAACT TCCTATTCGC       300

GGTGGCGAGC TTGTTTAC                                                    318
```

(2) INFORMATION FOR SEQ ID NO: 23:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

```
Ile Pro Leu Val Ser Leu Cys Leu Tyr Lys Ser Ile Leu Thr His Gln
1               5                   10                  15

Leu Pro Lys Asp Thr Val Xaa Xaa Phe Val Met Leu Pro Val Gly Met
            20                  25                  30

His Glu Leu Leu Xaa Arg Xaa Glu Asp Lys Leu Glu Xaa Ile Xaa Pro
                35              40                  45

Leu Lys Lys Pro Trp Lys Leu Gly Arg Ala Xaa His Leu Glu His Leu
50                  55                  60

Ala Ile Pro Ile Leu Val Ile Leu Phe His Leu Gly Leu Ile Gln Ile
65                  70                  75                  80

Xaa Leu Glu Xaa Leu Lys Asn Phe Leu Phe Ala Val Ala Ser Leu Phe
                85                  90                  95
```

(2) INFORMATION FOR SEQ ID NO: 24:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
AAATACCATT GGTGAGTTTG TGTCTTTACA AGTCAATATT AACTCACCAA TTACCCAAAG    60

ATACCGTTTA ARATTTCGTT ATGCTTCCAG TAGGGATGCA CGAATTACTG TAGCGATAGG   120

AGGACAAATT AGAGTAGATA TGACCCTTGA AAAAACCATG GAAATTGGGG AGAGCTTAAC   180

ATCTAGAACA TTTAGCTATA CCAATTTTAG TAATCCTTTT TCATTTAGGG CTAATCCAGA   240

TATAATTAGA ATAGCTGAAG AACTTCCTAT TCGCGGTGGC GAGCTTGTTT AC           292
```

(2) INFORMATION FOR SEQ ID NO: 25:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

```
Pro Gly Phe Xaa Gly Gly Asp Ile Leu Arg Arg Asn Thr Ile Gly Glu
1               5                   10                  15

Phe Val Ser Leu Gln Val Asn Ile Asn Ser Pro Ile Thr Gln Arg Tyr
            20                  25                  30

Arg Leu Arg Phe Arg Tyr Ala Ser Ser Arg Asp Ala Arg Ile Thr Val
                35                  40                  45

Ala Ile Gly Gly Gln Ile Arg Val Xaa Met Thr Leu Glu Lys Thr Met
50                  55                  60

Glu Ile Gly Glu Ser Leu Thr Ser Arg Thr Phe Ser Tyr Thr Asn Phe
65                  70                  75                  80

Ser Asn Pro Phe Ser Phe Arg Ala Asn Pro Asp Ile Ile Arg Ile Ala
                85                  90                  95

Glu Glu Leu Pro Ile Arg Gly Gly Glu Leu Val Tyr
                100                 105
```

(2) INFORMATION FOR SEQ ID NO: 26:

(i) SEQUENCE CHARACTERISTICS:

(A) LENGTH: 324 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

CCAGGWTTTA YAGGAGGGGA TATCCTTCGA AGAAATACCA TTGGTGAGTT TGTGTCTTTA    60

CAAGTCAATA TTAACTCACC AATTACCCAA AGATACCGTT TAAGATTTCG TTATGCTTCC   120

AGTAGGGATG CACGAATTAC TGTAGCGATA GGAGGACAAA TTAGAGTAKA TATGACCCTT   180

GAAAAAACCA TGGAAATTGG GGAGAGCTTA ACATCTAGAA CATTTAGCTA TACCAATTTT   240

AGTAATCCTT TTTCATTTAG GGCTAATCCA GATATAATTA GAATAGCTGA AGAACTTCCT   300

ATTCGCGGTG GCGAGCTTGT TTAC                                        324

(2) INFORMATION FOR SEQ ID NO: 27:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

Gly Phe Xaa Gly Gly Asp Val Ile Arg Arg Thr Asn Thr Gly Gly Phe
1               5                   10                  15

Gly Ala Ile Arg Val Ser Val Thr Gly Pro Leu Thr Gln Arg Tyr Arg
            20                  25                  30

Ile Arg Phe Arg Tyr Ala Ser Thr Ile Asp Phe Asp Phe Val Thr
        35                  40                  45

Arg Gly Gly Thr Thr Ile Asn Asn Phe Arg Phe Thr Arg Thr Met Asn
50                  55                  60

Arg Gly Gln Glu Ser Arg Tyr Glu Ser Tyr Arg Thr Val Glu Phe Thr
65                  70                  75                  80

Thr Pro Phe Asn Phe Thr Gln Ser Gln Asp Ile Ile Arg Thr Xaa Ile
                85                  90                  95

Gln Gly Leu Ser Gly Asn Gly Glu Val Tyr Leu Asp Arg Ile Glu Ile
            100                 105                 110

Ile Pro Val Asn Pro Thr Arg Glu Ala Glu Glu Asp Leu Glu Ala Ala
            115                 120                 125

Lys Lys Ala Val Ala Ser Leu Phe
130                 135

(2) INFORMATION FOR SEQ ID NO: 28:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

AGGATTTAYA GGAGGAGATG TAATCCGAAG AACAAATACT GGTGGATTCG GAGCAATAAG    60

GGTGTCGGTC ACTGGACCGC TAACACAACG ATATCGCATA AGGTTCCGTT ATGCTTCGAC   120

AATAGATTTT GATTTCTTTG TAACACGTGG AGGAACTACT ATAAATAATT TTAGATTTAC   180

```
ACGTACAATG AACAGGGGAC AGGAATCAAG ATATGAATCC TATCGTACTG TAGAGTTTAC      240

AACTCCTTTT AACTTTACAC AAAGTCAAGA TATAATTCGA ACAYCTATCC AGGGACTTAG      300

TGGAAATGGG GAAGTATACC TTGATAGAAT TGAAATCATC CCTGTAAATC CAACACGAGA      360

AGCGGAAGAR GATTTAGAAG CGGCGAAGAA AGCGGTGGCG AGCTTGTTTA C              411
```

(2) INFORMATION FOR SEQ ID NO: 29:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 29:

```
Pro Gly Phe Ile Gly Gly Ala Leu Leu Gln Arg Thr Asp His Gly Ser
 1               5                  10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
 50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Glu Asp Leu Glu Ala Ala
        115                 120                 125

Lys Lys Ala Val Ala Ser Leu Phe
    130                 135
```

(2) INFORMATION FOR SEQ ID NO: 30:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

```
CCAGGATTTA TAGGAGGAGC TCTACTTCAA AGGACTGACC ATGGTTCGCT TGGAGTATTG       60

AGGGTCCAAT TTCCACTTCA CTTAAGACAA CAATATCGTA TTAGAGTCCG TTATGCTTCT      120

ACAACAAATA TTCGATTGAG TGTGAATGGC AGTTTCGGTA CTATTTCTCA AAATCTCCCT      180

AGTACAATGA GATTAGGAGA GGATTTAAGA TACGGATCTT TTGCTATAAG AGAGTTTAAT      240

ACTTCTATTA GACCCACTGC AAGTCCGGAC CAAATTCGAT TGACAATAGA ACCATCTTTT      300

ATTAGACAAG AGGTCTATGT AGATAGAATT GAGTTCATTC CAGTTAATCC GACGCGAGAG      360

GCGAAAGAGG ATCTAGAAGC AGCAAAAAAA GCGGTGGCGA GCTTGTTTAC                 410
```

(2) INFORMATION FOR SEQ ID NO: 31:

(i) SEQUENCE CHARACTERISTICS:
    (A) LENGTH: 142 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 31:

```
Pro Gly Phe Xaa Gly Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
            20                  25                  30

Arg Val Arg Val Arg Phe Ala Ser Ser Gly Asn Phe Ser Ile Arg Ile
        35                  40                  45

Leu Arg Gly Asn Thr Ser Ile Ala Tyr Gln Arg Phe Gly Ser Thr Met
    50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
            100                 105                 110

Ile Asp Arg Ile Glu Ile Ile Pro Val Asn Pro Ala Arg Glu Ala Glu
        115                 120                 125

Glu Asp Leu Glu Ala Ala Lys Lys Ala Val Ala Ser Leu Phe
    130                 135                 140
```

(2) INFORMATION FOR SEQ ID NO: 32:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
CCAGGWTTTA YAGGAGGGGG TATACTCCGA AGAACAACTA ATGGCACATT TGGAACGTTA      60

AGAGTAACAG TTAATTCACC ATTAACACAA AGATATCGCG TAAGAGTTCG TTTTGCTTCA     120

TCAGGAAATT TCAGCATAAG GATACTGCGT GGAAATACCT CTATAGCTTA TCAAAGATTT     180

GGGAGTACAA TGAACAGAGG ACAGGAACTA ACTTACGAAT CATTTGTCAC AAGTGAGTTC     240

ACTACTAATC AGAGCGATCT GCCTTTTACA TTTACACAAG CTCAAGAAAA TTTAACAATC     300

CTTGCAGAAG GTGTTAGCAC CGGTAGTGAA TATTTTATAG ATAGAATTGA AATCATCCCT     360

GTGAACCCGG CACGAGAAGC AGAAGAGGAT TTAGAAGCRG CGAAGAAAGC GGTGGCGAGC     420

TTGTTTAC                                                             428
```

(2) INFORMATION FOR SEQ ID NO: 33:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 33:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
50                      55                  60

Leu Gly Glu Asp Leu Arg Tyr Gly Ser Phe Ala Ile Arg Glu Phe Asn
65              70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
                100                 105                 110

Ile Pro Val Asn Pro Thr Arg Glu Ala Lys Glu Asp Leu Glu Ala Ala
            115                 120                 125

Lys Lys Ala Val Ala Ser Leu Phe
130                 135
```

(2) INFORMATION FOR SEQ ID NO: 34:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

```
CCAGGATTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT     120

ACAACAAATA TTCGATTGAG TGTGAATGGC AGTTTCGGTA CTATTTCTCA AAATCTCCCT     180

AGTACAATGA GATTAGGAGA GGATTTAAGA TACGGATCTT TTGCTATAAG AGAGTTTAAT     240

ACTTCTATTA GACCCACTGC AAGTCCGGAC CAAATTCGAT TGACAATAGA ACCATCTTTT     300

ATTAGACAAG AGGTCTATGT AGATAGAATT GAGTTCATTC CAGTTAATCC GACGCGAGAG     360

GCGAAAGAGG ATCTAGAAGC AGCAAAAAAA GCGGTGGCGA GCTTGTTTAC                410
```

(2) INFORMATION FOR SEQ ID NO: 35:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 35:

```
Pro Gly Phe Thr Gly Gly Asp Ile Leu Arg Arg Thr Gly Val Gly Thr
1               5                   10                  15

Phe Gly Thr Ile Arg Val Arg Thr Thr Ala Pro Leu Thr Gln Arg Tyr
            20                  25                  30

Arg Ile Arg Phe Arg Phe Ala Ser Thr Thr Asn Leu Phe Ile Gly Ile
        35                  40                  45

Arg Val Gly Asp Arg Gln Val Asn Tyr Phe Asp Phe Gly Arg Thr Met
50                  55                  60
```

```
Asn Arg Gly Asp Glu Leu Arg Tyr Glu Ser Phe Ala Thr Arg Glu Phe
 65                  70                  75                  80

Thr Thr Asp Phe Asn Phe Arg Gln Pro Gln Glu Leu Ile Ser Val Phe
                 85                  90                  95

Ala Asn Ala Phe Ser Ala Gly Gln Glu Val Tyr Phe Asp Arg Ile Glu
            100                 105                 110

Ile Ile Pro Val Asn Pro Ala Arg Glu Ala Lys Glu Asp Leu Glu Ala
        115                 120                 125

Ala Lys Lys Ala Val Ala Ser Leu Phe
    130                 135
```

(2) INFORMATION FOR SEQ ID NO: 36:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

```
CCAGGTTTTA CAGGAGGGGA TATACTCCGA AGAACAGGGG TTGGTACATT TGGAACAATA    60
AGGGTAAGGA CTACTGCCCC CTTAACACAA AGATATCGCA TAAGATTCCG TTTCGCTTCT   120
ACCACAAATT TGTTCATTGG TATAAGAGTT GGTGATAGAC AAGTAAATTA TTTTGACTTC   180
GGAAGAACAA TGAACAGAGG AGATGAATTA AGGTACGAAT CTTTTGCTAC AAGGGAGTTT   240
ACTACTGATT TTAATTTTAG ACAACCTCAA GAATTAATCT CAGTGTTTGC AAATGCATTT   300
AGCGCTGGTC AAGAAGTTTA TTTTGATAGA ATTGAGATTA TCCCCGTTAA TCCCGCACGA   360
GAGGCGAAAG AGGATCTAGA AGCAGCAAAG AAAGCGGTGG CGAGCTTGTT TAC          413
```

(2) INFORMATION FOR SEQ ID NO: 37:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 37:

```
Pro Gly Phe Thr Gly Gly Asp Ile Leu Arg Arg Thr Ser Pro Gly Gln
  1               5                  10                  15

Ile Ser Thr Leu Arg Val Asn Ile Thr Ala Pro Leu Ser Gln Arg Tyr
             20                  25                  30

Arg Val Arg Ile Arg Tyr Ala Ser Thr Thr Asn Leu Gln Phe His Thr
         35                  40                  45

Ser Ile Asp Gly Arg Pro Ile Asn Gln Gly Asn Phe Ser Ala Thr Met
     50                  55                  60

Ser Ser Gly Ser Asn Leu Gln Ser Gly Ser Phe Arg Thr Val Gly Phe
 65                  70                  75                  80

Thr Thr Pro Phe Asn Phe Ser Asn Gly Ser Ser Val Phe Thr Leu Ser
                 85                  90                  95

Ala His Val Phe Asn Ser Gly Asn Glu Val Tyr Ile Asp Arg Ile Glu
            100                 105                 110

Phe Val Pro Ala Glu Val Thr Phe Glu Ala Glu Tyr Asp Leu Glu Arg
        115                 120                 125
```

```
Ala Gln Lys Ala Val Ala Ser Leu Phe
    130                 135
```

(2) INFORMATION FOR SEQ ID NO: 38:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

```
CCAGGWTTTA CAGGAGGAGA TATTCTTCGA AGAACTTCAC CTGGCCAGAT TTCAACCTTA      60

AGAGTAAATA TTACTGCACC ATTATCACAA AGATATCGGG TAAGAATTCG CTACGCTTCT     120

ACCACAAATT TACAATTCCA TACATCAATT GACGGAAGAC CTATTAATCA GGGGAATTTT     180

TCAGCAACTA TGAGTAGTGG GAGTAATTTA CAGTCCGGAA GCTTTAGGAC TGTAGGTTTT     240

ACTACTCCGT TTAACTTTTC AAATGGATCA AGTGTATTTA CGTTAAGTGC TCATGTCTTC     300

AATTCAGGCA ATGAAGTTTA TATAGATCGA ATTGAATTTG TTCCGGCAGA AGTAACCTTT     360

GAGGCAGAAT ATGATTTAGA AAGAGCACAR AAGGCGGTGG CGAGCTTGTT TAC           413
```

(2) INFORMATION FOR SEQ ID NO: 39:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 39:

```
Pro Gly Phe Thr Gly Gly Asp Ile Leu Arg Arg Thr Gly Val Gly Thr
1               5                   10                  15

Phe Gly Thr Ile Arg Val Arg Thr Thr Ala Pro Leu Thr Gln Arg Tyr
            20                  25                  30

Arg Ile Arg Phe Arg Phe Ala Ser Thr Thr Asn Leu Phe Ile Gly Ile
        35                  40                  45

Arg Val Gly Asp Arg Gln Val Asn Tyr Phe Asp Phe Gly Arg Thr Met
    50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
                85                  90                  95

Ala Asn Ala Phe Ser Ala Gly Gln Glu Val Tyr Phe Asp Arg Ile Glu
            100                 105                 110

Ile Ile Pro Val Asn Pro Ala Arg Glu Ala Lys Glu Asp Leu Glu Ala
        115                 120                 125

Ala Lys Lys Ala Val Ala Ser Leu Phe
    130                 135
```

(2) INFORMATION FOR SEQ ID NO: 40:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

| | | | | | |
|---|---|---|---|---|---|
| CCAGGTTTTA | CAGGAGGGGA | TATACTCCGA | AGAACAGGGG | TTGGTACATT | TGGAACAATA | 60 |
| AGGGTAAGGA | CTACTGCCCC | CTTAACACAA | AGATATCGCA | TAAGATTCCG | TTTCGCTTCT | 120 |
| ACCACAAATT | TGTTCATTGG | TATAAGAGTT | GGTGATAGAC | AAGTAAATTA | TTTTGACTTC | 180 |
| GGAAGAACAA | TGAACAGAGG | AGATGAATTA | AGGTACGAAT | CTTTTGCTAC | AAGGGAGTTT | 240 |
| ACTACTGATT | TTAATTTTAG | ACAACCTCAA | GAATTAATCT | CAGTGTTTGC | AAATGCATTT | 300 |
| AGCGCTGGTC | AAGAAGTTTA | TTTTGATAGA | ATTGAGATTA | TCCCCGTTAA | TCCCGCACGA | 360 |
| GAGGCGAAAG | AGGATCTAGA | AGCAGCAAAG | AAAGCGGTGG | CGAGCTTGTT | TAC | 413 |

(2) INFORMATION FOR SEQ ID NO: 41:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 41:

Pro Gly Phe Thr Gly Gly Asp Ile Leu Arg Arg Thr Asn Ala Gly Asn
1               5                   10                  15

Phe Gly Asp Met Arg Val Asn Ile Thr Ala Pro Leu Ser Gln Arg Tyr
            20                  25                  30

Arg Val Arg Ile Arg Tyr Ala Ser Thr Ala Asn Leu Gln Phe His Thr
        35                  40                  45

Ser Ile Asn Gly Arg Ala Ile Asn Gln Ala Asn Phe Pro Ala Thr Met
    50                  55                  60

Asn Ser Gly Glu Asn Leu Gln Ser Gly Ser Phe Arg Val Ala Gly Phe
65                  70                  75                  80

Thr Thr Pro Phe Thr Phe Ser Asp Ala Leu Ser Thr Phe Thr Ile Gly
            85                  90                  95

Ala Phe Ser Phe Ser Ser Asn Asn Glu Val Tyr Ile Asp Arg Ile Glu
        100                 105                 110

Phe Val Pro Ala Glu Val Thr Phe Ala Thr Glu Ser Asp Gln Asp Arg
    115                 120                 125

Ala Gln Lys Ala Val Ala Ser Leu Phe
130                 135

(2) INFORMATION FOR SEQ ID NO: 42:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

| | | | | | |
|---|---|---|---|---|---|
| CCAGGWTTTA | CAGGAGGGGA | TATCCTTCGA | AGAACGAATG | CTGGTAACTT | TGGAGATATG | 60 |
| CGTGTAAACA | TTACTGCACC | ACTATCACAA | AGATATCGCG | TAAGGATTCG | TTATGCTTCT | 120 |
| ACTGCAAATT | TACAATTCCA | TACATCAATT | AACGGAAGAG | CCATTAATCA | GGCGAATTTC | 180 |
| CCAGCAACTA | TGAACAGTGG | GGAGAATTTA | CAGTCCGGAA | GCTTCAGGGT | TGCAGGTTTT | 240 |

```
ACTACTCCAT TTACCTTTTC AGATGCACTA AGCACATTCA CAATAGGTGC TTTTAGCTTC      300

TCTTCAAACA ACGAAGTTTA TATAGATCGA ATTGAATTTG TTCCGGCAGA AGTAACATTT      360

GCAACAGAAT CTGATCAGGA TAGAGCACAA AAGGCGGTGG CGAGCTTGTT TAC            413

(2) INFORMATION FOR SEQ ID NO: 43:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 43:

Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
    50                  55                  60

Leu Gly Glu Asp Leu Arg Tyr Gly Ser Phe Ala Ile Arg Glu Phe Asn
65              70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Glu Asp Leu Xaa Ala Ala
        115                 120                 125

Lys Lys Ala Val Ala Ser Leu Phe
    130                 135

(2) INFORMATION FOR SEQ ID NO: 44:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

CCAGGATTTA TAGGAGGAGC TCTACTTCAA AGGACTGACC ATGGTTCGCT TGGAGTATTG       60

AGGGTCCAAT TTCCACTTCA CTTAAGACAA CAATATCGTA TTAGAGTCCG TTATGCTTCT      120

ACAACAAATA TTCGATTGAG TGTGAATGGC AGTTTCGGTA CTATTTCTCA AAATCTCCCT      180

AGTACAATGA GATTAGGAGA GGATTTAAGA TACGGATCTT TTGCTATAAG AGAGTTTAAT      240

ACTTCTATTA GACCCACTGC AAGTCCGGAC CAAATTCGAT TGACAATAGA ACCATCTTTT      300

ATTAGACAAG AGGTCTATGT AGATAGAATT GAGTTCATTC CAGTTAATCC GACGCGAGAG      360

GCGAAAGAGG ATCTAKAAGC AGCAAAAAAA GCGGTGGCGA GCTTGTTTAC                 410

(2) INFORMATION FOR SEQ ID NO: 45:

(i) SEQUENCE CHARACTERISTICS:
        (A) LENGTH: 137 amino acids
        (B) TYPE: amino acid
```

(C) STRANDEDNESS: single
(D) TOPOLOGY: linear (ii) MOLECULE TYPE: protein (xi) SEQUENCE DESCRIPTION: SEQ ID NO: 45:

Gln Xaa Leu Ser Gly Gly Asp Val Ile Arg Arg Thr Asn Thr Gly Gly
1               5                   10                  15

Phe Gly Ala Ile Arg Val Ser Val Thr Gly Pro Leu Thr Gln Arg Tyr
                20                  25                  30

Arg Ile Arg Phe Arg Tyr Ala Ser Thr Ile Asp Phe Asp Phe Phe Val
            35                  40                  45

Thr Arg Gly Gly Thr Thr Ile Asn Asn Phe Arg Phe Thr Arg Thr Met
    50                  55                  60

Asn Arg Gly Gln Glu Ser Arg Tyr Glu Ser Tyr Arg Thr Val Glu Phe
65              70                  75                  80

Thr Thr Pro Phe Asn Phe Thr Gln Ser Gln Asp Ile Ile Arg Thr Ser
                85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Glu Asp Leu Glu Ala
        115                 120                 125

Ala Lys Lys Ala Val Ala Ser Leu Phe
    130                 135

(2) INFORMATION FOR SEQ ID NO: 46:

(i) SEQUENCE CHARACTERISTICS:
        (A) LENGTH: 414 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

CCAGGWTTTA TCAGGAGGAG ATGTAATCCG AAGAACAAAT ACTGGTGGAT TCGGAGCAAT     60

AAGGGTGTCG GTCACTGGAC CGCTAACACA ACGATATCGC ATAAGGTTCC GTTATGCTTC    120

GACAATAGAT TTTGATTTCT TGTAACACG TGGAGGAACT ACTATAAATA ATTTTAGATT     180

TACACGTACA ATGAACAGGG GACAGGAATC AAGATATGAA TCCTATCGTA CTGTAGAGTT    240

TACAACTCCT TTTAACTTTA CACAAAGTCA AGATATAATT CGAACATCTA TCCAGGGACT    300

TAGTGGAAAT GGGGAAGTAT ACCTTGATAG AATTGAAATC ATCCCTGTAA ATCCAACACG    360

AGAAGCGGAA GARGATTTAG AAGCGGCGAA GAAAGCGGTG GCGAGCTTGT TTAC          414

(2) INFORMATION FOR SEQ ID NO: 47:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:

Pro Gly Phe Thr Gly Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
                20                  25                  30

```
Arg Val Arg Val Arg Phe Ala Ser Ser Gly Asn Phe Ser Ile Arg Ile
            35                  40                  45

Leu Arg Gly Asn Thr Ser Ile Ala Tyr Gln Arg Phe Gly Ser Thr Met
50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
            100                 105                 110

Ile Asp Arg Ile Glu Ile Ile Pro Val Asn Pro Ala Arg Glu Ala Glu
            115                 120                 125

Glu Asp Leu Glu Ala Ala Lys Lys Ala Val Ala Ser Leu Phe
130                 135                 140

(2) INFORMATION FOR SEQ ID NO: 48:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

CCAGGWTTTA CAGGAGGGGG TATACTCCGA AGAACAACTA ATGGCACATT TGGAACGTTA         60

AGAGTAACAG TTAATTCACC ATTAACACAA AGATATCGCG TAAGAGTTCG TTTTGCTTCA        120

TCAGGAAATT TCAGCATAAG GATACTGCGT GGAAATACCT CTATAGCTTA TCAAAGATTT        180

GGGAGTACAA TGAACAGAGG ACAGGAACTA ACTTACGAAT CATTTGTCAC AAGTGAGTTC        240

ACTACTAATC AGAGCGATCT GCCTTTTACA TTTACAAAG CTCAAGAAAA TTTAACAATC         300

CTTGCAGAAG GTGTTAGCAC CGGTAGTGAA TATTTTATAG ATAGAATTGA AATCATCCCT        360

GTGAACCCGG CACGAGAAGC AGAAGAGGAT TTAGAAGCAG CGAAGAAAGC GGTGGCGAGC        420

TTGTTTAC                                                                428

(2) INFORMATION FOR SEQ ID NO: 49:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 49:

Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
            35                  40                  45

Asn Gly Ser Phe Gly Thr Ile Ser Gln Asn Leu Pro Ser Thr Met Arg
            50                  55                  60

Leu Gly Glu Asp Leu Arg Tyr Gly Ser Phe Ala Ile Arg Glu Phe Asn
65                  70                  75                  80
```

```
Thr Ser Ile Arg Pro Thr Ala Ser Pro Asp Gln Ile Arg Leu Thr Ile
            85                  90                  95

Glu Pro Ser Phe Ile Arg Gln Glu Val Tyr Val Asp Arg Ile Glu Phe
           100                 105                 110

Ile Pro Val Asn Pro Thr Arg Glu Ala Lys Glu Asp Leu Glu Ala Ala
           115                 120                 125

Lys Lys Ala Val Ala Ser Leu Phe
       130                 135

(2) INFORMATION FOR SEQ ID NO: 50:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 50:

CCAGGWTTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT    120

ACAACAAATA TTCGATTGAG TGTGAATGGC AGTTTCGGTA CTATTTCTCA AAATCTCCCT    180

AGTACAATGA GATTAGGAGA GGATTTAAGA TACGGATCTT TTGCTATAAG AGAGTTTAAT    240

ACTTCTATTA GACCCACTGC AAGTCCGGAC CAAATTCGAT TGACAATAGA ACCATCTTTT    300

ATTAGACAAG AGGTCTATGT AGATAGAATT GAGTTCATTC CAGTTAATCC GACGCGAGAG    360

GCGAAAGAGG ATCTAGAAGC AGCAAAAAAA GCGGTGGCGA GCTTGTTTAC                410

(2) INFORMATION FOR SEQ ID NO: 51:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 51:

Pro Gly Phe Thr Gly Gly Asp Ile Leu Arg Arg Thr Gly Val Gly Thr
1               5                   10                  15

Phe Gly Thr Ile Arg Val Arg Thr Thr Ala Pro Leu Thr Gln Arg Tyr
            20                  25                  30

Arg Ile Arg Phe Arg Phe Ala Ser Thr Thr Asn Leu Phe Ile Gly Ile
        35                  40                  45

Arg Val Gly Asp Arg Gln Val Asn Tyr Phe Asp Phe Gly Arg Thr Met
    50                  55                  60

Asn Arg Gly Asp Glu Leu Arg Tyr Glu Ser Phe Ala Thr Arg Glu Phe
65                  70                  75                  80

Thr Thr Asp Phe Asn Phe Arg Gln Pro Gln Glu Leu Ile Ser Val Phe
            85                  90                  95

Ala Asn Ala Phe Ser Ala Gly Gln Glu Val Tyr Phe Asp Arg Ile Glu
           100                 105                 110

Ile Ile Pro Val Asn Pro Ala Arg Glu Ala Lys Glu Asp Leu Glu Ala
           115                 120                 125

Ala Lys Lys Ala Val Ala Ser Leu Phe
       130                 135
```

(2) INFORMATION FOR SEQ ID NO: 52:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

```
CCAGGTTTTA CAGGAGGGGA TATACTCCGA AGAACAGGGG TTGGTACATT TGGAACAATA      60

AGGGTAAGGA CTACTGCCCC CTTAACACAA AGATATCGCA TAAGATTCCG TTTCGCTTCT     120

ACCACAAATT TGTTCATTGG TATAAGAGTT GGTGATAGAC AAGTAAATTA TTTTGACTTC     180

GGAAGAACAA TGAACAGAGG AGATGAATTA AGGTACGAAT CTTTTGCTAC AAGGGAGTTT     240

ACTACTGATT TTAATTTTAG ACAACCTCAA GAATTAATCT CAGTGTTTGC AAATGCATTT     300

AGCGCTGGTC AAGAAGTTTA TTTTGATAGA ATTGAGATTA TCCCCGTTAA TCCCGCACGA     360

GAGGCGAAAG AGGATCTAGA AGCAGCAAAG AAAGCGGTGG CGAGCTTGTT TA             412
```

(2) INFORMATION FOR SEQ ID NO: 53:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 53:

```
Pro Gly Phe Thr Gly Gly Asp Val Ile Arg Arg Thr Asn Thr Gly Gly
1               5                   10                  15

Phe Gly Ala Ile Arg Val Ser Val Thr Gly Pro Leu Thr Gln Arg Tyr
            20                  25                  30

Arg Ile Arg Phe Arg Tyr Ala Ser Thr Ile Asp Phe Asp Phe Phe Val
        35                  40                  45

Thr Arg Gly Gly Thr Thr Ile Asn Asn Phe Arg Phe Thr Arg Thr Met
    50                  55                  60

Asn Arg Gly Gln Glu Ser Arg Tyr Glu Ser Tyr Arg Thr Val Glu Phe
65                  70                  75                  80

Thr Thr Pro Phe Asn Phe Thr Gln Ser Gln Asp Ile Ile Arg Thr Ser
                85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Glu Asp Xaa Glu Ala
        115                 120                 125

Ala Lys Lys Ala Val Ala Ser Leu Phe
    130                 135
```

(2) INFORMATION FOR SEQ ID NO: 54:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

```
CCAGGATTTA CAGGAGGAGA TGTAATCCGA AGAACAAATA CTGGTGGATT CGGAGCAATA      60

AGGGTGTCGG TCACTGGACC GCTAACACAA CGATATCGCA TAAGGTTCCG TTATGCTTCG     120

ACAATAGATT TTGATTTCTT TGTAACACGT GGAGGAACTA CTATAAATAA TTTTAGATTT     180

ACACGTACAA TGAACAGGGG ACAGGAATCA AGATATGAAT CCTATCGTAC TGTAGAGTTT     240

ACAACTCCTT TTAACTTTAC ACAAAGTCAA GATATAATTC GAACATCTAT CCAGGGACTT     300

AGTGGAAATG GGAAGTATA CCTTGATAGA ATTGAAATCA TCCCTGTAAA TCCAACACGA      360

GAAGCGGAAG AGGATTTWGA AGCGGCGAAG AAAGCGGTGG CGAGCTTGTT TAC           413
```

(2) INFORMATION FOR SEQ ID NO: 55:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 55:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30

Arg Ile Arg Val Arg Tyr Ala Ser Thr Thr Asn Ile Arg Leu Ser Val
        35                  40                  45

Asn Gly Ser Phe Gly Thr Ile Ser Gln Asn Leu Pro Ser Thr Met Arg
50                  55                  60

Leu Gly Glu Asp Leu Arg Tyr Gly Ser Phe Ala Ile Arg Glu Phe Asn
65                  70                  75                  80

Thr Ser Ile Arg Pro Thr Ala Ser Pro Asp Gln Ile Arg Leu Thr Ile
                85                  90                  95

Glu Pro Ser Phe Ile Arg Gln Glu Val Tyr Val Asp Arg Ile Glu Phe
            100                 105                 110

Ile Pro Val Asn Pro Thr Arg Glu Ala Lys Xaa Asp Leu Xaa Ala Ala
        115                 120                 125

Lys Lys Ala Val Ala Ser Leu Phe
130                 135
```

(2) INFORMATION FOR SEQ ID NO: 56:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

```
CCAGGATTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT     120

ACAACAAATA TTCGATTGAG TGTGAATGGC AGTTTCGGTA CTATTTCTCA AAATCTCCCT     180

AGTACAATGA GATTAGGAGA GGATTTAAGA TACGGATCTT TTGCTATAAG AGAGTTTAAT     240

ACTTCTATTA GACCCACTGC AAGTCCGGAC CAAATTCGAT TGACAATAGA ACCATCTTTT     300

ATTAGACAAG AGGTCTATGT AGATAGAATT GAGTTCATTC CAGTTAATCC GACGCGAGAG     360
```

```
GCGAAAGAKG ATCTABAAGC AGCAAAAAAA GCGGTGGCGA GCTTGTTTAC              410
```

(2) INFORMATION FOR SEQ ID NO: 57:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 57:

```
Pro Gly Phe Thr Gly Gly Asp Val Ile Arg Arg Thr Asn Thr Gly Gly
1               5                   10                  15

Phe Gly Ala Ile Arg Val Ser Val Thr Gly Pro Leu Thr Gln Arg Tyr
            20                  25                  30

Arg Ile Arg Phe Arg Tyr Ala Ser Thr Ile Asp Phe Asp Phe Phe Val
        35                  40                  45

Thr Arg Gly Gly Thr Thr Ile Asn Asn Phe Arg Phe Thr Arg Thr Met
50                  55                  60

Asn Arg Gly Gln Glu Ser Arg Tyr Glu Ser Tyr Arg Thr Val Glu Phe
65                  70                  75                  80

Thr Thr Pro Phe Asn Phe Thr Gln Ser Gln Asp Ile Ile Arg Thr Ser
                85                  90                  95

Ile Gln Gly Leu Ser Gly Asn Gly Glu Val Tyr Leu Asp Arg Ile Glu
            100                 105                 110

Ile Ile Pro Val Asn Pro Thr Arg Glu Ala Glu Glu Asp Leu Glu Ala
        115                 120                 125

Ala Lys Lys Ala Val Ala Ser Leu Phe
    130                 135
```

(2) INFORMATION FOR SEQ ID NO: 58:

(i) SEQUENCE CHARACTERISTICS:
        (A) LENGTH: 413 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

```
CCAGGWTTTA CAGGAGGAGA TGTAATCCGA AGAACAAATA CTGGTGGATT CGGAGCAATA     60

AGGGTGTCGG TCACTGGACC GCTAACACAA CGATATCGCA TAAGGTTCCG TTATGCTTCG    120

ACAATAGATT TTGATTTCTT TGTAACACGT GGAGGAACTA CTATAAATAA TTTTAGATTT    180

ACACGTACAA TGAACAGGGG ACAGGAATCA AGATATGAAT CCTATCGTAC TGTAGAGTTT    240

ACAACTCCTT TTAACTTTAC ACAAAGTCAA GATATAATTC GAACATCTAT CCAGGGACTT    300

AGTGGAAATG GGAAGTATA CCTTGATAGA ATTGAAATCA TCCCTGTAAA TCCAACACGA    360

GAAGCGGAAG AGGATTTAGA AGCGGCGAAG AAAGCGGTGG CGAGCTTGTT TAC          413
```

(2) INFORMATION FOR SEQ ID NO: 59:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 59:

```
Pro Gly Phe Xaa Gly Gly Gly Ile Leu Arg Arg Thr Thr Asn Gly Thr
1               5                   10                  15

Phe Gly Thr Leu Arg Val Thr Val Asn Ser Pro Leu Thr Gln Arg Tyr
            20                  25                  30

Arg Val Arg Val Arg Phe Ala Ser Ser Gly Asn Phe Ser Ile Arg Ile
        35                  40                  45

Leu Arg Gly Asn Thr Ser Ile Ala Tyr Gln Arg Phe Gly Ser Thr Met
    50                  55                  60

Asn Arg Gly Gln Glu Leu Thr Tyr Glu Ser Phe Val Thr Ser Glu Phe
65                  70                  75                  80

Thr Thr Asn Gln Ser Asp Leu Pro Phe Thr Phe Thr Gln Ala Gln Glu
                85                  90                  95

Asn Leu Thr Ile Leu Ala Glu Gly Val Ser Thr Gly Ser Glu Tyr Phe
            100                 105                 110

Ile Asp Arg Ile Glu Ile Ile Pro Val Asn Pro Ala Arg Glu Ala Glu
        115                 120                 125

Glu Asp Leu Glu Ala Ala Lys Lys Ala Val Ala Ser Leu Phe
    130                 135                 140
```

(2) INFORMATION FOR SEQ ID NO: 60:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

```
CCAGGWTTTA YAGGAGGGGG TATACTCCGA AGAACAACTA ATGGCACATT TGGAACGTTA      60

AGAGTAACAG TTAATTCACC ATTAACACAA AGATATCGCG TAAGAGTTCG TTTTGCTTCA     120

TCAGGAAATT TCAGCATAAG GATACTGCGT GGAAATACCT CTATAGCTTA TCAAAGATTT     180

GGGAGTACAA TGAACAGAGG ACAGGAACTA ACTTACGAAT CATTTGTCAC AAGTGAGTTC     240

ACTACTAATC AGAGCGATCT GCCTTTTACA TTTACACAAG CTCAAGAAAA TTTAACAATC     300

CTTGCAGAAG GTGTTAGCAC CGGTAGTGAA TATTTTATAG ATAGAATTGA AATCATCCCT     360

GTGAACCCGG CACGAGAAGC AGAAGAGGAT TTAGAAGCAG CGAAGAAAGC GGTGGCGAGC     420

TTGTTTAC                                                             428
```

(2) INFORMATION FOR SEQ ID NO: 61:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 61:

```
Pro Gly Phe Ile Gly Gly Ala Leu Leu Gln Arg Thr Asp His Gly Ser
1               5                   10                  15

Leu Gly Val Leu Arg Val Gln Phe Pro Leu His Leu Arg Gln Gln Tyr
            20                  25                  30
```

```
Arg Ile Arg Val Arg Tyr Ala Ser Thr Thr Asn Ile Arg Leu Ser Val
         35                  40                  45

Asn Gly Ser Phe Gly Thr Ile Ser Gln Asn Leu Pro Ser Thr Met Arg
     50                  55                  60

Leu Gly Glu Asp Leu Arg Tyr Gly Ser Phe Ala Ile Arg Glu Phe Asn
 65              70                  75                      80

Thr Ser Ile Arg Pro Thr Ala Ser Pro Asp Gln Ile Arg Leu Thr Ile
             85                  90                  95

Glu Pro Ser Phe Ile Arg Gln Glu Val Tyr Val Asp Arg Ile Glu Phe
                100                 105                 110

Ile Pro Val Asn Pro Thr Arg Glu Ala Lys Glu Asp Leu Glu Ala Ala
            115                 120                 125

Lys Lys Ala Val Ala Ser Leu Phe
        130                 135
```

(2) INFORMATION FOR SEQ ID NO: 62:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

```
CCAGGTTTTA TAGGAGGAGC TCTACTTCAA AGGACTGACC ATGGTTCGCT TGGAGTATTG      60

AGGGTCCAAT TTCCACTTCA CTTAAGACAA CAATATCGTA TTAGAGTCCG TTATGCTTCT     120

ACAACAAATA TTCGATTGAG TGTGAATGGC AGTTTCGGTA CTATTTCTCA AAATCTCCCT     180

AGTACAATGA GATTAGGAGA GGATTTAAGA TACGGATCTT TTGCTATAAG AGAGTTTAAT     240

ACTTCTATTA GACCCACTGC AAGTCCGGAC CAAATTCGAT TGACAATAGA ACCATCTTTT     300

ATTAGACAAG AGGTCTATGT AGATAGAATT GAGTTCATTC CAGTTAATCC GACGCGAGAG     360

GCGAAAGAGG ATCTAGAAGC AGCAAAAAAA GCGGTGGCGA GCTTGTTTAC                410
```

(2) INFORMATION FOR SEQ ID NO: 63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

```
GTTCATTGGT ATAAGAGTTG GTG                                             23
```

(2) INFORMATION FOR SEQ ID NO: 64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

```
CCACTGCAAG TCCGGACCAA ATTCG                                           25
```

(2) INFORMATION FOR SEQ ID NO: 65:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 65:

GAATATATTC CCGTCYATCT CTGG                                              24

(2) INFORMATION FOR SEQ ID NO: 66:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 66:

GCACGAATTA CTGTAGCGAT AGG                                               23

(2) INFORMATION FOR SEQ ID NO: 67:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 67:

GCTGGTAACT TTGGAGATAT GCGTG                                             25

(2) INFORMATION FOR SEQ ID NO: 68:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 68:

GATTTCTTTG TAACACGTGG AGG                                               23

(2) INFORMATION FOR SEQ ID NO: 69:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 69:

CACTACTAAT CAGAGCGATC TG                                                22

(2) INFORMATION FOR SEQ ID NO: 70:

(i) SEQUENCE CHARACTERISTICS:
          (A) LENGTH: 1156 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 70:

```
Met Asn Gln Asn Lys His Gly Ile Ile Gly Ala Ser Asn Cys Gly Cys
1               5                  10                  15

Ala Ser Asp Asp Val Ala Lys Tyr Pro Leu Ala Asn Asn Pro Tyr Ser
            20                  25                  30

Ser Ala Leu Asn Leu Asn Ser Cys Gln Asn Ser Ser Ile Leu Asn Trp
        35                  40                  45

Ile Asn Ile Ile Gly Asp Ala Ala Lys Glu Ala Val Ser Ile Gly Thr
50                  55                  60

Thr Ile Val Ser Leu Ile Thr Ala Pro Ser Leu Thr Gly Leu Ile Ser
65                  70                  75                  80

Ile Val Tyr Asp Leu Ile Gly Lys Val Leu Gly Gly Ser Ser Gly Gln
                85                  90                  95

Ser Ile Ser Asp Leu Ser Ile Cys Asp Leu Leu Ser Ile Ile Asp Leu
            100                 105                 110

Arg Val Ser Gln Ser Val Leu Asn Asp Gly Ile Ala Asp Phe Asn Gly
        115                 120                 125

Ser Val Leu Leu Tyr Arg Asn Tyr Leu Glu Ala Leu Asp Ser Trp Asn
130                 135                 140

Lys Asn Pro Asn Ser Ala Ser Ala Glu Glu Leu Arg Thr Arg Phe Arg
145                 150                 155                 160

Ile Ala Asp Ser Glu Phe Asp Arg Ile Leu Thr Arg Gly Ser Leu Thr
                165                 170                 175

Asn Gly Gly Ser Leu Ala Arg Gln Asn Ala Gln Ile Leu Leu Leu Pro
            180                 185                 190

Ser Phe Ala Ser Ala Ala Phe His Leu Leu Leu Arg Asp Ala
        195                 200                 205

Thr Arg Tyr Gly Thr Asn Trp Gly Leu Tyr Asn Ala Thr Pro Phe Ile
210                 215                 220

Asn Tyr Gln Ser Lys Leu Val Glu Leu Ile Glu Leu Tyr Thr Asp Tyr
225                 230                 235                 240

Cys Val His Trp Tyr Asn Arg Gly Phe Asn Glu Leu Arg Gln Arg Gly
                245                 250                 255

Thr Ser Ala Thr Ala Trp Leu Glu Phe His Arg Tyr Arg Arg Glu Met
            260                 265                 270

Thr Leu Met Val Leu Asp Ile Val Ala Ser Phe Ser Ser Leu Asp Ile
        275                 280                 285

Thr Asn Tyr Pro Ile Glu Thr Asp Phe Gln Leu Ser Arg Val Ile Tyr
290                 295                 300

Thr Asp Pro Ile Gly Phe Val His Arg Ser Leu Arg Gly Glu Ser
305                 310                 315                 320

Trp Phe Ser Phe Val Asn Arg Ala Asn Phe Ser Asp Leu Glu Asn Ala
                325                 330                 335

Ile Pro Asn Pro Arg Pro Ser Trp Phe Leu Asn Asn Met Ile Ile Ser
            340                 345                 350

Thr Gly Ser Leu Thr Leu Pro Val Ser Pro Ser Thr Asp Arg Ala Arg
        355                 360                 365

Val Trp Tyr Gly Ser Arg Asp Arg Ile Ser Pro Ala Asn Ser Gln Phe
370                 375                 380
```

-continued

```
Ile Thr Glu Leu Ile Ser Gly Gln His Thr Thr Ala Thr Gln Thr Ile
385                 390                 395                 400

Leu Gly Arg Asn Ile Phe Arg Val Asp Ser Gln Ala Cys Asn Leu Asn
            405                 410                 415

Asp Thr Thr Tyr Gly Val Asn Arg Ala Val Phe Tyr His Asp Ala Ser
        420                 425                 430

Glu Gly Ser Gln Arg Ser Val Tyr Glu Gly Tyr Ile Arg Thr Thr Gly
    435                 440                 445

Ile Asp Asn Pro Arg Val Gln Asn Ile Asn Thr Tyr Leu Pro Gly Glu
450                 455                 460

Asn Ser Asp Ile Pro Thr Pro Glu Asp Tyr Thr His Ile Leu Ser Thr
465                 470                 475                 480

Thr Ile Asn Leu Thr Gly Gly Leu Arg Gln Val Ala Ser Asn Arg Arg
            485                 490                 495

Ser Ser Leu Val Met Tyr Gly Trp Thr His Lys Ser Leu Ala Arg Asn
        500                 505                 510

Asn Thr Ile Asn Pro Asp Arg Ile Thr Gln Ile Pro Leu Thr Lys Val
    515                 520                 525

Asp Thr Arg Gly Thr Gly Val Ser Tyr Val Asn Asp Pro Gly Phe Ile
530                 535                 540

Gly Gly Ala Leu Leu Gln Arg Thr Asp His Gly Ser Leu Gly Val Leu
545                 550                 555                 560

Arg Val Gln Phe Pro Leu His Leu Arg Gln Gln Tyr Arg Ile Arg Val
            565                 570                 575

Arg Tyr Ala Ser Thr Thr Asn Ile Arg Leu Ser Val Asn Gly Ser Phe
        580                 585                 590

Gly Thr Ile Ser Gln Asn Leu Pro Ser Thr Met Arg Leu Gly Glu Asp
    595                 600                 605

Leu Arg Tyr Gly Ser Phe Ala Ile Arg Glu Phe Asn Thr Ser Ile Arg
610                 615                 620

Pro Thr Ala Ser Pro Asp Gln Ile Arg Leu Thr Ile Glu Pro Ser Phe
625                 630                 635                 640

Ile Arg Gln Glu Val Tyr Val Asp Arg Ile Glu Phe Ile Pro Val Asn
            645                 650                 655

Pro Thr Arg Glu Ala Lys Glu Asp Leu Glu Ala Ala Lys Lys Ala Val
        660                 665                 670

Ala Ser Leu Phe Thr Arg Thr Arg Asp Gly Leu Gln Val Asn Val Lys
    675                 680                 685

Asp Tyr Gln Val Asp Gln Ala Ala Asn Leu Val Ser Cys Leu Ser Asp
690                 695                 700

Glu Gln Tyr Gly Tyr Asp Lys Lys Met Leu Leu Glu Ala Val Arg Ala
705                 710                 715                 720

Ala Lys Arg Leu Ser Arg Glu Arg Asn Leu Leu Gln Asp Pro Asp Phe
            725                 730                 735

Asn Thr Ile Asn Ser Thr Glu Glu Asn Gly Trp Lys Ala Ser Asn Gly
        740                 745                 750

Val Thr Ile Ser Glu Gly Gly Pro Phe Tyr Lys Gly Arg Ala Ile Gln
    755                 760                 765

Leu Ala Ser Ala Arg Glu Asn Tyr Pro Thr Tyr Ile Tyr Gln Lys Val
770                 775                 780

Asp Ala Ser Glu Leu Lys Pro Tyr Thr Arg Tyr Arg Leu Asp Gly Phe
785                 790                 795                 800
```

-continued

```
Val Lys Ser Ser Gln Asp Leu Glu Ile Asp Leu Ile His His His Lys
                805                 810                 815
Val His Leu Val Lys Asn Val Pro Asp Asn Leu Val Ser Asp Thr Tyr
            820                 825                 830
Pro Asp Asp Ser Cys Ser Gly Ile Asn Arg Cys Gln Glu Gln Gln Met
            835                 840                 845
Val Asn Ala Gln Leu Glu Thr Glu His His His Pro Met Asp Cys Cys
850                 855                 860
Glu Ala Ala Gln Thr His Glu Phe Ser Ser Tyr Ile Asp Thr Gly Asp
865                 870                 875                 880
Leu Asn Ser Ser Val Asp Gln Gly Ile Trp Ala Ile Phe Lys Val Arg
                885                 890                 895
Thr Thr Asp Gly Tyr Ala Thr Leu Gly Asn Leu Glu Leu Val Glu Val
                900                 905                 910
Gly Pro Leu Ser Gly Glu Ser Leu Glu Arg Glu Gln Arg Asp Asn Thr
                915                 920                 925
Lys Trp Ser Ala Glu Leu Gly Arg Lys Arg Ala Glu Thr Asp Arg Val
            930                 935                 940
Tyr Gln Asp Ala Lys Gln Ser Ile Asn His Leu Phe Val Asp Tyr Gln
945                 950                 955                 960
Asp Gln Gln Leu Asn Pro Glu Ile Gly Met Ala Asp Ile Met Asp Ala
                965                 970                 975
Gln Asn Leu Val Ala Ser Ile Ser Asp Val Tyr Ser Asp Ala Val Leu
                980                 985                 990
Gln Ile Pro Gly Ile Asn Tyr Glu Ile Tyr Thr Glu Leu Ser Asn Arg
                995                 1000                1005
Leu Gln Gln Ala Ser Tyr Leu Tyr Thr Ser Arg Asn Ala Val Gln Asn
            1010                1015                1020
Gly Asp Phe Asn Asn Gly Leu Asp Ser Trp Asn Ala Thr Ala Gly Ala
1025                1030                1035                1040
Ser Val Gln Gln Asp Gly Asn Thr His Phe Leu Val Leu Ser His Trp
                1045                1050                1055
Asp Ala Gln Val Ser Gln Gln Phe Arg Val Gln Pro Asn Cys Lys Tyr
            1060                1065                1070
Val Leu Arg Val Thr Ala Glu Lys Val Gly Gly Gly Asp Gly Tyr Val
            1075                1080                1085
Thr Ile Arg Asp Asp Ala His His Thr Glu Thr Leu Thr Phe Asn Ala
            1090                1095                1100
Cys Asp Tyr Asp Ile Asn Gly Thr Tyr Val Thr Asp Asn Thr Tyr Leu
1105                1110                1115                1120
Thr Lys Glu Val Val Phe His Pro Glu Thr Gln His Met Trp Val Glu
                1125                1130                1135
Val Asn Glu Thr Glu Gly Ala Phe His Ile Asp Ser Ile Glu Phe Val
                1140                1145                1150
Glu Thr Glu Lys
        1155
```

(2) INFORMATION FOR SEQ ID NO: 71:

(i) SEQUENCE CHARACTERISTICS:
        (A) LENGTH: 3471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

```
ATGAATCAAA ATAAACACGG AATTATTGGC GCTTCCAATT GTGGTTGTGC ATCTGATGAT         60

GTTGCGAAAT ATCCTTTAGC CAACAATCCA TATTCATCTG CTTTAAATTT AAATTCTTGT        120

CAAAATAGTA GTATTCTCAA CTGGATTAAC ATAATAGGCG ATGCAGCAAA GAAGCAGTA         180

TCTATTGGGA CAACCATAGT CTCTCTTATC ACAGCACCTT CTCTTACTGG ATTAATTTCA        240

ATAGTATATG ACCTTATAGG TAAAGTACTA GGAGGTAGTA GTGGACAATC CATATCAGAT        300

TTGTCTATAT GTGACTTATT ATCTATTATT GATTTACGGG TAAGTCAGAG TGTTTTAAAT        360

GATGGGATTG CAGATTTTAA TGGTTCTGTA CTCTTATACA GGAACTATTT AGAGGCTCTG        420

GATAGCTGGA ATAAGAATCC TAATTCTGCT TCTGCTGAAG AACTCCGTAC TCGTTTTAGA        480

ATCGCCGACT CAGAATTTGA TAGAATTTTA ACCCGAGGGT CTTTAACGAA TGGTGGCTCG        540

TTAGCTAGAC AAAATGCCCA AATATTATTA TTACCTTCTT TTGCGAGCGC TGCATTTTTC        600

CATTTATTAC TACTAAGGGA TGCTACTAGA TATGGCACTA ATTGGGGCT ATACAATGCT         660

ACACCTTTTA TAAATTATCA ATCAAAACTA GTAGAGCTTA TTGAACTATA TACTGATTAT        720

TGCGTACATT GGTATAATCG AGGTTTCAAC GAACTAAGAC AACGAGGCAC TAGTGCTACA        780

GCTTGGTTAG AATTTCATAG ATATCGTAGA GAGATGACAT TGATGGTATT AGATATAGTA        840

GCATCATTTT CAAGTCTTGA TATTACTAAT TACCCAATAG AAACAGATTT TCAGTTGAGT        900

AGGGTCATTT ATACAGATCC AATTGGTTTT GTACATCGTA GTAGTCTTAG GGAGAAAGT        960

TGGTTTAGCT TTGTTAATAG AGCTAATTTC TCAGATTTAG AAAATGCAAT ACCTAATCCT       1020

AGACCGTCTT GGTTTTTAAA TAATATGATT ATATCTACTG GTTCACTTAC ATTGCCGGTT       1080

AGCCCAAGTA CTGATAGAGC GAGGGTATGG TATGGAAGTC GAGATCGAAT TTCCCCTGCT       1140

AATTCACAAT TTATTACTGA ACTAATCTCT GGACAACATA CGACTGCTAC ACAAACTATT       1200

TTAGGGCGAA ATATATTTAG AGTAGATTCT CAAGCTTGTA ATTTAAATGA TACCACATAT       1260

GGAGTGAATA GGGCGGTATT TTATCATGAT GCGAGTGAAG GTTCTCAAAG ATCCGTGTAC       1320

GAGGGGTATA TTCGAACAAC TGGGATAGAT AACCCTAGAG TTCAAAATAT TAACACTTAT       1380

TTACCTGGAG AAAATTCAGA TATCCCAACT CCAGAAGACT ATACTCATAT ATTAAGCACA       1440

ACAATAAATT TAACAGGAGG ACTTAGACAA GTAGCATCTA ATCGCCGTTC ATCTTTAGTA       1500

ATGTATGGTT GGACACATAA AAGTCTGGCT CGTAACAATA CCATTAATCC AGATAGAATT       1560

ACACAGATAC CATTGACGAA GGTTGATACC CGAGGCACAG GTGTTTCTTA TGTGAATGAT       1620

CCAGGATTTA TAGGAGGAGC TCTACTTCAA AGGACTGACC ATGGTTCGCT TGGAGTATTG       1680

AGGGTCCAAT TTCCACTTCA CTTAAGACAA CAATATCGTA TTAGAGTCCG TTATGCTTCT       1740

ACAACAAATA TTCGATTGAG TGTGAATGGC AGTTTCGGTA CTATTTCTCA AAATCTCCCT       1800

AGTACAATGA GATTAGGAGA GGATTTAAGA TACGGATCTT TTGCTATAAG AGAGTTTAAT       1860

ACTTCTATTA GACCCACTGC AAGTCCGGAC CAAATTCGAT TGACAATAGA ACCATCTTTT       1920

ATTAGACAAG AGGTCTATGT AGATAGAATT GAGTTCATTC CAGTTAATCC GACGCGAGAG       1980

GCGAAAGAGG ATCTAGAAGC AGCAAAAAAA GCGGTGGCGA GCTTGTTTAC ACGCACAAGG       2040

GACGGATTAC AAGTAAATGT GAAAGATTAT CAAGTCGATC AAGCGGCAAA TTTAGTGTCA       2100

TGCTTATCAG ATGAACAATA TGGGTATGAC AAAAAGATGT TATTGGAAGC GGTACGTGCG       2160

GCAAAACGAC TTAGCCGAGA ACGCAACTTA CTTCAGGATC CAGATTTTAA TACAATCAAT       2220

AGTACAGAAG AAAATGGATG GAAAGCAAGT AACGGCGTTA CTATTAGTGA GGGCGGGCCA       2280
```

```
TTCTATAAAG GCCGTGCAAT TCAGCTAGCA AGTGCACGAG AAAATTACCC AACATACATC    2340

TATCAAAAAG TAGATGCATC GGAGTTAAAG CCGTATACAC GTTATAGACT GGATGGGTTC    2400

GTGAAGAGTA GTCAAGATTT AGAAATTGAT CTCATTCACC ATCATAAAGT CCATCTTGTG    2460

AAAAATGTAC CAGATAATTT AGTATCTGAT ACTTACCCAG ATGATTCTTG TAGTGGAATC    2520

AATCGATGTC AGGAACAACA GATGGTAAAT GCGCAACTGG AAACAGAGCA TCATCATCCG    2580

ATGGATTGCT GTGAAGCAGC TCAAACACAT GAGTTTTCTT CCTATATTGA TACAGGGGAT    2640

TTAAATTCGA GTGTAGACCA GGGAATCTGG GCGATCTTTA AAGTTCGAAC AACCGATGGT    2700

TATGCGACGT TAGGAAATCT TGAATTGGTA GAGGTCGGAC CGTTATCGGG TGAATCTTTA    2760

GAACGTGAAC AAAGGGATAA TACAAAATGG AGTGCAGAGC TAGGAAGAAA GCGTGCAGAA    2820

ACAGATCGCG TGTATCAAGA TGCCAAACAA TCCATCAATC ATTTATTTGT GGATTATCAA    2880

GATCAACAAT TAAATCCAGA AATAGGGATG GCAGATATTA TGGACGCTCA AAATCTTGTC    2940

GCATCAATTT CAGATGTATA TAGCGATGCC GTACTGCAAA TCCCTGGAAT TAACTATGAG    3000

ATTTACACAG AGCTGTCCAA TCGCTTACAA CAAGCATCGT ATCTGTATAC GTCTCGAAAT    3060

GCGGTGCAAA ATGGGACTT TAACAACGGG CTAGATAGCT GGAATGCAAC AGCGGGTGCA    3120

TCGGTACAAC AGGATGGCAA TACGCATTTC TTAGTTCTTT CTCATTGGGA TGCACAAGTT    3180

TCTCAACAAT TTAGAGTGCA GCCGAATTGT AAATATGTAT TACGTGTAAC AGCAGAGAAA    3240

GTAGGCGGCG GAGACGGATA CGTGACTATC CGGGATGATG CTCATCATAC AGAAACGCTT    3300

ACATTTAATG CATGTGATTA TGATATAAAT GGCACGTACG TGACTGATAA TACGTATCTA    3360

ACAAAAGAAG TGGTATTCCA TCCGGAGACA CAACACATGT GGGTAGAGGT AAATGAAACA    3420

GAAGGTGCAT TCATATAGA TAGTATTGAA TTCGTTGAAA CAGAAAAGTA A              3471
```

(2) INFORMATION FOR SEQ ID NO: 72:

(i) SEQUENCE CHARACTERISTICS:
        (A) LENGTH: 1156 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 72:

```
Met Asn Arg Asn Asn Gln Asn Glu Tyr Glu Ile Ile Asp Ala Pro His
1               5                   10                  15

Cys Gly Cys Pro Ser Asp Asp Val Arg Tyr Pro Leu Ala Ser Asp
            20                  25                  30

Pro Asn Ala Ala Leu Gln Asn Met Asn Tyr Lys Asp Tyr Leu Gln Met
        35                  40                  45

Thr Asp Glu Asp Tyr Thr Asp Ser Tyr Ile Asn Pro Ser Leu Ser Ile
    50                  55                  60

Ser Gly Arg Asp Ala Val Gln Thr Ala Leu Thr Val Val Gly Arg Ile
65                  70                  75                  80

Leu Gly Ala Leu Gly Val Pro Phe Ser Gly Gln Ile Val Ser Phe Tyr
                85                  90                  95

Gln Phe Leu Leu Asn Thr Leu Trp Pro Val Asn Asp Thr Ala Ile Trp
            100                 105                 110

Glu Ala Phe Met Arg Gln Val Glu Glu Leu Val Asn Gln Gln Ile Thr
        115                 120                 125

Glu Phe Ala Arg Asn Gln Ala Leu Ala Arg Leu Gln Gly Leu Gly Asp
    130                 135                 140
```

```
Ser Phe Asn Val Tyr Gln Arg Ser Leu Gln Asn Trp Leu Ala Asp Arg
145                 150                 155                 160

Asn Asp Thr Arg Asn Leu Ser Val Val Arg Ala Gln Phe Ile Ala Leu
                165                 170                 175

Asp Leu Asp Phe Val Asn Ala Ile Pro Leu Phe Ala Val Asn Gly Gln
            180                 185                 190

Gln Val Pro Leu Leu Ser Val Tyr Ala Gln Ala Val Asn Leu His Leu
        195                 200                 205

Leu Leu Leu Lys Asp Ala Ser Leu Phe Gly Glu Gly Trp Gly Phe Thr
210                 215                 220

Gln Gly Glu Ile Ser Thr Tyr Tyr Asp Arg Gln Leu Glu Leu Thr Ala
225                 230                 235                 240

Lys Tyr Thr Asn Tyr Cys Glu Thr Trp Tyr Asn Thr Gly Leu Asp Arg
                245                 250                 255

Leu Arg Gly Thr Asn Thr Glu Ser Trp Leu Arg Tyr His Gln Phe Arg
            260                 265                 270

Arg Glu Met Thr Leu Val Val Leu Asp Val Val Ala Leu Phe Pro Tyr
        275                 280                 285

Tyr Asp Val Arg Leu Tyr Pro Thr Gly Ser Asn Pro Gln Leu Thr Arg
290                 295                 300

Glu Val Tyr Thr Asp Pro Ile Val Phe Asn Pro Pro Ala Asn Val Gly
305                 310                 315                 320

Leu Cys Arg Arg Trp Gly Thr Asn Pro Tyr Asn Thr Phe Ser Glu Leu
                325                 330                 335

Glu Asn Ala Phe Ile Arg Pro Pro His Leu Phe Asp Arg Leu Asn Ser
            340                 345                 350

Leu Thr Ile Ser Ser Asn Arg Phe Pro Val Ser Ser Asn Phe Met Asp
        355                 360                 365

Tyr Trp Ser Gly His Thr Leu Arg Arg Ser Tyr Leu Asn Asp Ser Ala
370                 375                 380

Val Gln Glu Asp Ser Tyr Gly Leu Ile Thr Thr Arg Ala Thr Ile
385                 390                 395                 400

Asn Pro Gly Val Asp Gly Thr Asn Arg Ile Glu Ser Thr Ala Val Asp
                405                 410                 415

Phe Arg Ser Ala Leu Ile Gly Ile Tyr Gly Val Asn Arg Ala Ser Phe
            420                 425                 430

Val Pro Gly Gly Leu Phe Asn Gly Thr Thr Ser Pro Ala Asn Gly Gly
        435                 440                 445

Cys Arg Asp Leu Tyr Asp Thr Asn Asp Glu Leu Pro Pro Asp Glu Ser
450                 455                 460

Thr Gly Ser Ser Thr His Arg Leu Ser His Val Thr Phe Phe Ser Phe
465                 470                 475                 480

Gln Thr Asn Gln Ala Gly Ser Ile Ala Asn Ala Gly Ser Val Pro Thr
                485                 490                 495

Tyr Val Trp Thr Arg Arg Asp Val Asp Leu Asn Asn Thr Ile Thr Pro
            500                 505                 510

Asn Arg Ile Thr Gln Leu Pro Leu Val Lys Ala Ser Ala Pro Val Ser
        515                 520                 525

Gly Thr Thr Val Leu Lys Gly Pro Gly Phe Thr Gly Gly Ile Leu
530                 535                 540

Arg Arg Thr Thr Asn Gly Thr Phe Gly Thr Leu Arg Val Thr Val Asn
545                 550                 555                 560
```

-continued

```
Ser Pro Leu Thr Gln Arg Tyr Arg Val Arg Val Arg Phe Ala Ser Ser
            565                 570                 575
Gly Asn Phe Ser Ile Arg Ile Leu Arg Gly Asn Thr Ser Ile Ala Tyr
            580                 585                 590
Gln Arg Phe Gly Ser Thr Met Asn Arg Gly Gln Glu Leu Thr Tyr Glu
            595                 600                 605
Ser Phe Val Thr Ser Glu Phe Thr Thr Asn Gln Ser Asp Leu Pro Phe
            610                 615                 620
Thr Phe Thr Gln Ala Gln Glu Asn Leu Thr Ile Leu Ala Glu Gly Val
625                 630                 635                 640
Ser Thr Gly Ser Glu Tyr Phe Ile Asp Arg Ile Glu Ile Ile Pro Val
            645                 650                 655
Asn Pro Ala Arg Glu Ala Glu Glu Asp Leu Glu Ala Ala Lys Lys Ala
            660                 665                 670
Val Ala Asn Leu Phe Thr Arg Thr Arg Asp Gly Leu Gln Val Asn Val
            675                 680                 685
Thr Asp Tyr Gln Val Asp Gln Ala Ala Asn Leu Val Ser Cys Leu Ser
            690                 695                 700
Asp Glu Gln Tyr Gly His Asp Lys Lys Met Leu Leu Glu Ala Val Arg
705                 710                 715                 720
Ala Ala Lys Arg Leu Ser Arg Glu Arg Asn Leu Leu Gln Asp Pro Asp
            725                 730                 735
Phe Asn Thr Ile Asn Ser Thr Glu Glu Asn Gly Trp Lys Ala Ser Asn
            740                 745                 750
Gly Val Thr Ile Ser Glu Gly Gly Pro Phe Phe Lys Gly Arg Ala Leu
            755                 760                 765
Gln Leu Ala Ser Ala Arg Glu Asn Tyr Pro Thr Tyr Ile Tyr Gln Lys
            770                 775                 780
Val Asp Ala Ser Val Leu Lys Pro Tyr Thr Arg Tyr Arg Leu Asp Gly
785                 790                 795                 800
Phe Val Lys Ser Ser Gln Asp Leu Glu Ile Asp Leu Ile His His His
            805                 810                 815
Lys Val His Leu Val Lys Asn Val Pro Asp Asn Leu Val Ser Asp Thr
            820                 825                 830
Tyr Ser Asp Gly Ser Cys Ser Gly Ile Asn Arg Cys Asp Glu Gln His
            835                 840                 845
Gln Val Asp Met Gln Leu Asp Ala Glu His His Pro Met Asp Cys Cys
850                 855                 860
Glu Ala Ala Gln Thr His Glu Phe Ser Ser Tyr Ile Asn Thr Gly Asp
865                 870                 875                 880
Leu Asn Ala Ser Val Asp Gln Gly Ile Trp Val Val Leu Lys Val Arg
            885                 890                 895
Thr Thr Asp Gly Tyr Ala Thr Leu Gly Asn Leu Glu Leu Val Glu Val
            900                 905                 910
Gly Pro Leu Ser Gly Glu Ser Leu Glu Arg Glu Gln Arg Asp Asn Ala
            915                 920                 925
Lys Trp Asn Ala Glu Leu Gly Arg Lys Arg Ala Glu Ile Asp Arg Val
            930                 935                 940
Tyr Leu Ala Ala Lys Gln Ala Ile Asn His Leu Phe Val Asp Tyr Gln
945                 950                 955                 960
Asp Gln Gln Leu Asn Pro Glu Ile Gly Leu Ala Glu Ile Asn Glu Ala
            965                 970                 975
Ser Asn Leu Val Glu Ser Ile Ser Gly Val Tyr Ser Asp Thr Leu Leu
```

-continued

```
                980             985             990
Gln Ile Pro Gly Ile Asn Tyr Glu Ile Tyr Thr Glu Leu Ser Asp Arg
        995                 1000                1005
Leu Gln Gln Ala Ser Tyr Leu Tyr Thr Ser Arg Asn Ala Val Gln Asn
    1010                1015                1020
Gly Asp Phe Asn Ser Gly Leu Asp Ser Trp Asn Thr Thr Met Asp Ala
1025                1030                1035                1040
Ser Val Gln Gln Asp Gly Asn Met His Phe Leu Val Leu Ser His Trp
                1045                1050                1055
Asp Ala Gln Val Ser Gln Leu Arg Val Asn Pro Asn Cys Lys Tyr
            1060                1065                1070
Val Leu Arg Val Thr Ala Arg Lys Val Gly Gly Gly Asp Gly Tyr Val
        1075                1080                1085
Thr Ile Arg Asp Gly Ala His His Gln Glu Thr Leu Thr Phe Asn Ala
    1090                1095                1100
Cys Asp Tyr Asp Val Asn Gly Thr Tyr Val Asn Asp Asn Ser Tyr Ile
1105                1110                1115                1120
Thr Glu Glu Val Val Phe Tyr Pro Glu Thr Lys His Met Trp Val Glu
                1125                1130                1135
Val Ser Glu Ser Glu Gly Ser Phe Tyr Ile Asp Ser Ile Glu Phe Ile
            1140                1145                1150
Glu Thr Gln Glu
        1155

(2) INFORMATION FOR SEQ ID NO: 73:

(i) SEQUENCE CHARACTERISTICS:
        (A) LENGTH: 3471 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

ATGAATCGAA ATAATCAAAA TGAATATGAA ATTATTGATG CCCCCCATTG TGGGTGTCCA      60

TCAGATGACG ATGTGAGGTA TCCTTTGGCA AGTGACCCAA ATGCAGCGTT ACAAAATATG     120

AACTATAAAG ATTACTTACA AATGACAGAT GAGGACTACA CTGATTCTTA TATAAATCCT     180

AGTTTATCTA TTAGTGGTAG AGATGCAGTT CAGACTGCGC TTACTGTTGT TGGGAGAATA     240

CTCGGGGCTT TAGGTGTTCC GTTTTCTGGA CAAATAGTGA GTTTTTATCA ATTCCTTTTA     300

AATACACTGT GGCCAGTTAA TGATACAGCT ATATGGGAAG CTTTCATGCG ACAGGTGGAG     360

GAACTTGTCA ATCAACAAAT AACAGAATTT GCAAGAAATC AGGCACTTGC AAGATTGCAA     420

GGATTAGGAG ACTCTTTTAA TGTATATCAA CGTTCCCTTC AAAATTGGTT GGCTGATCGA     480

AATGATACAC GAAATTTAAG TGTTGTTCGT GCTCAATTTA TAGCTTTAGA CCTTGATTTT     540

GTTAATGCTA TTCCATTGTT TGCAGTAAAT GGACAGCAGG TTCCATTACT GTCAGTATAT     600

GCACAAGCTG TGAATTTACA TTTGTTATTA TTAAAAGATG CATCTCTTTT TGGAGAAGGA     660

TGGGGATTCA CACAGGGGGA AATTTCCACA TATTATGACC GTCAATTGGA ACTAACCGCT     720

AAGTACACTA ATTACTGTGA AACTTGGTAT AATACAGGTT TAGATCGTTT AAGAGGAACA     780

AATACTGAAA GTTGGTTAAG ATATCATCAA TTCCGTAGAG AAATGACTTT AGTGGTATTA     840

GATGTTGTGG CGCTATTTCC ATATTATGAT GTACGACTTT ATCCAACGGG ATCAAACCCA     900

CAGCTTACAC GTGAGGTATA TACAGATCCG ATTGTATTTA ATCCACCAGC TAATGTTGGA     960
```

```
CTTTGCCGAC GTTGGGGTAC TAATCCCTAT AATACTTTTT CTGAGCTCGA AAATGCCTTC    1020

ATTCGCCCAC CACATCTTTT TGATAGGCTG AATAGCTTAA CAATCAGCAG TAATCGATTT    1080

CCAGTTTCAT CTAATTTTAT GGATTATTGG TCAGGACATA CGTTACGCCG TAGTTATCTG    1140

AACGATTCAG CAGTACAAGA AGATAGTTAT GGCCTAATTA CAACCACAAG AGCAACAATT    1200

AATCCTGGAG TTGATGGAAC AAACCGCATA GAGTCAACGG CAGTAGATTT TCGTTCTGCA    1260

TTGATAGGTA TATATGGCGT GAATAGAGCT TCTTTTGTCC CAGGAGGCTT GTTTAATGGT    1320

ACGACTTCTC CTGCTAATGG AGGATGTAGA GATCTCTATG ATACAAATGA TGAATTACCA    1380

CCAGATGAAA GTACCGGAAG TTCTACCCAT AGACTATCTC ATGTTACCTT TTTTAGTTTT    1440

CAAACTAATC AGGCTGGATC TATAGCTAAT GCAGGAAGTG TACCTACTTA TGTTTGGACC    1500

CGTCGTGATG TGGACCTTAA TAATACGATT ACCCCAAATA GAATTACACA ATTACCATTG    1560

GTAAAGGCAT CTGCACCTGT TTCGGGTACT ACGGTCTTAA AAGGTCCAGG ATTTACAGGA    1620

GGGGGTATAC TCCGAAGAAC AACTAATGGC ACATTTGGAA CGTTAAGAGT AACAGTTAAT    1680

TCACCATTAA CACAAAGATA TCGCGTAAGA GTTCGTTTTG CTTCATCAGG AAATTTCAGC    1740

ATAAGGATAC TGCGTGGAAA TACCTCTATA GCTTATCAAA GATTTGGGAG TACAATGAAC    1800

AGAGGACAGG AACTAACTTA CGAATCATTT GTCACAAGTG AGTTCACTAC TAATCAGAGC    1860

GATCTGCCTT TTACATTTAC ACAAGCTCAA GAAAATTTAA CAATCCTTGC AGAAGGTGTT    1920

AGCACCGGTA GTGAATATTT TATAGATAGA ATTGAAATCA TCCCTGTGAA CCCGGCACGA    1980

GAAGCAGAAG AGGATTTAGA AGCAGCGAAG AAAGCGGTGG CGAACTTGTT TACACGTACA    2040

AGGGACGGAT TACAGGTAAA TGTGACAGAT TATCAAGTGG ACCAAGCGGC AAATTTAGTG    2100

TCATGCTTAT CCGATGAACA ATATGGGCAT GACAAAAAGA TGTTATTGGA AGCGGTAAGA    2160

GCGGCAAAAC GCCTCAGCCG CGAACGCAAC TTACTTCAAG ATCCAGATTT TAATACAATC    2220

AATAGTACAG AAGAGAATGG CTGGAAGGCA AGTAACGGTG TTACTATTAG CGAGGGCGGT    2280

CCATTCTTTA AAGGTCGTGC ACTTCAGTTA GCAAGCGCAA GAGAAAATTA TCCAACATAC    2340

ATTTATCAAA AAGTAGATGC ATCGGTGTTA AAGCCTTATA CACGCTATAG ACTAGATGGA    2400

TTTGTGAAGA GTAGTCAAGA TTTAGAAATT GATCTCATCC ACCATCATAA AGTCCATCTT    2460

GTAAAAAATG TACCAGATAA TTTAGTATCT GATACTTACT CAGATGGTTC TTGCAGCGGA    2520

ATCAACCGTT GTGATGAACA GCATCAGGTA GATATGCAGC TAGATGCGGA GCATCATCCA    2580

ATGGATTGCT GTGAAGCGGC TCAAACACAT GAGTTTTCTT CCTATATTAA TACAGGGGAT    2640

CTAAATGCAA GTGTAGATCA GGGCATTTGG GTTGTATTAA AAGTTCGAAC AACAGATGGG    2700

TATGCGACGT TAGGAAATCT TGAATTGGTA GAGGTTGGGC CATTATCGGG TGAATCTCTA    2760

GAACGGGAAC AAAGAGATAA TGCGAAATGG AATGCAGAGC TAGGAAGAAA ACGTGCAGAA    2820

ATAGATCGTG TGTATTTAGC TGCGAAACAA GCAATTAATC ATCTGTTTGT AGACTATCAA    2880

GATCAACAAT TAAATCCAGA AATTGGGCTA GCAGAAATTA ATGAAGCTTC AAATCTTGTA    2940

GAGTCAATTT CGGGTGTATA TAGTGATACA CTATTACAGA TTCCTGGGAT TAACTACGAA    3000

ATTTACACAG AGTTATCCGA TCGCTTACAA CAAGCATCGT ATCTGTATAC GTCTAGAAAT    3060

GCGGTGCAAA ATGGAGACTT TAACAGTGGT CTAGATAGTT GGAATACAAC TATGGATGCA    3120

TCGGTTCAGC AAGATGGCAA TATGCATTTC TTAGTTCTTT CGCATTGGGA TGCACAAGTT    3180

TCCCAACAAT TGAGAGTAAA TCCGAATTGT AAGTATGTCT TACGTGTGAC AGCAAGAAAA    3240

GTAGGAGGCG GAGATGGATA CGTCACAATC CGAGATGGCG CTCATCACCA AGAAACTCTT    3300
```

```
ACATTTAATG CATGTGACTA CGATGTAAAT GGTACGTATG TCAATGACAA TTCGTATATA     3360

ACAGAAGAAG TGGTATTCTA CCCAGAGACA AAACATATGT GGGTAGAGGT GAGTGAATCC     3420

GAAGGTTCAT TCTATATAGA CAGTATTGAG TTTATTGAAA CACAAGAGTA G              3471
```

(2) INFORMATION FOR SEQ ID NO: 74:

(i) SEQUENCE CHARACTERISTICS:
        (A) LENGTH: 1150 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 74:

```
Met Asn Arg Asn Asn Pro Asn Glu Tyr Glu Ile Ile Asp Ala Pro Tyr
1               5                  10                  15

Cys Gly Cys Pro Ser Asp Asp Val Arg Tyr Pro Leu Ala Ser Asp
            20                  25                  30

Pro Asn Ala Ala Phe Gln Asn Met Asn Tyr Lys Glu Tyr Leu Gln Thr
            35                  40                  45

Tyr Asp Gly Asp Tyr Thr Gly Ser Leu Ile Asn Pro Asn Leu Ser Ile
50                  55                  60

Asn Pro Arg Asp Val Leu Gln Thr Gly Ile Asn Ile Val Gly Arg Ile
65                  70                  75                  80

Leu Gly Phe Leu Gly Val Pro Phe Ala Gly Gln Leu Val Thr Phe Tyr
            85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asp Gln Lys Ile Ser
            115                 120                 125

Ala Gln Val Val Arg Asn Ala Leu Asp Asp Leu Thr Gly Leu His Asp
            130                 135                 140

Tyr Tyr Glu Glu Tyr Leu Ala Ala Leu Glu Glu Trp Leu Glu Arg Pro
145                 150                 155                 160

Asn Gly Ala Arg Ala Asn Leu Val Thr Gln Arg Phe Glu Asn Leu His
            165                 170                 175

Thr Ala Phe Val Thr Arg Met Pro Ser Phe Gly Thr Gly Pro Gly Ser
            180                 185                 190

Gln Arg Asp Ala Val Ala Leu Leu Thr Val Tyr Ala Gln Ala Ala Asn
            195                 200                 205

Leu His Leu Leu Leu Leu Lys Asp Ala Glu Ile Tyr Gly Ala Arg Trp
            210                 215                 220

Gly Leu Gln Gln Gly Gln Ile Asn Leu Tyr Phe Asn Ala Gln Gln Glu
225                 230                 235                 240

Arg Thr Arg Ile Tyr Thr Asn His Cys Val Glu Thr Tyr Asn Arg Gly
            245                 250                 255

Leu Glu Asp Val Arg Gly Thr Asn Thr Glu Ser Trp Leu Asn Tyr His
            260                 265                 270

Arg Phe Arg Arg Glu Met Thr Leu Met Ala Met Asp Leu Val Ala Leu
            275                 280                 285

Phe Pro Phe Tyr Asn Val Arg Gln Tyr Pro Asn Gly Ala Asn Pro Gln
            290                 295                 300

Leu Thr Arg Glu Ile Tyr Thr Asp Pro Ile Val Tyr Asn Pro Pro Ala
305                 310                 315                 320
```

```
-continued

Asn Gln Gly Ile Cys Arg Arg Trp Gly Asn Asn Pro Tyr Asn Thr Phe
            325                 330                 335

Ser Glu Leu Glu Asn Ala Phe Ile Arg Pro Pro His Leu Phe Glu Arg
            340                 345                 350

Leu Asn Arg Leu Thr Ile Ser Arg Asn Arg Tyr Thr Ala Pro Thr Thr
            355                 360                 365

Asn Ser Phe Leu Asp Tyr Trp Ser Gly His Thr Leu Gln Ser Gln His
    370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Arg Ala Ile Asp Ser
                405                 410                 415

Arg Ala Arg Asn Phe Gly Asn Leu Tyr Ala Asn Leu Tyr Gly Val Ser
            420                 425                 430

Ser Leu Asn Ile Phe Pro Thr Gly Val Met Ser Glu Ile Thr Asn Ala
            435                 440                 445

Ala Asn Thr Cys Arg Gln Asp Leu Thr Thr Thr Glu Glu Leu Pro Leu
    450                 455                 460

Glu Asn Asn Asn Phe Asn Leu Leu Ser His Val Thr Phe Leu Arg Phe
465                 470                 475                 480

Asn Thr Thr Gln Gly Gly Pro Leu Ala Thr Leu Gly Phe Val Pro Thr
                485                 490                 495

Tyr Val Trp Thr Arg Glu Asp Val Asp Phe Thr Asn Thr Ile Thr Ala
            500                 505                 510

Asp Arg Ile Thr Gln Leu Pro Trp Val Lys Ala Ser Glu Ile Gly Gly
        515                 520                 525

Gly Thr Thr Val Val Lys Gly Pro Gly Phe Thr Gly Gly Asp Ile Leu
    530                 535                 540

Arg Arg Thr Asp Gly Gly Ala Val Gly Thr Ile Arg Ala Asn Val Asn
545                 550                 555                 560

Ala Pro Leu Thr Gln Gln Tyr Arg Ile Arg Leu Arg Tyr Ala Ser Thr
                565                 570                 575

Thr Ser Phe Val Val Asn Leu Phe Val Asn Asn Ser Ala Ala Gly Phe
            580                 585                 590

Thr Leu Pro Ser Thr Met Ala Gln Asn Gly Ser Leu Thr Tyr Glu Ser
            595                 600                 605

Phe Asn Thr Leu Glu Val Thr His Thr Ile Arg Phe Ser Gln Ser Asp
    610                 615                 620

Thr Thr Leu Arg Leu Asn Ile Phe Pro Ser Ile Ser Gly Gln Glu Val
625                 630                 635                 640

Tyr Val Asp Lys Leu Glu Ile Val Pro Ile Asn Pro Thr Arg Glu Ala
                645                 650                 655

Glu Glu Asp Leu Glu Asp Ala Lys Lys Ala Val Ala Ser Leu Phe Thr
            660                 665                 670

Arg Thr Arg Asp Gly Leu Gln Val Asn Val Thr Asp Tyr Gln Val Asp
            675                 680                 685

Gln Ala Ala Asn Leu Val Ser Cys Leu Ser Asp Glu Gln Tyr Gly His
    690                 695                 700

Asp Lys Lys Met Leu Leu Glu Ala Val Arg Ala Ala Lys Arg Leu Ser
705                 710                 715                 720

Arg Glu Arg Asn Leu Leu Gln Asp Pro Asp Phe Asn Glu Ile Asn Ser
                725                 730                 735

Thr Glu Glu Asn Gly Trp Lys Ala Ser Asn Gly Val Thr Ile Ser Glu
```

```
                    740                 745                 750
Gly Gly Pro Phe Phe Lys Gly Arg Ala Leu Gln Leu Ala Ser Ala Arg
            755                 760                 765
Glu Asn Tyr Pro Thr Tyr Ile Tyr Gln Lys Val Asp Ala Ser Thr Leu
        770                 775                 780
Lys Pro Tyr Thr Arg Tyr Lys Leu Asp Gly Phe Val Gln Ser Ser Gln
785                 790                 795                 800
Asp Leu Glu Ile Asp Leu Ile His His Lys Val His Leu Val Lys
                805                 810                 815
Asn Val Pro Asp Asn Leu Val Ser Asp Thr Tyr Ser Asp Gly Ser Cys
            820                 825                 830
Ser Gly Ile Asn Arg Cys Glu Glu Gln His Gln Val Asp Val Gln Leu
            835                 840                 845
Asp Ala Glu Asp His Pro Lys Asp Cys Cys Glu Ala Ala Gln Thr His
        850                 855                 860
Glu Phe Ser Ser Tyr Ile His Thr Gly Asp Leu Asn Ala Ser Val Asp
865                 870                 875                 880
Gln Gly Ile Trp Val Val Leu Gln Val Arg Thr Thr Asp Gly Tyr Ala
                885                 890                 895
Thr Leu Gly Asn Leu Glu Leu Val Glu Val Gly Pro Leu Ser Gly Glu
            900                 905                 910
Ser Leu Glu Arg Glu Gln Arg Asp Asn Ala Lys Trp Asn Glu Glu Val
            915                 920                 925
Gly Arg Lys Arg Ala Glu Thr Asp Arg Ile Tyr Gln Asp Ala Lys Gln
            930                 935                 940
Ala Ile Asn His Leu Phe Val Asp Tyr Gln Asp Gln Gln Leu Ser Pro
945                 950                 955                 960
Glu Val Gly Met Ala Asp Ile Ile Asp Ala Gln Asn Leu Ile Ala Ser
                965                 970                 975
Ile Ser Asp Val Tyr Ser Asp Ala Val Leu Gln Ile Pro Gly Ile Asn
                980                 985                 990
Tyr Glu Met Tyr Thr Glu Leu Ser Asn Arg Leu Gln Gln Ala Ser Tyr
            995                 1000                1005
Leu Tyr Thr Ser Arg Asn Val Val Gln Asn Gly Asp Phe Asn Ser Gly
        1010                1015                1020
Leu Asp Ser Trp Asn Ala Thr Thr Asp Thr Ala Val Gln Gln Asp Gly
1025                1030                1035                1040
Asn Met His Phe Leu Val Leu Ser His Trp Asp Ala Gln Val Ser Gln
                1045                1050                1055
Gln Phe Arg Val Gln Pro Asn Cys Lys Tyr Val Leu Arg Val Thr Ala
                1060                1065                1070
Lys Lys Val Gly Asn Gly Asp Gly Tyr Val Thr Ile Gln Asp Gly Ala
            1075                1080                1085
His His Arg Glu Thr Leu Thr Phe Asn Ala Cys Asp Tyr Asp Val Asn
        1090                1095                1100
Gly Thr His Val Asn Asp Asn Ser Tyr Ile Thr Lys Glu Leu Val Phe
1105                1110                1115                1120
Tyr Pro Lys Thr Glu His Met Trp Val Glu Val Ser Glu Thr Glu Gly
                1125                1130                1135
Thr Phe Tyr Ile Asp Ser Ile Glu Phe Ile Glu Thr Gln Glu
            1140                1145                1150

(2) INFORMATION FOR SEQ ID NO: 75:
```

(i) SEQUENCE CHARACTERISTICS:
    (A) LENGTH: 3453 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 75:

```
ATGAATCGAA ATAATCCAAA TGAATATGAA ATTATTGATG CCCCCTATTG TGGGTGTCCG      60
TCAGATGATG ATGTGAGGTA TCCTTTGGCA AGTGACCCAA ATGCAGCGTT CCAAAATATG     120
AACTATAAAG AGTATTTACA AACGTATGAT GGAGACTACA CAGGTTCTCT TATCAATCCT     180
AACTTATCTA TTAATCCTAG AGATGTACTA CAAACAGGTA TTAATATTGT GGGAAGAATA     240
CTAGGGTTTT TAGGTGTTCC ATTTGCGGGT CAACTAGTTA CTTTCTATAC CTTTCTCTTA     300
AATCAGTTGT GGCCAACTAA TGATAATGCA GTATGGGAAG CTTTTATGGC GCAAATAGAA     360
GAGCTAATCG ATCAAAAAAT ATCGGCGCAA GTAGTAAGGA ATGCACTCGA TGACTTAACT     420
GGATTACACG ATTATTATGA GGAGTATTTA GCAGCATTAG AGGAGTGGCT GGAAAGACCG     480
AACGGAGCAA GAGCTAACTT AGTTACACAG AGGTTTGAAA ACCTGCATAC TGCATTTGTA     540
ACTAGAATGC CAAGCTTTGG TACGGGTCCT GGTAGTCAAA GAGATGCGGT AGCGTTGTTG     600
ACGGTATATG CACAAGCAGC GAATTTGCAT TTGTTATTAT TAAAAGATGC AGAAATCTAT     660
GGGGCAAGAT GGGGACTTCA ACAAGGGCAA ATTAACTTAT ATTTTAATGC TCAACAAGAA     720
CGTACTCGAA TTTATACCAA TCATTGCGTG GAAACATATA ATAGAGGATT AGAAGATGTA     780
AGAGGAACAA ATACAGAAAG TTGGTTAAAT TACCATCGAT TCCGTAGAGA GATGACATTA     840
ATGGCAATGG ATTTAGTGGC CCTATTCCCA TTCTATAATG TGCGACAATA TCCAAATGGG     900
GCAAATCCAC AGCTTACACG TGAAATATAT ACAGATCCAA TCGTATATAA TCCACCAGCT     960
AATCAGGGAA TTTGCCGACG TTGGGGGAAT AATCCGTATA ATACATTTTC TGAACTTGAA    1020
AATGCTTTTA TTCGCCCGCC ACATCTTTTT GAAAGGTTGA ACAGATTAAC TATTTCTAGA    1080
AACCGATATA CAGCTCCAAC AACTAATAGC TTCCTAGACT ATTGGTCAGG TCATACTTTA    1140
CAAAGCCAAC ATGCAAATAA CCCGACGACA TATGAAACTA GTTACGGTCA GATTACCTCT    1200
AACACACGTT TATTCAATAC GACTAATGGA GCCCGTGCAA TAGATTCAAG GGCAAGAAAT    1260
TTTGGTAACT TATACGCTAA TTTGTATGGC GTTAGCAGCT TGAACATTTT CCCAACAGGT    1320
GTGATGAGTG AAATCACCAA TGCAGCTAAT ACGTGTCGGC AAGACCTTAC TACAACTGAA    1380
GAACTACCAC TAGAGAATAA TAATTTTAAT CTTTTATCTC ATGTTACTTT CTTACGCTTC    1440
AATACTACTC AGGGTGGCCC CCTTGCAACT CTAGGGTTTG TACCCACATA TGTGTGGACA    1500
CGTGAAGATG TAGATTTTAC GAACACAATT ACTGCGGATA GAATTACACA ACTACCATGG    1560
GTAAAGGCAT CTGAAATAGG TGGGGGTACT ACTGTCGTGA AAGGTCCAGG ATTTACAGGA    1620
GGGGATATAC TTCGAAGAAC GGACGGTGGT GCAGTTGGAA CGATTAGAGC TAATGTTAAT    1680
GCCCCATTAA CACAACAATA TCGTATAAGA TTACGCTATG CTTCGACAAC AAGTTTTGTT    1740
GTTAATTTAT TTGTTAATAA TAGTGCGGCT GGCTTTACTT TACCGAGTAC AATGGCTCAA    1800
AATGGTTCTT TAACATACGA GTCGTTTAAT ACCTTAGAGG TAACTCATAC TATTAGATTT    1860
TCACAGTCAG ATACTACACT TAGGTTGAAT ATATTCCCGT CTATCTCTGG TCAAGAAGTG    1920
TATGTAGATA AACTTGAAAT CGTTCCAATT AACCCGACAC GAGAAGCGGA AGAAGATTTA    1980
GAAGATGCAA AGAAAGCGGT GGCGAGCTTG TTTACACGTA CAAGGGATGG ATTACAGGTA    2040
```

```
AATGTGACAG ATTACCAAGT CGATCAGGCG GCAAATTTAG TGTCGTGCTT ATCAGATGAA    2100

CAATATGGGC ATGATAAAAA GATGTTATTG GAAGCCGTAC GCGCAGCAAA ACGCCTCAGC    2160

CGCGAACGCA ACTTACTTCA AGATCCAGAT TTTAATGAAA TAAATAGCAC AGAAGAAAAT    2220

GGCTGGAAGG CAAGTAACGG TGTTACTATT AGCGAGGGCG GTCCATTCTT TAAAGGTCGT    2280

GCACTTCAGT TAGCAAGCGC ACGTGAAAAT TACCCAACAT ACATCTATCA AAAGGTAGAT    2340

GCATCGACGT TAAAACCTTA TACACGATAT AAACTAGATG GATTTGTGCA AAGTAGTCAA    2400

GATTTAGAAA TTGACCTCAT TCATCATCAT AAAGTCCACC TCGTGAAAAA TGTACCAGAT    2460

AATTTAGTAT CTGATACTTA TTCTGATGGC TCATGTAGTG GAATTAACCG TTGTGAGGAA    2520

CAACATCAGG TAGATGTGCA GCTAGATGCG GAGGATCATC CAAAGGATTG TTGTGAAGCG    2580

GCTCAAACAC ATGAGTTTTC TTCCTATATT CATACAGGTG ATCTAAATGC AAGTGTAGAT    2640

CAAGGCATTT GGGTTGTATT GCAGGTTCGA ACAACAGATG GTTATGCGAC GTTAGGAAAT    2700

CTTGAATTGG TAGAGGTTGG TCCATTATCG GGTGAATCTT TAGAACGAGA ACAAAGAGAT    2760

AATGCGAAAT GGAATGAAGA GGTAGGAAGA AAGCGTGCAG AAACAGATCG CATATATCAA    2820

GATGCGAAAC AAGCAATTAA CCATCTATTT GTAGACTATC AAGATCAACA ATTAAGTCCA    2880

GAGGTAGGGA TGGCGGATAT TATTGATGCT CAAAATCTTA TCGCATCAAT TTCAGATGTA    2940

TATAGCGATG CAGTACTGCA AATCCCTGGG ATTAACTACG AGATGTATAC AGAGTTATCC    3000

AATCGATTAC AACAAGCATC GTATCTGTAT ACGTCTCGAA ATGTCGTGCA AAATGGGGAC    3060

TTTAACAGTG GTTTAGATAG TTGGAATGCA ACAACTGATA CAGCTGTTCA GCAGGATGGC    3120

AATATGCATT TCTTAGTTCT TTCCCATTGG GATGCACAAG TTTCTCAACA ATTTAGAGTA    3180

CAGCCGAATT GTAAATATGT GTTACGTGTG ACAGCGAAGA AAGTAGGGAA CGGAGATGGA    3240

TATGTTACGA TCCAAGATGG CGCTCATCAC CGAGAAACAC TGACATTCAA TGCATGTGAC    3300

TACGATGTAA ATGGTACGCA TGTAAATGAT AATTCGTATA TTACAAAAGA ATTGGTGTTC    3360

TATCCAAAGA CGGAACATAT GTGGGTAGAG GTAAGTGAAA CAGAAGGTAC CTTCTATATA    3420

GACAGCATTG AGTTCATTGA AACACAAGAG TAG                                3453

(2) INFORMATION FOR SEQ ID NO: 76:

(i) SEQUENCE CHARACTERISTICS:
        (A) LENGTH: 1134 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 76:

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Gly Asn Val Arg
            20                  25                  30

Thr Gly Leu Gln Thr Gly Ile Asp Ile Val Ala Val Val Gly Ala
        35                  40                  45

Leu Gly Gly Pro Val Gly Gly Ile Leu Thr Gly Phe Leu Ser Thr Leu
    50                  55                  60

Phe Gly Phe Leu Trp Pro Ser Asn Asp Gln Ala Val Trp Glu Ala Phe
65                  70                  75                  80

Ile Glu Gln Met Glu Glu Leu Ile Glu Gln Arg Ile Ser Asp Gln Val
                85                  90                  95
```

-continued

```
Val Arg Thr Ala Leu Asp Asp Leu Thr Gly Ile Gln Asn Tyr Tyr Asn
            100                 105                 110

Gln Tyr Leu Ile Ala Leu Lys Glu Trp Glu Arg Pro Asn Gly Val
        115                 120                 125

Arg Ala Asn Leu Val Leu Gln Arg Phe Glu Ile Leu His Ala Leu Phe
    130                 135                 140

Val Ser Ser Met Pro Ser Phe Gly Ser Gly Pro Gly Ser Gln Arg Phe
145                 150                 155                 160

Gln Ala Gln Leu Leu Val Val Tyr Ala Gln Ala Asn Leu His Leu
            165                 170                 175

Leu Leu Leu Ala Asp Ala Glu Lys Tyr Gly Ala Arg Trp Gly Leu Arg
                180                 185                 190

Glu Ser Gln Ile Gly Asn Leu Tyr Phe Asn Glu Leu Gln Thr Arg Thr
            195                 200                 205

Arg Asp Tyr Thr Asn His Cys Val Asn Ala Tyr Asn Asn Gly Leu Ala
    210                 215                 220

Gly Leu Arg Gly Thr Ser Ala Glu Ser Trp Leu Lys Tyr His Gln Phe
225                 230                 235                 240

Arg Arg Glu Ala Thr Leu Met Ala Met Asp Leu Ile Ala Leu Phe Pro
                245                 250                 255

Tyr Tyr Asn Thr Arg Arg Tyr Pro Ile Ala Val Asn Pro Gln Leu Thr
            260                 265                 270

Arg Glu Val Tyr Thr Asp Pro Leu Gly Val Pro Ser Glu Glu Ser Ser
        275                 280                 285

Leu Phe Pro Glu Leu Arg Cys Leu Arg Trp Gln Glu Thr Ser Ala Met
        290                 295                 300

Thr Phe Ser Asn Leu Glu Asn Ala Ile Ile Ser Ser Pro His Leu Phe
305                 310                 315                 320

Asp Thr Ile Asn Asn Leu Met Ile Tyr Thr Gly Ser Phe Ser Val His
                325                 330                 335

Leu Thr Asn Gln Leu Ile Glu Gly Trp Ile Gly His Ser Val Thr Ser
            340                 345                 350

Ser Leu Leu Ala Ser Gly Pro Thr Thr Val Leu Arg Arg Asn Tyr Gly
        355                 360                 365

Ser Thr Thr Ser Ile Val Asn Tyr Phe Ser Phe Asn Asp Arg Asp Val
    370                 375                 380

Tyr Gln Ile Asn Thr Arg Ser His Thr Gly Leu Gly Phe Gln Asn Ala
385                 390                 395                 400

Pro Leu Phe Gly Ile Thr Arg Ala Gln Phe Tyr Pro Gly Gly Thr Tyr
                405                 410                 415

Ser Val Thr Gln Arg Asn Ala Leu Thr Cys Glu Gln Asn Tyr Asn Ser
            420                 425                 430

Ile Asp Glu Leu Pro Ser Leu Asp Pro Asn Glu Pro Ile Ser Arg Ser
        435                 440                 445

Tyr Ser His Arg Leu Ser His Ile Thr Ser Tyr Leu His Arg Val Leu
    450                 455                 460

Thr Ile Asp Gly Ile Asn Ile Tyr Ser Gly Asn Leu Pro Thr Tyr Val
465                 470                 475                 480

Trp Thr His Arg Asp Val Asp Leu Thr Asn Thr Ile Thr Ala Asp Arg
                485                 490                 495

Ile Thr Gln Leu Pro Leu Val Lys Ser Phe Glu Ile Pro Ala Gly Thr
            500                 505                 510

Thr Val Val Arg Gly Pro Gly Phe Thr Gly Gly Asp Ile Leu Arg Arg
```

-continued

```
                515                 520                 525
Thr Gly Val Gly Thr Phe Gly Thr Ile Arg Val Arg Thr Thr Ala Pro
            530                 535                 540
Leu Thr Gln Arg Tyr Arg Ile Arg Phe Arg Phe Ala Ser Thr Thr Asn
545                 550                 555                 560
Leu Phe Ile Gly Ile Arg Val Gly Asp Arg Gln Val Asn Tyr Phe Asp
                565                 570                 575
Phe Gly Arg Thr Met Asn Arg Gly Asp Glu Leu Arg Tyr Glu Ser Phe
            580                 585                 590
Ala Thr Arg Glu Phe Thr Thr Asp Phe Asn Phe Arg Gln Pro Gln Glu
            595                 600                 605
Leu Ile Ser Val Phe Ala Asn Ala Phe Ser Ala Gly Gln Glu Val Tyr
            610                 615                 620
Phe Asp Arg Ile Glu Ile Pro Val Asn Pro Ala Arg Glu Ala Lys
625                 630                 635                 640
Glu Asp Leu Glu Ala Ala Lys Lys Ala Val Ala Ser Leu Phe Thr Arg
                645                 650                 655
Thr Arg Asp Gly Leu Gln Val Asn Val Lys Asp Tyr Gln Val Asp Gln
                660                 665                 670
Ala Ala Asn Leu Val Ser Cys Leu Ser Asp Glu Gln Tyr Gly Tyr Asp
                675                 680                 685
Lys Lys Met Leu Leu Glu Ala Val Arg Ala Ala Lys Arg Leu Ser Arg
            690                 695                 700
Glu Arg Asn Leu Leu Gln Asp Pro Asp Phe Asn Thr Ile Asn Ser Thr
705                 710                 715                 720
Glu Glu Asn Gly Trp Lys Ala Ser Asn Gly Val Thr Ile Ser Glu Gly
                725                 730                 735
Gly Pro Phe Tyr Lys Gly Arg Ala Leu Gln Leu Ala Ser Ala Arg Glu
                740                 745                 750
Asn Tyr Pro Thr Tyr Ile Tyr Gln Lys Val Asp Ala Ser Glu Leu Lys
                755                 760                 765
Pro Tyr Thr Arg Tyr Arg Ser Asp Gly Phe Val Lys Ser Ser Gln Asp
            770                 775                 780
Leu Glu Ile Asp Leu Ile His His Lys Val His Leu Val Lys Asn
785                 790                 795                 800
Val Pro Asp Asn Leu Val Ser Asp Thr Tyr Pro Asp Asp Ser Cys Ser
                805                 810                 815
Gly Ile Asn Arg Cys Gln Glu Gln Met Val Asn Ala Gln Leu Glu
                820                 825                 830
Thr Glu His His His Pro Met Asp Cys Cys Glu Ala Ala Gln Thr His
            835                 840                 845
Glu Phe Ser Ser Tyr Ile Asp Thr Gly Asp Leu Asn Ser Ser Val Asp
850                 855                 860
Gln Gly Ile Trp Ala Ile Phe Lys Val Arg Thr Thr Asp Gly Tyr Ala
865                 870                 875                 880
Thr Leu Gly Asn Leu Glu Leu Val Glu Val Gly Pro Leu Ser Gly Glu
                885                 890                 895
Ser Leu Glu Arg Glu Gln Arg Asp Asn Thr Lys Trp Ser Ala Glu Leu
            900                 905                 910
Gly Arg Lys Arg Ala Glu Thr Asp Arg Val Tyr Gln Asp Ala Lys Gln
            915                 920                 925
Ser Ile Asn His Leu Phe Val Asp Tyr Gln Asp Gln Gln Leu Asn Pro
            930                 935                 940
```

-continued

```
Glu Ile Gly Met Ala Asp Ile Met Asp Ala Gln Asn Leu Val Ala Ser
945                 950                 955                 960

Ile Ser Asp Val Tyr Ser Asp Ala Val Leu Gln Ile Pro Gly Ile Asn
                965                 970                 975

Tyr Glu Ile Tyr Thr Glu Leu Ser Asn Arg Leu Gln Gln Ala Ser Tyr
            980                 985                 990

Leu Tyr Thr Ser Arg Asn Ala Val Gln Asn Gly Asp Phe Asn Asn Gly
        995                 1000                1005

Leu Asp Ser Trp Asn Ala Thr Ala Gly Ala Ser Val Gln Gln Asp Gly
    1010                1015                1020

Asn Thr His Phe Leu Val Leu Ser His Trp Asp Ala Gln Val Ser Gln
1025                1030                1035                1040

Gln Phe Arg Val Gln Pro Asn Cys Lys Tyr Val Leu Arg Val Thr Ala
                1045                1050                1055

Glu Lys Val Gly Gly Gly Asp Gly Tyr Val Thr Ile Arg Asp Gly Ala
                1060                1065                1070

His His Thr Glu Thr Leu Thr Phe Asn Ala Cys Asp Tyr Asp Ile Asn
            1075                1080                1085

Gly Thr Tyr Val Thr Asp Asn Thr Tyr Leu Thr Lys Glu Val Ile Phe
        1090                1095                1100

Tyr Ser His Thr Glu His Met Trp Val Glu Val Asn Glu Thr Glu Gly
1105                1110                1115                1120

Ala Phe His Ile Asp Ser Ile Glu Phe Val Glu Thr Glu Lys
                1125                1130
```

(2) INFORMATION FOR SEQ ID NO: 77:

(i) SEQUENCE CHARACTERISTICS:
        (A) LENGTH: 3411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

```
ATGGATAACA ATCCGAACAT CAATGAATGC ATTCCTTATA ATTGTTTAAG TAACCCTGAA      60

GTAGAAGTAT TAGGTGGAGA AAGAGGAAAT GTTAGAACTG GACTACAAAC TGGAATTGAT     120

ATTGTTGCAG TAGTAGTAGG TGCTTTAGGT GGACCAGTTG GTGGCATACT CACTGGTTTT     180

CTTTCTACTC TTTTTGGTTT TCTTTGGCCA TCTAATGATC AAGCAGTATG GGAAGCTTTT     240

ATAGAACAAA TGGAAGAACT GATTGAACAA AGGATATCAG ATCAAGTAGT AAGGACTGCA     300

CTCGATGACT TAACTGGAAT TCAAAATTAT TATAATCAAT ATCTAATAGC ATTAAAGGAA     360

TGGGAGGAAA GACCAAACGG CGTAAGAGCA AACTTAGTTT TGCAAAGATT TGAAATCTTG     420

CACGCGCTAT TTGTAAGTAG TATGCCAAGT TTTGGTAGTG GCCCTGGAAG TCAAAGGTTT     480

CAGGCACAAT TGTTGGTTGT TTATGCGCAA GCAGCAAATC TTCATTTACT ATTATTAGCT     540

GATGCTGAAA AGTATGGGGC AAGATGGGGA CTCCGTGAAT CCCAGATAGG AAATTTATAT     600

TTTAATGAAC TACAAACTCG TACTCGAGAT TACACCAACC ATTGTGTAAA CGCGTATAAT     660

AACGGGTTAG CCGGGTTACG AGGAACGAGC GCTGAAAGTT GGTTAAAGTA CCATCAATTC     720

CGCAGAGAAG CAACCTTAAT GGCAATGGAT TTGATAGCTT TATTTCCATA TTATAACACC     780

CGGCGATATC CAATCGCAGT AAATCCTCAG CTTACACGTG AGGTATATAC AGATCCATTA     840

GGCGTTCCTT CTGAAGAATC AAGTTTATTT CCAGAATTGA GATGCTTAAG ATGGCAAGAG     900
```

```
ACTTCTGCCA TGACTTTTTC AAATTTGGAA AATGCAATAA TTTCGTCACC ACATCTATTT      960

GACACAATAA ACAATTTAAT GATTTATACC GGTTCCTTTT CCGTTCACCT AACCAATCAA     1020

TTAATTGAAG GGTGGATTGG ACATTCTGTA ACTAGTAGTT TGTTGGCCAG TGGACCAACA     1080

ACAGTACTGA GAAGAAATTA CGGTAGCACG ACATCTATTG TAAACTATTT TAGTTTTAAT     1140

GATCGTGATG TTTATCAGAT TAATACGAGA TCACATACTG GGTTGGGATT CCAGAACGCA     1200

CCTTTATTTG GAATCACTAG AGCTCAATTT TACCCAGGTG GGACTTATTC AGTAACTCAA     1260

CGAAATGCAT TAACATGTGA ACAAAATTAT AATTCAATTG ATGAGTTACC GAGCCTAGAC     1320

CCAAATGAAC CTATCAGTAG AAGTTATAGT CATAGATTAT CTCATATTAC CTCCTATTTG     1380

CATCGTGTAT TGACTATTGA TGGTATTAAT ATATATTCAG GAAATCTCCC TACTTATGTA     1440

TGGACCCATC GCGATGTGGA CCTTACAAAC ACGATTACCG CAGATAGAAT TACACAACTA     1500

CCATTGGTAA AGTCATTTGA ATACCTGCG GGTACTACTG TCGTAAGAGG ACCAGGTTTT      1560

ACAGGAGGGG ATATACTCCG AAGAACAGGG GTTGGTACAT TTGGAACAAT AAGGGTAAGG     1620

ACTACTGCCC CCTTAACACA AAGATATCGC ATAAGATTCC GTTTCGCTTC TACCACAAAT     1680

TTGTTCATTG GTATAAGAGT TGGTGATAGA CAAGTAAATT ATTTTGACTT CGGAAGAACA     1740

ATGAACAGAG GAGATGAATT AAGGTACGAA TCTTTTGCTA CAAGGGAGTT TACTACTGAT     1800

TTTAATTTTA GACAACCTCA AGAATTAATC TCAGTGTTTG CAAATGCATT TAGCGCTGGT     1860

CAAGAAGTTT ATTTTGATAG AATTGAGATT ATCCCCGTTA ATCCCGCACG AGAGGCGAAA     1920

GAGGATCTAG AAGCAGCAAA GAAAGCGGTG GCGAGCTTGT TTACACGCAC AAGGGACGGA     1980

TTACAAGTAA ATGTGAAAGA TTATCAAGTC GATCAAGCGG CAAATTTAGT GTCATGCTTA     2040

TCAGATGAAC AATATGGGTA TGACAAAAAG ATGTTATTGG AAGCGGTACG CGCGGCAAAA     2100

CGCCTCAGCC GAGAACGTAA CTTACTTCAG GATCCAGATT TTAATACAAT CAATAGTACA     2160

GAAGAAAATG GATGGAAAGC AAGTAACGGC GTTACTATTA GTGAGGGCGG TCCATTCTAT     2220

AAAGGCCGTG CACTTCAGCT AGCAAGTGCA CGAGAAAATT ATCCAACATA CATTTATCAA     2280

AAAGTAGATG CATCGGAGTT AAAACCTTAT ACACGTTATA GATCAGATGG GTTCGTGAAG     2340

AGTAGTCAAG ATTTAGAAAT TGATCTCATT CACCATCATA AAGTCCATCT TGTGAAAAAT     2400

GTACCAGATA ATTTAGTATC TGATACTTAC CCAGATGATT CTTGTAGTGG AATCAATCGA     2460

TGTCAGGAAC AACAGATGGT AAATGCGCAA CTGGAAACAG AGCATCATCA TCCGATGGAT     2520

TGCTGTGAAG CAGCTCAAAC ACATGAGTTT TCTTCCTATA TTGATACAGG GGATTTAAAT     2580

TCGAGTGTAG ACCAGGGAAT CTGGGCGATC TTTAAAGTTC GAACAACCGA TGGTTATGCG     2640

ACGTTAGGAA ATCTTGAATT GGTAGAGGTC GGACCGTTAT CGGGTGAATC TTTAGAACGT     2700

GAACAAAGGG ATAATACAAA ATGGAGTGCA GAGCTAGGAA GAAAGCGTGC AGAAACAGAT     2760

CGCGTGTATC AAGATGCCAA ACAATCCATC AATCATTTAT TTGTGGATTA TCAAGATCAA     2820

CAATTAAATC CAGAAATAGG GATGGCAGAT ATTATGGACG CTCAAAATCT TGTCGCATCA     2880

ATTTCAGATG TATATAGCGA TGCCGTACTG CAAATCCCTG GAATTAACTA TGAGATTTAC     2940

ACAGAGCTGT CCAATCGCTT ACAACAAGCA TCGTATCTGT ATACGTCTCG AAATGCGGTG     3000

CAAAATGGGG ACTTTAACAA CGGGCTAGAT AGCTGGAATG CAACAGCGGG TGCATCGGTA     3060

CAACAGGATG GCAATACGCA TTTCTTAGTT CTTTCTCATT GGGATGCACA AGTTTCTCAA     3120

CAATTTAGAG TGCAGCCGAA TTGTAAATAT GTATTACGTG TAACAGCAGA GAAAGTAGGC     3180

GGCGGAGACG GATACGTGAC TATCCGGGAT GGTGCTCATC ATACAGAAAC GCTTACATTT     3240
```

```
AATGCATGTG ATTATGATAT AAATGGCACG TACGTGACTG ATAATACGTA TCTAACAAAA      3300

GAAGTGATAT TCTATTCACA TACAGAACAC ATGTGGGTAG AGGTAAATGA AACAGAAGGT      3360

GCATTTCATA TAGATAGTAT TGAATTCGTT GAAACAGAAA AGTAAGGTAC C               3411
```

(2) INFORMATION FOR SEQ ID NO: 78:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 78:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Ala Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320
```

-continued

```
Asn Ile Leu Pro Thr Leu Ser Asn Thr Phe Ser Asn Pro Asn Tyr Ala
            325                 330                 335
Lys Val Lys Gly Ser Asp Glu Asp Ala Lys Met Ile Val Glu Ala Lys
        340                 345                 350
Pro Gly His Ala Leu Ile Gly Phe Glu Ile Ser Asn Asp Ser Ile Thr
    355                 360                 365
Val Leu Lys Val Tyr Glu Ala Lys Leu Lys Gln Asn Tyr Gln Val Asp
370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
            420                 425                 430
Thr Leu Arg Tyr Glu Val Thr Ala Asn Phe Tyr Asp Ser Ser Thr Gly
        435                 440                 445
Glu Ile Asp Leu Asn Lys Lys Lys Val Glu Ser Ser Glu Ala Glu Tyr
    450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
            500                 505                 510
Glu Leu Leu Leu Ala Thr Asp Leu Ser Asn Lys Glu Thr Lys Leu Ile
        515                 520                 525
Val Pro Pro Ser Gly Phe Ile Ser Asn Ile Val Glu Asn Gly Ser Ile
    530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
            580                 585                 590
Thr Glu Tyr Val Ile Gln Tyr Thr Val Lys Gly Lys Pro Ser Ile His
        595                 600                 605
Leu Lys Asp Glu Asn Thr Gly Tyr Ile His Tyr Glu Asp Thr Asn Asn
    610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Asn Phe Ile Ile Leu Glu Ile Ser Pro Ser Glu Lys
            660                 665                 670
Leu Leu Ser Pro Glu Leu Ile Asn Thr Asn Asn Trp Thr Ser Thr Gly
        675                 680                 685
Ser Thr Asn Ile Ser Gly Asn Thr Leu Thr Leu Tyr Gln Gly Gly Arg
    690                 695                 700
Gly Ile Leu Lys Gln Asn Leu Gln Leu Asp Ser Phe Ser Thr Tyr Arg
705                 710                 715                 720
Val Tyr Phe Ser Val Ser Gly Asp Ala Asn Val Arg Ile Arg Asn Ser
                725                 730                 735
Arg Glu Val Leu Phe Glu Lys Arg Tyr Met Ser Gly Ala Lys Asp Val
```

-continued

```
              740                 745                 750
Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
        770                 775                 780

Asp Val Ser Ile Lys
785
```

(2) INFORMATION FOR SEQ ID NO: 79:

(i) SEQUENCE CHARACTERISTICS:
        (A) LENGTH: 2370 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 79:

```
ATGAACAAGA ATAATACTAA ATTAAGCACA AGAGCCTTAC CAAGTTTTAT TGATTATTTT      60

AATGGCATTT ATGGATTTGC CACTGGTATC AAAGACATTA TGAACATGAT TTTTAAAACG     120

GATACAGGTG GTGATCTAAC CCTAGACGAA ATTTTAAAGA ATCAGCAGTT ACTAAATGAT     180

ATTTCTGGTA AATTGGATGG GGTGAATGGA AGCTTAAATG ATCTTATCGC ACAGGGAAAC     240

TTAAATACAG AATTATCTAA GGAAATATTA AAAATTGCAA ATGAACAAAA TCAAGTTTTA     300

AATGATGTTA ATAACAAACT CGATGCGATA AATACGATGC TTCGGGTATA TCTACCTAAA     360

ATTACCTCTA TGTTGAGTGA TGTAATGAAA CAAAATTATG CGCTAAGTCT GCAAATAGAA     420

TACTTAAGTA AACAATTGCA AGAGATTTCT GATAAGTTGG ATATTATTAA TGTAAATGTA     480

CTTATTAACT CTACACTTAC TGAAATTACA CCTGCGTATC AAAGGATTAA ATATGTGAAC     540

GAAAAATTTG AGGAATTAAC TTTTGCTACA GAAACTAGTT CAAAAGTAAA AAAGGATGGC     600

TCTCCTGCAG ATATTCTTGA TGAGTTAACT GAGTTAACTG AACTAGCGAA AAGTGTAACA     660

AAAAATGATG TGGATGGTTT TGAATTTTAC CTTAATACAT TCCACGATGT AATGGTAGGA     720

AATAATTTAT TCGGGCGTTC AGCTTTAAAA ACTGCATCGG AATTAATTAC TAAAGAAAAT     780

GTGAAAGCAA GTGGCAGTGA GGTCGGAAAT GTTTATAACT TCTTAATTGT ATTAACAGCT     840

CTGCAAGCAA AAGCTTTTCT TACTTTAACA ACATGCCGAA ATTATTAGG CTTAGCAGAT     900

ATTGATTATA CTTCTATTAT GAATGAACAT TTAAATAAGG AAAAAGAGGA ATTTAGAGTA     960

AACATCCTCC CTACACTTTC TAATACTTTT TCTAATCCTA ATTATGCAAA AGTTAAAGGA    1020

AGTGATGAAG ATGCAAAGAT GATTGTGGAA GCTAAACCAG GACATGCATT GATTGGGTTT    1080

GAAATTAGTA ATGATTCAAT TACAGTATTA AAAGTATATG AGGCTAAGCT AAAACAAAAT    1140

TATCAAGTCG ATAAGGATTC CTTATCGGAA GTTATTTATG GTGATATGGA TAAATTATTG    1200

TGCCCAGATC AATCTGAACA AATCTATTAT ACAAATAACA TAGTATTTCC AAATGAATAT    1260

GTAATTACTA AAATTGATTT CACTAAAAAA ATGAAAACTT TAAGATATGA GGTAACAGCG    1320

AATTTTTATG ATTCTTCTAC AGGAGAAATT GACTTAAATA AGAAAAAAGT AGAATCAAGT    1380

GAAGCGGAGT ATAGAACGTT AAGTGCTAAT GATGATGGGG TGTATATGCC GTTAGGTGTC    1440

ATCAGTGAAA CATTTTTGAC TCCGATTAAT GGGTTTGGCC TCCAAGCTGA TGAAAATTCA    1500

AGATTAATTA CTTTAACATG TAAATCATAT TTAAGAGAAC TACTGCTAGC AACAGACTTA    1560

AGCAATAAAG AAACTAAATT GATTGTCCCG CCAAGTGGTT TTATTAGCAA TATTGTAGAG    1620

AACGGGTCCA TAGAAGAGGA CAATTTAGAG CCGTGGAAAG CAAATAATAA GAATGCGTAT    1680
```

```
GTAGATCATA CAGGCGGAGT GAATGGAACT AAAGCTTTAT ATGTTCATAA GGACGGAGGA      1740

ATTTCACAAT TTATTGGAGA TAAGTTAAAA CCGAAAACTG AGTATGTAAT CCAATATACT      1800

GTTAAAGGAA AACCTTCTAT TCATTTAAAA GATGAAAATA CTGGATATAT TCATTATGAA      1860

GATACAAATA ATAATTTAGA AGATTATCAA ACTATTAATA AACGTTTTAC TACAGGAACT      1920

GATTTAAAGG GAGTGTATTT AATTTTAAAA AGTCAAAATG GAGATGAAGC TTGGGGAGAT      1980

AACTTTATTA TTTTGGAAAT TAGTCCTTCT GAAAAGTTAT TAAGTCCAGA ATTAATTAAT      2040

ACAAATAATT GGACGAGTAC GGGATCAACT AATATTAGCG GTAATACACT CACTCTTTAT      2100

CAGGGAGGAC GAGGGATTCT AAAACAAAAC CTTCAATTAG ATAGTTTTTC AACTTATAGA      2160

GTGTATTTTT CTGTGTCCGG AGATGCTAAT GTAAGGATTA GAAATTCTAG GAAGTGTTA      2220

TTTGAAAAAA GATATATGAG CGGTGCTAAA GATGTTTCTG AAATGTTCAC TACAAAATTT      2280

GAGAAAGATA ACTTTTATAT AGAGCTTTCT CAAGGGAATA ATTTATATGG TGGTCCTATT      2340

GTACATTTTT ACGATGTCTC TATTAAGTAA                                      2370
```

(2) INFORMATION FOR SEQ ID NO: 80:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 80:

```
Met Asn Lys Asp Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Glu Val Asn Asn Lys Leu Glu Ala Ile Ser Thr
            100                 105                 110

Ile Phe Arg Val Tyr Leu Pro Lys Asn Thr Ser Arg Gly Gly Gly Val
        115                 120                 125

Met Lys Gln Asn Tyr Ala Leu Ser Leu Gln Met Glu Asn Leu Ser Lys
130                 135                 140

Gln Leu Gln Glu Ile Ser Val Lys Trp Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
210                 215                 220
```

```
Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
            245                 250                 255

Thr Lys Glu Asn Val Lys Thr Ser Gly Ser Glu Val Gly Asn Val Tyr
        260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
        290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Xaa Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640
```

```
Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
            675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
            770                 775                 780

Asp Val Ser Ile Lys
785

(2) INFORMATION FOR SEQ ID NO: 81:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 81:

ATGAACAAGG ATAATACTAA ATTAAGCACA AGAGCCTTAC CAAGTTTTAT TGATTATTTT      60

AATGGCATTT ATGGATTTGC CACTGGTATC AAAGACATTA TGAACATGAT TTTTAAAACG     120

GATACAGGTG GTGATCTAAC CCTAGACGAA ATTTTAAAGA ATCAGCAGTT ACTAAATGAT     180

ATTTCTGGTA AATTGGATGG GGTGAATGGA AGCTTAAATG ATCTTATCGC ACAGGGAAAC     240

TTAAATACAG AATTATCTAA GGAAATATTA AAAATTGCAA ATGAACAAAA TCAAGTTTTA     300

AATGAGGTTA ATAACAAACT CGAGGCGATA AGTACGATTT TTCGGGTATA TTTACCTAAA     360

AATACCTCTA GGGGGGGGGG GGTAATGAAA CAAAATTATG CGCTAAGTCT GCAAATGGAA     420

AACTTGAGTA AACAATTACA AGAGATTTCT GTTAAGTGGG ATATTATTAA TGTAAATGTA     480

CTTATTAACT CTACACTTAC CGAAATTACA CCTGCGTATC AAAGGATTAA ATATGTGAAC     540

GAAAAATTTG AGGAATTAAC TTTTGCTACA GAAACTAGTT CAAAAGTAAA AAAGGATGGC     600

TCTCCCGCAG ATATTCTTGA TGAGTTAACT GAGTTAACTG AACTAGCGAA AAGTGTAACA     660

AAAAATGATG TGGATGGTTT TGAATTTTAC CTTAATACAT TCCACGATGT AATGGTAGGA     720

AATAATTTAT TCGGGCGTTC AGCTTTAAAA ACTGCATCGG AATTAATTAC TAAAGAAAAT     780

GTGAAAACAA GTGGCAGTGA GGTCGGAAAT GTTTATAACT TCTTAATTGT ATTAACAGCT     840

CTGCAAGCAA AAGCTTTTCT TACTTTAACA ACATGCCGAA AATTATTAGG CTTAGCAGAT     900

ATTGATTATA CTTCTATTAT GAATGAACAT TTAAATAAGG AAAAGAGGA ATTTAGAGTA      960

AACATCCTCC CTACACTTTC TAATACTTTT TCTAATCCTA ATTATGCAAA AGTTAAAGGA    1020

AGTGATGAAG ATGCAAAGAT GATTGTGGAA GCTAAACCAG ACATGCATT GATTGGGTTT     1080
```

```
GAAATTAGTA ATGATTCAAT TACAGTATTA AAAGTATATG AGGCTAAGCT AAAACAAAAT    1140

TATCAAGTCG ATAAGGATTC CTTATCGGAA GTTATTTATG GTGATATGGA TAAATTATTG    1200

TGCCCAGATC AATCTGAACA AATCTATTAT ACAAATAACA TAGTATTTCC AAATGAATAT    1260

GTAATTACTA AAATTGATTT CACTAAAAAA ATGAAAACTT AAGATATGA GGTAACAGCG     1320

AATTTTTATG ATTCTTCTAC AGGAGAAATT GACTTAAATA AGAAAAAAGT AGAATCAAGT    1380

GAAGCGGAGT ATAGAACGTT AAGTGCTAAT GATGATGGGG TGTATATGCC GTTAGGTGTC    1440

ATCAGTGAAA CATTTTTGAC TCCGATTAAT GGGTTTGGCC TCCAAGCTGA TGAAAATTCA    1500

AGATTAATTA CTTTAACATG TAAATCATAT TTAAGAGAAC TACTGCTAGC AACCGACTTA    1560

AGCAATAAAG AAACTAAATT GATCGTCCCG CCAAGTGGTT TTATTAGCSA TATTGTAGAG    1620

AACGGGTCCA TAGAAGAGGA CAATTTAGAG CCGTGGAAAA CAAATAATAA GAATGCGTAT    1680

GTAGATCATA CAGGCGGAGT GAATGGAACT AAAGCTTTAT ATGTTCATAA GGACGGAGGA    1740

ATTTCACAAT TTATTGGAGA TAAGTTAAAA CCGAAAACTG AGTATGTAAT CCAATATACT    1800

GTTAAAGGAA AACCTTCTAT TCATTTAAAA GATGAAAATA CTGGATATAT TCATTATGAA    1860

GATACAAATA ATAATTTAGA AGATTATCAA ACTATTAATA AACGTTTTAC TACAGGAACT    1920

GATTTAAAGG GAGTGTATTT AATTTTAAAA AGTCAAAATG GAGATGAAGC TTGGGGAGAT    1980

AACTTTATTA TTTTGGAAAT TAGTCCTTCT GAAAAGTTAT TAAGTCCAGA ATTAATTAAT    2040

ACAAATAATT GGACGAGTAC GGGATCAACT AATATTAGCG GTAATACACT CACTCTTTAT    2100

CAGGGAGGAC GAGGGATTCT AAAACAAAAC CTTCAATTAG ATAGTTTTTC AACTTATAGA    2160

GTGTATTTTT CTGTGTCCGG AGATGCTAAT GTAAGGATTA GAAATTCTAG GGAAGTGTTA    2220

TTTGAAAAAA GATATATGAG CGGTGCTAAA GATGTTTCTG AAATGTTCAC TACAAAATTT    2280

GAGAAAGATA ACTTTTATAT AGAGCTTTCT CAAGGGAATA ATTTATATGG TGGTCCTATT    2340

GTTCATTTTT ACGATGTCTC TATTAAGTAA CCCAA                               2375
```

(2) INFORMATION FOR SEQ ID NO: 82:

(i) SEQUENCE CHARACTERISTICS:
       (A) LENGTH: 789 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 82:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
```

-continued

```
            115                 120                 125
Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
                180                 185                 190

Thr Leu Lys Val Lys Lys Asp Ser Ser Pro Ala Asp Ile Leu Asp Glu
            195                 200                 205

Leu Thr Glu Leu Thr Glu Leu Ala Lys Ser Val Thr Lys Asn Asp Val
            210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
                260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
            290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly Tyr Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
            370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Gly Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Leu Pro Ser Gly Phe Ile Ser Asn Ile Val Glu Asn Gly Ser Ile
            530                 535                 540
```

-continued

```
Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr His Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Asn
    770                 775                 780

Asp Val Ser Ile Lys
785
```

(2) INFORMATION FOR SEQ ID NO: 83:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 83:

```
ATGAACAAGA ATAATACTAA ATTAAGCACA AGAGCCTTAC CAAGTTTTAT TGATTATTTT      60

AATGGCATTT ATGGATTTGC CACTGGTATC AAAGACATTA TGAATATGAT TTTTAAAACG     120

GATACAGGTG GTAATCTAAC CTTAGATGAA ATCCTAAAGA ATCAGCAGTT ACTAAATGAG     180

ATTTCTGGTA AATTGGATGG GGTAAATGGG AGCTTAAATG ATCTTATCGC ACAGGGAAAC     240

TTAAATACAG AATTATCTAA GGAAATCTTA AAAATTGCAA ATGAACAGAA TCAAGTCTTA     300

AATGATGTTA ATAACAAACT CGATGCGATA AATACGATGC TTCATATATA TCTACCTAAA     360

ATTACATCTA TGTTAAGTGA TGTAATGAAG CAAAATTATG CGCTAAGTCT GCAAATAGAA     420

TACTTAAGTA AACAATTGCA AGAAATTTCT GATAAATTAG ATATTATTAA CGTAAATGTT     480

CTTATTAACT CTACACTTAC TGAAATTACA CCTGCATATC AACGGATTAA ATATGTGAAT     540
```

```
GAAAAATTTG AAGAATTAAC TTTTGCTACA GAAACCACTT TAAAAGTAAA AAAGGATAGC      600

TCGCCTGCTG ATATTCTTGA TGAGTTAACT GAATTAACTG AACTAGCGAA AAGTGTTACA      660

AAAAATGACG TGGATGGTTT TGAATTTTAC CTTAATACAT TCCACGATGT AATGGTAGGA      720

AATAATTTAT TCGGGCGTTC AGCTTTAAAA ACTGCTTCAG AATTAATTGC TAAAGAAAAT      780

GTGAAAACAA GTGGCAGTGA AGTAGGAAAT GTTTATAACT TCTTAATTGT ATTAACAGCT      840

CTACAAGCAA AAGCTTTTCT TACTTTAACA ACATGCCGAA AATTATTAGG CTTAGCAGAT      900

ATTGATTATA CTTCTATTAT GAATGAACAT TTAAATAAGG AAAAAGAGGA ATTTAGAGTA      960

AACATCCTTC CTACACTTTC TAATACTTTT TCTAATCCTA ATTATGCAAA AGTTAAAGGA     1020

AGTGATGAAG ATGCAAAGAT GATTGTGGAA GCTAAACCAG ATATGCATT GGTTGGGTTT      1080

GAAATGAGCA ATGATTCAAT CACAGTATTA AAAGTATATG AGGCTAAGCT AAAACAAAAT     1140

TATCAAGTTG ATAAGGATTC CTTATCGGAA GTTATTTATG GTGATACGGA TAAATTATTG     1200

TGTCCAGATC AATCTGAACA AATATATTAT ACAAATAACA TAGTATTTCC AAATGAATAT     1260

GTAATTACTA AAATTGATTT CACTAAAAAA ATGAAAACTT TAAGATATGA GGTAACAGCG     1320

AATTTTTATG ATTCTTCTAC AGGAGAAATT GACTTAAATA AGAAAAAAGT AGAATCAAGT     1380

GAAGCGGAGT ATAGAACGTT AAGTGCTAAT GATGATGGAG TGTATATGCC ATTAGGTGTC     1440

ATCAGTGAAA CATTTTTGAC TCCGATAAAT GGGTTTGGCC TCCAAGCTGA TGGAAATTCA     1500

AGATTAATTA CTTTAACATG TAAATCATAT TTAAGAGAAC TACTGCTAGC AACAGACTTA     1560

AGCAATAAAG AAACTAAATT GATCGTCCTG CCAAGTGGTT TTATTAGCAA TATTGTAGAG     1620

AACGGGTCCA TAGAAGAGGA CAATTTAGAG CCGTGGAAAG CAAATAATAA GAATGCGTAT     1680

GTAGATCATA CAGGCGGAGT GAATGGAACT AAAGCTTTAT ATGTTCATAA GGACGGAGGA     1740

TTTTCACAAT TTATTGGAGA TAAGTTAAAA CCGAAAACTG AGTATGTAAT CCAATATACT     1800

GTTAAAGGAA AACCTTCTAT TCATTTAAAA GATGAAAATA CTGGATATAT TCATTATGAA     1860

GATACAAATA ATAATTTAAA AGATTATCAA ACTATTACTA AACGTTTTAC TACAGGAACT     1920

GATTTAAAGG GAGTGTATTT AATTTTAAAA AGTCAAAATG GAGATGAAGC TTGGGGAGAT     1980

AACTTTATTA TTTTGGAAAT TAGTCCTTCT GAAAAGTTAT TAAGTCCAGA ATTAATTAAT     2040

ACAAATAATT GGACGAGTAC GGGATCAACT CATATTAGCG GTAATACACT CACTCTTTAT     2100

CAGGGAGGAC GAGGAATTCT AAAACAAAAC CTTCAATTAG ATAGTTTTTC AACTTATAGA     2160

GTGTATTTTT CTGTGTCCGG AGATGCTAAT GTAAGGATTA GAAATTCTAG GGAAGTGTTA     2220

TTTGAAAAAA GATATATGAG CGGTGCTAAA GATGTTTCTG AAATGTTCAC TACAAAATTT     2280

GAGAAAGATA ACTTTTATAT AGAGCTTTCT CAAGGGAATA ATTTATATGG TGGTCCTATT     2340

GTACATTTTA ACGATGTCTC TATTAAGTAA CCCAA                                2375

(2) INFORMATION FOR SEQ ID NO: 84:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 84:

Met Asn Lys Asn Asn Thr Lys Leu Ser Ala Arg Ala Leu Pro Ser Phe
1               5                   10                  15
```

```
Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asn Leu Thr Leu
                 35                  40                  45

Asp Glu Ile Leu Lys Asn Gln Gln Leu Leu Asn Glu Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
             100                 105                 110

Met Leu His Ile Tyr Leu Pro Lys Ile Thr Ser Met Leu Ser Asp Val
             115                 120                 125

Met Lys Gln Asn Tyr Ala Leu Ser Leu Gln Ile Glu Tyr Leu Ser Lys
 130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                 165                 170                 175

Lys Tyr Val Asn Glu Lys Phe Glu Glu Leu Thr Phe Ala Thr Glu Thr
             180                 185                 190

Ser Ser Lys Val Lys Lys Asp Ser Pro Pro Ala Asp Ile Leu Asp Glu
             195                 200                 205

Leu Thr Glu Leu Thr Glu Leu Ala Lys Ser Val Thr Lys Asn Asp Val
     210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
             245                 250                 255

Ala Lys Glu Asn Val Lys Thr Ser Gly Ser Glu Val Gly Asn Val Tyr
             260                 265                 270

Asn Phe Leu Ile Val Leu Thr Ala Leu Gln Ala Lys Ala Phe Leu Thr
             275                 280                 285

Leu Thr Thr Cys Arg Lys Leu Leu Gly Leu Ala Asp Ile Asp Tyr Thr
     290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                 325                 330                 335

Lys Val Lys Gly Ser Asp Glu Asp Ala Lys Met Ile Val Glu Ala Lys
             340                 345                 350

Pro Gly Tyr Ala Leu Val Gly Phe Glu Met Ser Asn Asp Ser Ile Thr
             355                 360                 365

Val Leu Lys Val Tyr Glu Ala Lys Leu Lys Gln Asn Tyr Gln Val Asp
     370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Tyr Thr Asn Asn Ile Val Phe
             405                 410                 415

Pro Asn Glu Tyr Val Ile Thr Lys Ile Asp Phe Thr Lys Lys Met Lys
             420                 425                 430

Thr Leu Arg Tyr Glu Val Thr Ala Asn Phe Tyr Asp Ser Ser Thr Gly
```

-continued

```
            435                 440                 445
Glu Ile Asp Leu Asn Lys Lys Val Glu Ser Ser Glu Ala Glu Tyr
450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Gly Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
                515                 520                 525

Val Pro Pro Ser Gly Phe Ile Ser Asn Ile Val Glu Asn Gly Ser Ile
            530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
                595                 600                 605

Leu Lys Asp Glu Asn Thr Gly Tyr Ile His Tyr Glu Asp Thr Asn Asn
            610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
                675                 680                 685

Ser Thr His Ile Ser Gly Asn Thr Leu Thr Leu Tyr Gln Gly Gly Arg
            690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Gly Tyr Met Ser Gly Ala Lys Asp Val
                740                 745                 750

Ser Glu Met Phe Thr Thr Lys Phe Glu Lys Asp Asn Phe Tyr Ile Glu
                755                 760                 765

Leu Ser Gln Gly Asn Asn Leu Tyr Gly Gly Pro Ile Val His Phe Tyr
770                 775                 780

Asp Val Ser Ile Lys
785
```

(2) INFORMATION FOR SEQ ID NO: 85:

(i) SEQUENCE CHARACTERISTICS:
        (A) LENGTH: 2375 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 85:

```
ATGAACAAGA ATAATACTAA ATTAAGCGCA AGGGCCCTAC CGAGTTTTAT TGATTATTTT    60
AATGGCATTT ATGGATTTGC CACTGGTATC AAAGACATTA TGAATATGAT TTTTAAAACG   120
GATACAGGTG GTAATCTAAC CTTAGATGAA ATCCTAAAGA ATCAGCAGTT ACTAAATGAG   180
ATTTCTGGTA AATTGGATGG GGTAAATGGG AGCTTAAATG ATCTTATCGC ACAGGGAAAC   240
TTAAATACAG AATTATCTAA GGAAATCTTA AAAATTGCAA ATGAACAGAA TCAAGTCTTA   300
AATGATGTTA ATAACAAACT CGATGCGATA ATACGATGC TTCATATATA TCTACCTAAA    360
ATTACATCTA TGTTAAGTGA TGTAATGAAA CAAAATTATG CGCTAAGTCT GCAAATAGAA   420
TACTTAAGTA AACAATTGCA AGAAATTTCT GATAAATTAG ATATTATTAA CGTAAATGTC   480
CTTATTAACT CTACACTTAC TGAAATTACA CCTGCATATC AACGGATTAA ATATGTGAAT   540
GAAAATTTG AAGAATTAAC TTTTGCTACA GAAACTAGTT CAAAAGTAAA AAAGGATAGC    600
CCCCCTGCTG ATATTCTTGA TGAGTTAACT GAATTAACTG AACTAGCGAA AAGTGTAACA   660
AAAAATGACG TGGATGGTTT TGAATTTTAC CTAATACAT TCCACGATGT AATGGTAGGA    720
AATAATTTAT TCGGGCGTTC AGCTTTAAAA ACTGCTTCAG AATTAATTGC TAAAGAAAAT   780
GTGAAAACAA GTGGCAGTGA AGTAGGAAAT GTTTATAATT TCTTAATTGT ATTAACAGCT   840
CTACAAGCAA AAGCTTTTCT TACTTTAACA ACATGCCGAA AATTATTAGG CTTAGCAGAT   900
ATTGATTATA CTTCTATTAT GAATGAACAT TTAAATAAGG AAAAGAGGA ATTTAGAGTA    960
AACATCCTTC CTACACTTTC TAATACTTTT TCTAATCCTA ATTATGCAAA AGTTAAAGGA  1020
AGTGATGAAG ATGCAAAGAT GATTGTGGAA GCTAAACCAG GATATGCATT GGTTGGTTTT  1080
GAAATGAGCA ATGATTCAAT CACAGTATTA AAAGTATATG AGGCTAAGCT AAAACAAAAT  1140
TATCAAGTTG ATAAGGATTC CTTATCGGAG GTTATTTATG GTGATACGGA TAAATTATTG  1200
TGTCCAGATC AATCTGAACA AATATATTAT ACAAATAACA TAGTATTTCC AAATGAATAT  1260
GTAATTACTA AAATTGATTT CACTAAAAAA ATGAAAACTT TAAGATATGA GGTAACAGCG  1320
AATTTTTATG ATTCTTCTAC AGGAGAAATT GACTTAAATA AGAAAAAAGT AGAATCAAGT  1380
GAAGCGGAGT ATAGAACGTT AAGTGCTAAT GATGATGGAG TGTATATGCC ATTAGGTGTC  1440
ATCAGTGAAA CATTTTTGAC TCCGATAAAT GGGTTTGGCC TCCAAGCTGA TGGAAATTCA  1500
AGATTAATTA CTTTAACATG TAAATCATAT TTAAGAGAAC TACTGCTAGC AACAGACTTA  1560
AGCAATAAAG AAACTAAATT GATCGTCCCG CCAAGTGGTT TTATTAGCAA TATTGTAGAG  1620
AACGGGTCCA TAGAAGAGGA CAATTTAGAG CCGTGGAAAG CAAATAATAA GAATGCGTAT  1680
GTAGATCATA CAGGCGGAGT GAATGGAACT AAAGCTTTAT ATGTTCATAA GGACGGAGGA  1740
TTTTCACAAT TTATTGGAGA TAAGTTAAAA CCGAAAACTG AGTATGTAAT CCAATATACT  1800
GTTAAAGGAA AACCTTCTAT TCATTTAAAA GATGAAAATA CTGGATATAT TCATTATGAA  1860
GATACAAATA ATAATTTAAA AGATTATCAA ACTATTACTA AACGTTTTAC TACAGGAACT  1920
GATTTAAAGG GAGTGTATTT AATTTTAAAA AGTCAAAATG GAGATGAAGC TTGGGGAGAT  1980
AACTTTATTA TTTTGGAAAT TAGTCCTTCT GAAAAGTTAT TAAGTCCAGA ATTAATTAAT  2040
ACAAATAATT GGACGAGTAC GGGATCAACT CATATTAGCG GTAATACACT CACTCTTTAT  2100
CAGGGAGGAC GAGGAATTCT AAAACAAAAC CTTCAATTAG ATAGTTTTTC AACTTATAGA  2160
GTGTATTTTT CTGTGTCCGG AGATGCTAAT GTAAGGATTA GAAATTCTAG GGAAGTGTTA  2220
TTTGAAAAAG GATATATGAG CGGTGCTAAA GATGTTTCTG AAATGTTCAC TACAAAATTT  2280
GAGAAAGATA ACTTTTATAT AGAGCTTTCT CAAGGGAATA ATTTATATGG TGGTCCTATT  2340
```

-continued

```
GTACATTTTT ACGATGTCTC TATTAAGTAA CCAAG                                    2375
```

(2) INFORMATION FOR SEQ ID NO: 86:

(i) SEQUENCE CHARACTERISTICS:
        (A) LENGTH: 759 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 86:

```
Met Asn Lys Asn Asn Thr Lys Leu Ser Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Ile Tyr Leu Pro Lys Ile Thr Ser Met Leu Ser Asp Val
        115                 120                 125

Met Asn Gln Asn Tyr Ala Leu Ser Leu Gln Ile Glu Tyr Leu Ser Lys
130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Xaa Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
210                 215                 220

Asp Gly Phe Glu Ile Tyr Leu Asn Thr Phe His Asp Val Met Val Gly
225                 230                 235                 240

Asn Asn Leu Ile Gly Arg Ser Ala Leu Lys Thr Ala Ser Glu Leu Ile
                245                 250                 255

Xaa Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335
```

-continued

```
Lys Val Lys Gly Ser Asp Glu Asp Ala Lys Met Ile Val Glu Ala Lys
                340                 345                 350

Pro Gly Tyr Ala Leu Val Gly Phe Glu Met Ser Asn Asp Ser Ile Thr
            355                 360                 365

Val Leu Lys Val Tyr Glu Ala Lys Leu Lys Gln Asn Tyr Gln Val Asp
        370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Thr Asn Asn Ile Val Phe
                405                 410                 415

Pro Asn Glu Tyr Val Ile Thr Lys Ile Asp Phe Thr Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser His
        530                 535                 540

Arg Arg Gly Gln Phe Arg Ala Val Glu Ser Lys Glu Cys Val Cys Arg
545                 550                 555                 560

Ser Tyr Arg Arg Ser Glu Trp Asn Ser Phe Ile Cys Ser Gly Arg Arg
                565                 570                 575

Asn Phe Thr Ile Tyr Trp Arg Val Lys Thr Glu Asn Val Cys Asn Pro
                580                 585                 590

Ile Tyr Cys Arg Lys Thr Phe Tyr Ser Phe Lys Arg Lys Tyr Trp Ile
            595                 600                 605

Tyr Ser Leu Arg Tyr Lys Phe Lys Arg Leu Ser Asn Tyr Tyr Thr Phe
        610                 615                 620

Tyr Tyr Arg Asn Phe Lys Gly Ser Val Phe Asn Phe Lys Lys Ser Lys
625                 630                 635                 640

Trp Arg Ser Leu Gly Arg Leu Tyr Tyr Phe Gly Asn Ser Phe Lys Val
                645                 650                 655

Ile Lys Ser Arg Ile Asn Tyr Lys Leu Asp Glu Tyr Gly Ile Asn Ser
                660                 665                 670

Tyr Arg Tyr Thr His Ser Leu Ser Gly Arg Thr Arg Asn Ser Lys Thr
            675                 680                 685

Lys Pro Ser Ile Arg Phe Phe Asn Leu Ser Val Phe Cys Val Arg
        690                 695                 700

Arg Cys Cys Lys Asp Lys Phe Gly Ser Val Ile Lys Lys Ile Tyr Glu
705                 710                 715                 720

Arg Cys Arg Cys Phe Asn Val His Tyr Lys Ile Glu Arg Leu Leu Tyr
                725                 730                 735

Arg Ala Phe Ser Arg Glu Phe Ile Trp Trp Ser Tyr Cys Thr Phe Leu
            740                 745                 750

Arg Cys Leu Tyr Val Thr Gln
```

(2) INFORMATION FOR SEQ ID NO: 87:

(i) SEQUENCE CHARACTERISTICS:
        (A) LENGTH: 2376 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 87:

```
ATGAACAAGA ATAATACTAA ATTAAGCGCA AGAGCCCTAC CGAGTTTTAT TGATTATTTT      60
AATGGCATTT ATGGATTTGC CACTGGTATC AAAGACATTA TGAATATGAT TTTTAAAACG     120
GATACAGGTG GTAATCTAAC CTTAGATGAA ATCCTAAAGA ATCAGCAGTT ACTAAATGAG     180
ATTTCTGGTA AATTGGATGG GGTAAATGGG AGCTTAAATG ATCTTATCGC ACAGGGAAAC     240
TTAAATACAG AATTATCTAA GGAAATCTTA AAAATTGCAA ATGAACAAAA TCAAGTCTTA     300
AATGATGTTA ATAACAAACT CGATGCGATA ATACGATGC TTCGGATATA TCTACCTAAA      360
ATTACATCTA TGTTAAGTGA TGTAATGAAC CAAAATTATG CGCTAAGTCT GCAAATAGAA     420
TACTTAAGTA AACAATTGCA AGAAATTTCT GATAAATTGG ATATTATTAA TGTAAATGTA     480
CTTATTAACT CTACACTTAC TGAAATTACA CCTGCGTATC AAAGGATTAA ATATGTGAAC     540
GAAAAATTTG AGGAATTAAC TTTTGCTACA GAAACTAKTT CAAAAGTAAA AAAGGATGGC     600
TCTCCTGCAG ATATTCTTGA TGAGTTAACT GAGTTAACTG AACTAGCGAA AAGTGTAACA     660
AAAAATGATG TGGATGGTTT TGAAATTTAC CTTAATACAT TCCACGATGT AATGGTAGGA     720
AATAATTTAA TCGGGCGTTC AGCTTTAAAA ACTGCATCGG AATTAATTAS TAAAGAAAAT     780
GTGAAAACAA GTGGCAGTGA GGTAGGAAAT GTTTATAACT TCTTAATTGT ATTAACAGCT     840
CTACAAGCAA AAGCTTTTCT TACTTTAACA ACATGCCGAA ATTATTAGG CTTAGCAGAT      900
ATTGATTATA CTTCTATTAT GAATGAACAT TTAAATAAGG AAAAGAGGA ATTTAGAGTA      960
AACATCCTTC CTACACTTTC TAATACTTTT TCTAATCCTA ATTATGCAAA AGTTAAAGGA    1020
AGTGATGAAG ATGCAAAGAT GATTGTGGAA GCTAAACCAG GATATGCATT GGTTGGTTTT    1080
GAAATGAGCA ATGATTCAAT CACAGTATTA AAAGTATATG AGGCTAAGCT AAAACAAAAT    1140
TATCAAGTTG ATAAGGATTC CTTATCGGAG GTTATTTATG GTGATACGGA TAAATTATTG    1200
TGTCCAGATC AATCTGAACA AATATATTAT ACAAATAACA TAGTATTTCC AAATGAATAT    1260
GTAATTACTA AAATTGATTT CACTAAAAAA ATGAAAACTT TAAGATATGA GGTAACAGCG    1320
AATTTTTATG ATTCTTCTAC AGGAGAAATT GACTTAAATA AGAAAAAGT AGAATCAAGT     1380
GAAGCGGAGT ATAGAACGTT AAGTGCTAAT GATGATGGAG TGTATATGCC GTTAGGTGTC    1440
ATCAGTGAAA CATTTTTGAC TCCGATTAAT GGGTTTGGCC TCCAAGCTGA TGAAAATTCA    1500
AGATTAATTA CTTTAACATG TAAATCATAT TTAAGAGAAC TACTGCTAGC AACAGACTTA    1560
AGCAATAAAG AAACTAAATT GATCGTCCCG CCAAGTGGTT TTATTAGCAA TATTGTAGAG    1620
AACGGGTCCC ATAGAAGAGG ACAATTTAGA GCCGTGGAAA GCAAATAATA AGAATGCGTA    1680
TGTAGATCAT ACAGGCGGAG TGAATGGAAC TAAAGCTTTA TATGTTCATA AGGACGGAGG    1740
AATTTCACAA TTTATTGGAG ATAAGTTAAA ACCGAAAACT GAGTATGTAA TCCAATATAC    1800
TGTTAAAGGA AAACCTTCTA TTCATTTAAA AGATGAAAAT ACTGGATATA TTCATTATGA    1860
AGATACAAAT AATAATTTAA AAGATTATCA AACTATTACT AAACGTTTTA CTACAGGAAC    1920
```

```
TGATTTAAAG GGAGTGTATT TAATTTTAAA AAGTCAAAAT GGAGATGAAG CTTGGGGAGA    1980

TAACTTTATT ATTTTGGAAA TTAGTCCTTC TGAAAAGTTA TTAAGTCCAG AATTAATTAA    2040

TACAAATAAT TGGACGAGTA CGGGATCAAC TCATATTAGC GGTAATACAC TCACTCTTTA    2100

TCAGGGAGGA CGAGGAATTC TAAAACAAAA CCTTCAATTA GATAGTTTTT CAACTTATAG    2160

AGTGTATTTT TCTGTGTCCG AGATGCTAA TGTAAGGATT AGAAATTCTA GGGAAGTGTT     2220

ATTTGAAAAA AGATATATGA GCGGTGCTAA AGATGTTTCT GAAATGTTCA CTACAAAATT    2280

TGAGAAAGAT AACTTTTATA TAGAGCTTTC TCAAGGGAAT AATTTATATG GTGGTCCTAT    2340

TGTACATTTT TACGATGTCT CTATTAAGTA ACCCAA                              2376
```

(2) INFORMATION FOR SEQ ID NO: 88:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 88:

```
Tyr Leu Ser Lys Gln Leu Gln Glu Ile Ser Asp Lys Leu Asp Ile Ile
1               5                   10                  15

Asn Val Asn Val Leu Ile Asn Ser Thr Leu Thr Glu Ile Thr Pro Ala
            20                  25                  30

Tyr Gln Arg Ile Lys Tyr Val Asn Glu Lys Phe Glu Glu Leu Thr Phe
        35                  40                  45

Ala Thr Glu Thr Thr Leu Lys Val Lys Lys Asp Ser Ser Pro Ala Asp
    50                  55                  60

Ile Leu Asp Glu Leu Thr Glu Leu Thr Glu Leu Ala Lys Ser Val Thr
65                  70                  75                  80

Lys Asn Asp Val Asp Gly Phe Glu Phe Tyr Leu Asn Thr Phe His Asp
                85                  90                  95

Val Met Val Gly Asn Asn Leu Phe Gly Arg Ser Ala Leu Lys Thr Ala
            100                 105                 110

Ser Glu Leu Ile Ala Lys Glu Asn Val Lys Thr Ser Gly Ser Glu Val
        115                 120                 125

Gly Asn Val Tyr Asn Phe Leu Ile Val Leu Thr Ala Leu Gln Ala Lys
    130                 135                 140

Ala Phe Leu Thr Leu Thr Thr Cys Arg Lys Leu Leu Gly Leu Ala Asp
145                 150                 155                 160

Ile Asp Tyr Thr Ser Ile Met Asn Glu His Leu Asn Lys Glu Lys Glu
                165                 170                 175

Glu Phe Arg Val Asn Ile Leu Pro Thr Leu Ser Asn Thr Phe Ser Asn
            180                 185                 190

Pro Asn Tyr Ala Lys Val Lys Gly Ser Asp Glu Asp Ala Lys Met Ile
        195                 200                 205

Val Glu Ala Lys Pro Gly Tyr Ala Leu Val Gly Phe Glu Met Ser Asn
    210                 215                 220

Asp Ser Ile Thr Val Leu Lys Val Tyr Glu Ala Lys Leu Lys Gln Asn
225                 230                 235                 240

Tyr Gln Val Asp Lys Asp Pro Leu Ser Glu Val Ile Tyr Gly Asp Thr
                245                 250                 255

Asp Lys Leu Leu Cys Pro Asp Gln Ser Glu Gln Ile Tyr Tyr Thr Asn
            260                 265                 270
```

```
Asn Ile Val Phe Pro Asn Glu Tyr Val Ile Thr Lys Ile Asp Phe Thr
            275                 280                 285
Lys Lys Met Lys Thr Leu Arg Tyr Glu Val Thr Ala Asn Phe Tyr Asp
        290                 295                 300
Ser Ser Thr Gly Glu Ile Asp Leu Asn Lys Lys Val Glu Ser Ser
305                 310                 315                 320
Glu Ala Glu Tyr Arg Thr Leu Ser Ala Asn Asp Asp Gly Val Tyr Met
                325                 330                 335
Pro Leu Gly Val Ile Ser Glu Thr Phe Leu Thr Pro Ile Asn Gly Phe
            340                 345                 350
Gly Leu Gln Ala Asp Gly Asn Ser Arg Leu Ile Thr Leu Thr Cys Lys
        355                 360                 365
Ser Tyr Leu Arg Glu Leu Leu Leu Ala Thr Asp Leu Ser Asn Lys Glu
        370                 375                 380
Thr Lys Leu Ile Val Pro Pro Ser Gly Phe Ile Ser Asn Ile Val Glu
385                 390                 395                 400
Asn Gly Ser Ile Glu Glu Asp Asn Leu Glu Pro Trp Lys Ala Asn Asn
                405                 410                 415
Lys Asn Ala Tyr Val Asp His Thr Gly Gly Val Asn Gly Thr Lys Ala
            420                 425                 430
Leu Tyr Val His Lys Asp Gly Ile Ser Gln Phe Ile Gly Asp Lys
        435                 440                 445
Leu Lys Pro Lys Thr Glu Tyr Val Ile Gln Tyr Thr Val Lys Gly Lys
    450                 455                 460
Pro Ser Ile His Leu Lys Asp Glu Asn Thr Gly Tyr Ile His Tyr Glu
465                 470                 475                 480
Asp Thr Asn Asn Asn Leu Lys Asp Tyr Gln Thr Ile Thr Lys Arg Phe
                485                 490                 495
Thr Thr Gly Thr Asp Leu Lys Gly Val Tyr Leu Ile Leu Lys Ser
            500                 505                 510

(2) INFORMATION FOR SEQ ID NO: 89:

(i) SEQUENCE CHARACTERISTICS:
        (A) LENGTH: 1533 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 89:

TACTTAAGTA AACAATTGCA AGAAATTTCT GATAAATTAG ATATTATTAA CGTAAATGTT     60

CTTATTAACT CTACACTTAC TGAAATTACA CCTGCATATC AACGGATTAA ATATGTGAAT    120

GAAAAATTTG AAGAATTAAC TTTTGCTACA GAAACCACTT TAAAAGTAAA AAAGGATAGC    180

TCGCCTGCTG ATATTCTTGA TGAGTTAACT GAATTAACTG AACTAGCGAA AAGTGTTACA    240

AAAAATGACG TTGATGGTTT TGAATTTTAC CTTAATACAT TCCACGATGT AATGGTAGGA    300

AATAATTTAT TCGGGCGTTC AGCTTTAAAA ACTGCTTCAG AATTAATTGC TAAAGAAAAT    360

GTGAAAACAA GTGGCAGTGA AGTAGGAAAT GTTTATAATT TCTTAATTGT ATTAACAGCT    420

CTACAAGCAA AAGCTTTTCT TACTTTAACA ACATGCCGAA AATTATTAGG CTTAGCAGAT    480

ATTGATTATA CTTCTATTAT GAATGAACAT TTAAATAAGG AAAAAGAGGA ATTTAGAGTA    540

AACATCCTYC CTACACTTTC TAATACTTTT TCTAATCCTA ATTATGCAAA AGTTAAAGGA    600
```

-continued

```
AGTGATGAAG ATGCAAAGAT GATTGTGGAA GCTAAACCAG GATATGCATT GGTTGGTTTT      660

GAAATGAGCA ATGATTCAAT CACAGTATTA AAAGTATATG AGGCTAAGCT AAAACAAAAT      720

TATCAAGTTG ATAAGGATCC CTTATCGGAG GTTATTTATG GTGATACGGA TAAATTATTG      780

TGTCCAGATC AATCTGAACA AATATATTAT ACAAATAACA TAGTATTTCC AAATGAATAT      840

GTAATTACTA AAATTGATTT CACTAAAAAA ATGAAAACTT TAAGATATGA GGTAACAGCG      900

AATTTTTATG ATTCTTCTAC AGGAGAAATT GACTTAAATA AGAAAAAAGT AGAATCAAGT      960

GAAGCGGAGT ATAGAACGTT AAGTGCTAAT GATGATGGAG TGTATATGCC ATTAGGTGTC     1020

ATCAGTGAAA CATTTTTGAC TCCGATTAAT GGGTTTGGCC TCCAAGCTGA TGGAAATTCA     1080

AGATTAATTA CTTTAACATG TAAATCATAT TTAAGAGAAC TACTGCTAGC AACAGACTTA     1140

AGCAATAAAG AAACTAAATT GATCGTCCCG CCAAGTGGTT TTATTAGCAA TATTGTAGAG     1200

AACGGGTCCA TAGAAGAGGA CAATTTAGAG CCGTGGAAAG CAAATAATAA GAATGCGTAT     1260

GTAGATCATA CAGGCGGAGT GAATGGAACT AAAGCTTTAT ATGTTCATAA GGACGGAGGA     1320

ATTTCACAAT TTATTGGAGA TAAGTTAAAA CCGAAAACTG AGTATGTAAT CCAATATACT     1380

GTTAAAGGAA AACCTTCTAT TCATTTAAAA GATGAAAATA CTGGATATAT TCATTATGAA     1440

GATACAAATA ATAATTTAAA AGATTATCAA ACTATTACTA AACGTTTTAC TACAGGAACT     1500

GATTTAAAGG GAGTGTATTT AATTTTAAAA AGT                                 1533
```

(2) INFORMATION FOR SEQ ID NO: 90:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 90:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asp Asn Lys Leu Asp Ala Ile Asn Thr
            100                 105                 110

Met Leu Arg Val Tyr Leu Pro Lys Ile Thr Xaa Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
```

-continued

```
                180                 185                 190
Ser Ser Lys Val Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Pro Gln Ala
                485                 490                 495

Asp Glu Asn Ser Arg Leu Ile Thr Leu Thr Cys Lys Ser Tyr Leu Arg
            500                 505                 510

Lys Leu Leu Leu Ala Thr Asp Phe Ser Asn Lys Glu Thr Lys Leu Ile
        515                 520                 525

Leu Pro Pro Ser Gly Phe Ile Ser Asn Ile Val Xaa Asn Gly Ser Ile
    530                 535                 540

Glu Glu Asp Asn Leu Glu Pro Gly Lys Ala Asn Asn Arg Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605
```

```
Leu Lys Asp Glu Asn Thr Gly Tyr Ile His Tyr Glu Asp Thr Asn Asn
    610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Ile Phe Thr Thr Lys Phe Glu Lys Asp Asn Phe Tyr Ile Glu
        755                 760                 765

Leu Ser Gln Gly Asn Asn Leu Asn Gly Gly Pro Ile Val His Phe Tyr
    770                 775                 780

Asp Val Ser Ile Lys
785

(2) INFORMATION FOR SEQ ID NO: 91:

(i) SEQUENCE CHARACTERISTICS:
        (A) LENGTH: 2367 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 91:

ATGAACAAGA ATAATACTAA ATTAAGCACA AGAGCCTTAC CAAGTTTTAT TGATTATTTT      60

AATGGCATTT ATGGATTTGC CACTGGTATC AAAGACATTA TGAACATGAT TTTTAAAACG     120

GATACAGGTG GTGATCTAAC CCTAGACGAA ATTTTAAAGA ATCAGCAGTT ACTAAATGAT     180

ATTTCTGGTA AATTGGATGG GGTGAATGGA AGCTTAAATG ATCTTATCGC ACAGGGAAAC     240

TTAAATACAG AATTATCTAA AGAAATATTA AAAATTGCAA ATGAACAAAA TCAAGTTTTA     300

AATGATGTTG ATAACAAACT CGATGCGATA AATACGATGC TTCGGGTATA TCTACCTAAA     360

ATTACCCTAT GTTGAGTGAT GTAATGAAAC AAAATTATGC GCTAAGTCTG CAAATAGAAT     420

ACTTAAGTAA ACAATTGCAA GAGATTTCTG ATAAGTTGGA TATTATTAAT GTAAATGTAC     480

TTATTAACTC TACACTTACT GAAATTCACA CTGCGTATCA AAGGATTAAA TATGTGAACG     540

AAAAATTTGA GGAATTAACT TTTGCTACAG AAACTAGTTC AAAAGTAAAA AAGGATGGCT     600

CTCCTGCAGA TATTCTTGAT GAGTTAACTG AGTTAACTGA ACTAGCGAAA AGTGTAACAA     660

AAAATGATGT GGATGGTTTT GAATTTTACC TTAATACATT CCACGATGTA ATGGTAGGAA     720

ATAATTTATT CGGGCGTTCA GCTTTAAAAA CTGCATCGGA ATTAATTACT AAAGAAAATG     780

TGAAAACAAG TGGCAGTGAG GTCGGAAATG TTTATAACTT CTTAATTGTA TTAACAGCTC     840

TGCAAGCAAA AGCTTTTCTT ACTTTAACAA CATGCCGAAA ATTATTAGGC TTAGCAGATA     900
```

```
TTGATTATAC TTCTATTATG AATGAACATT TAAATAAGGA AAAAGAGGAA TTTAGAGTAA      960

ACATCCTCCC TACACTTTCT AATACTTTTT CTAATCCTAA TTATGCAAAA GTTAAAGGAA     1020

GTGATGAAGA TGCAAAGATG ATTGTGGAAG CTAAACCAGG ACATGCATTG GTTGGGTTTG     1080

AAATTAGTAA TGATTCAATT ACAGTATTAA AAGTATATGA GGCTAAGCTA AAACAAAATT     1140

ATCAAGTTGA TAAGGATTCC TTATCGGAAG TTATTTATGG TGATATGGAT AAATTATTGT     1200

GCCCAGATCA ATCTGAACAA ATCTATTATA CAAATAACAT AGTATTTCCA AATGAATATG     1260

TAATTACTAA AATTGATTTT ACTAAAAAAA TGAAACTTT AAGATATGAG GTAACAGCGA      1320

ATTTTTATGA TTCTTCTACA GGAGAAATTG ACTTAAATAA GAAAAAGTA GAATCAAGTG      1380

AAGCGGAGTA TAGAACGTTA AGTGCTAATG ATGATGGAGT GTATATGCCG TTAGGTGTCA     1440

TCAGTGAAAC ATTTTTGACT CCGATTAATG GGTTTGGCCC CCAAGCTGAT GAAAATTCAA     1500

GATTAATTAC TTTAACATGT AAATCATATT TAAGAAAACT ACTGCTAGCA ACAGACTTTA     1560

GCAATAAAGA AACTAAATTG ATCCTCCCGC CAAGTGGTTT TATTAGCAAT ATTGTAGAAA     1620

CGGGTCCATA GAAGAGGACA ATTTAGAGCC GGGGAAAGCA AATAATAGGA ATGCGTATGT     1680

AGATCATACA GGCGGAGTGA ATGGAACTAA AGCTTTATAT GTTCATAAGG ACGGAGGAAT     1740

TTCACAATTT ATTGGAGATA AGTTAAAACC GAAAACTGAG TATGTAATCC AATATACTGT     1800

TAAAGGAAAA CCTTCTATTC ATTTAAAAGA TGAAAATACT GGATATATTC ATTATGAAGA     1860

TACAAATAAT AATTTAGAAG ATTATCAAAC TATTACTAAA CGTTTTACTA CAGGAACTGA     1920

TTTAAAGGGA GTGTATTTAA TTTTAAAAAG TCAAATGGA GATGAAGCTT GGGGAGATAA      1980

CTTTATTATT TTGGAAATTA GTCCTTCTGA AAAGTTATTA AGTCCAGAAT TAATTAATAC     2040

AAATAATTGG ACGAGTACGG GATCAACTAA TATTAGCGGT AATACACTCA CTCTTTATCA     2100

GGGAGGACGA GGAATTCTAA AACAAAACCT TCAATTAGAT AGTTTTTCAA CTTATAGAGT     2160

GTATTTTTCT GTGTCCGGAG ATGCTAATGT AAGGATTAGA AATTCTAGGG AAGTGTTATT     2220

TGAAAAAGA TATATGAGCG GTGCTAAAGA TGTTTCTGAA ATTTTCACTA CAAAATTTGA      2280

GAAAGATAAC TTTTATATAG AGCTTTCTCA AGGGAATAAT TTAAATGGTG GCCCTATTGT     2340

ACATTTTTAC GATGTCTCTA TTAAGTA                                        2367

(2) INFORMATION FOR SEQ ID NO: 92:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 92:

Met Asn Lys Asn Asn Thr Lys Leu Ser Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Gly Gly Val Asn Gly Ser Leu Asn Asp Leu Ile Ala Gln Gly Asn
65                  70                  75                  80
```

-continued

```
Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly Tyr Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Gly Asn Ser Arg Leu Ile Thr Leu Thr Cys Lys Ser Tyr Leu Arg
```

```
                    500             505             510
Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
        610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
            675                 680                 685

Ser Thr His Ile Ser Gly Asn Thr Leu Thr Leu Tyr Gln Gly Gly Arg
        690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
770                 775                 780

Asp Val Ser Ile Lys
785

(2) INFORMATION FOR SEQ ID NO: 93:

(i) SEQUENCE CHARACTERISTICS:
        (A) LENGTH: 2369 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

ATGAACAAGA ATAATACTAA ATTAAGCGCA AGGGCCCTAC CGAGTTTTAT TGATTATTTT      60

AATGGCATTT ATGGATTTGC CACTGGTATC AAAGACATTA TGAATATGAT TTTTAAAACG     120

GATACAGGTG GTAATCTAAC CTTAGATGAA ATCCTAAAGA ATCAGCAGTT ACTAAATGAG     180

ATTTCTGGTA AATTGGGGGG GGTAAATGGG AGCTTAAATG ATCTTATCGC ACAGGGAAAC     240

TTAAATACAG AATTATCTAA GGAAATCTTA AAAATTGCAA ATGAACAAAT CAAGTCTTAA     300
```

-continued

| | | | | | |
|---|---|---|---|---|---|
|ATGATGTTAA|TAACAAACTC|GATGCGATAA|ATACGATGCT|TCATATATAT|CTACCTAAAA|360|
|TTACATCTAT|GTTAAGTGAT|GTAATGAAGC|AAAATTATGC|GCTAAGTCTG|CAAATAGAAT|420|
|ACTTAAGTAA|ACAATTGCAA|GAAATTTCTG|ATAAATTAGA|TATTATTAAC|GTAAATGTTC|480|
|TTATTAACTC|TACACTTACT|GAAATTACAC|CTGCATATCA|ACGGATTAAA|TATGTGAATG|540|
|AAAAATTTGA|AGAATTAACT|TTTGCTACAG|AAACCACTTT|AAAAGTAAAA|AAGGATAGCT|600|
|CGCCTGCTGA|TATTCTTGAT|GAGTTAACTG|AATTAACTGA|ACTAGCGAAA|AGTGTTACAA|660|
|AAAATGACGT|TGATGGTTTT|GAATTTTACC|TTAATACATT|CCACGATGTA|ATGGTAGGAA|720|
|ATAATTTATT|CGGGCGTTCA|GCTTTAAAAA|CTGCTTCAGA|ATTAATTGCT|AAAGAAAATG|780|
|TGAAAACAAG|TGGCAGTGAA|GTAGGAAATG|TTTATAATTT|CTTAATTGTA|TTAACAGCTC|840|
|TACAAGCAAA|AGCTTTTCTT|ACTTAACAA|CATGCCGAAA|ATTATTAGGC|TTAGCAGATA|900|
|TTGATTATAC|TTCTATTATG|AATGAACATT|TAAATAAGGA|AAAAGAGGAA|TTTAGAGTAA|960|
|ACATCCTTCC|TACACTTTCT|AATACTTTTT|CTAATCCTAA|TTATGCAAAA|GTTAAAGGAA|1020|
|GTGATGAAGA|TGCAAAGATG|ATTGTGGAAG|CTAAACCAGG|ATATGCATTG|GTTGGTTTTG|1080|
|AAATGAGCAA|TGATTCAATC|ACAGTATTAA|AAGTATATGA|GGCTAAGCTA|AAACAAAATT|1140|
|ATCAAGTTGA|TAAGGATTCC|TTATCGGAGG|TTATTTATGG|TGATACGGAT|AAATTATTGT|1200|
|GTCCAGATCA|ATCTGAACAA|ATATATTATA|CAAATAACAT|AGTATTTCCA|AATGAATATG|1260|
|TAATTACTAA|AATTGATTTC|ACTAAAAAAA|TGAAAACTTT|AAGATATGAG|GTAACAGCGA|1320|
|ATTTTTATGA|TTCTTCTACA|GGAGAAATTG|ACTTAAATAA|GAAAAAAGTA|GAATCAAGTG|1380|
|AAGCGGAGTA|TAGAACGTTA|AGTGCTAATG|ATGATGGAGT|GTATATGCCA|TTAGGTGTCA|1440|
|TCAGTGAAAC|ATTTTTGACT|CCGATAAATG|GGTTTGGCCT|CCAAGCTGAT|GGAAATTCAA|1500|
|GATTAATTAC|TTTAACATGT|AAATCATATT|TAAGAGAACT|ACTGCTAGCA|ACAGACTTAA|1560|
|GCAATAAAGA|AACTAAATTG|ATTGTCCCGC|CAAGTGGTTT|TATTAGCAAT|ATTGTAGAGA|1620|
|ACGGGTCCAT|AGAAGAGGAC|AATTTAGAGC|CGTGGAAAGC|AAATAATAAG|AATGCGTATG|1680|
|TAGATCATAC|AGGCGGAGTG|AATGGAACTA|AAGCTTTATA|TGTTCATAAG|GACGGAGGAA|1740|
|TTTCACAATT|TATTGGAGAT|AAGTTAAAAC|CGAAAACTGA|GTATGTAATC|CAATATACTG|1800|
|TTAAAGGAAA|ACCTTCTATT|CATTTAAAAG|ATGAAAATAC|TGGATATATT|CATTATGAAG|1860|
|ATACAAATAA|TAATTTAAAA|GATTATCAAA|CTATTACTAA|ACGTTTTACT|ACAGGAACTG|1920|
|ATTTAAAGGG|AGTGTATTTA|ATTTTAAAAA|GTCAAAATGG|AGATGAAGCT|TGGGGAGATA|1980|
|ACTTTATTAT|TTTGGAAATT|AGTCCTTCTG|AAAAGTTATT|AAGTCCAGAA|TTAATTAATA|2040|
|CAAATAATTG|GACGAGTACG|GGATCAACTC|ATATTAGCGG|TAATACACTC|ACTCTTTATC|2100|
|AGGGAGGACG|AGGAATTCTA|AAACAAAACC|TTCAATTAGA|TAGTTTTTCA|ACTTATAGAG|2160|
|TGTATTTTTC|TGTGTCCGGA|GATGCTAATG|TAAGGATTAG|AAATTCTAGG|GAAGTGTTAT|2220|
|TTGAAAAAAG|ATATATGAGC|GGTGCTAAAG|ATGTTTCTGA|AATGTTCACT|ACAAAATTTG|2280|
|AGAAAGATAA|CTTTTATATA|GAGCTTTCTC|AAGGGAATAA|TTTATATGGT|GGTCCTATTG|2340|
|TACATTTTTA|CGATGTCTCT|ATTAAGTAA| | |        |2369|

(2) INFORMATION FOR SEQ ID NO: 94:

(i) SEQUENCE CHARACTERISTICS:
        (A) LENGTH: 789 amino acids
        (B) TYPE: amino acid
        (C) STRANDEDNESS: single
        (D) TOPOLOGY: linear -continued (ii) MOLECULE TYPE: protein (xi) SEQUENCE DESCRIPTION: SEQ ID NO: 94:

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Ala Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400
```

```
Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785
```

(2) INFORMATION FOR SEQ ID NO: 95:

(i) SEQUENCE CHARACTERISTICS:

(A) LENGTH: 2370 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 95:

| | |
|---|---|
| TTGAACAAGA ATAATACTAA ATTAAGCACA AGAGCCTTAC CAAGTTTTAT TGATTATTTT | 60 |
| AATGGCATTT ATGGATTTGC CACTGGTATC AAAGACATTA TGAACATGAT TTTTAAAACG | 120 |
| GATACAGGTG GTGATCTAAC CCTAGACGAA ATTTTAAAGA ATCAGCAGTT ACTAAATGAT | 180 |
| ATTTCTGGTA AATTGGATGG GGTGAATGGA AGCTTAAATG ATCTTATCGC ACAGGGAAAC | 240 |
| TTAAATACAG AATTATCTAA GGAAATATTA AAAATTGCAA ATGAACAAAA TCAAGTTTTA | 300 |
| AATGATGTTA ATAACAAACT CGATGCGATA ATACGATGC TTCGGGTATA TCTACCTAAA | 360 |
| ATTACCTCTA TGTTGAGTGA TGTAATGAAA CAAAATTATG CGCTAAGTCT GCAAATAGAA | 420 |
| TACTTAAGTA AACAATTGCA AGAGATTTCT GATAAGTTGG ATATTATTAA TGTAAATGTA | 480 |
| CTTATTAACT CTACACTTAC TGAAATTACA CCTGCGTATC AAAGGATTAA ATATGTGAAC | 540 |
| GAAAAATTTG AGGAATTAAC TTTTGCTACA GAAACTAGTT CAAAAGTAAA AAAGGATGGC | 600 |
| TCTCCTGCAG ATATTCTTGA TGAGTTAGCT GAGTTAACTG AACTAGCGAA AAGTGTAACA | 660 |
| AAAAATGATG TGGATGGTTT TGAATTTTAC CTTAATACAT TCCACGATGT AATGGTAGGA | 720 |
| AATAATTTAT TCGGGCGTTC AGCTTTAAAA ACTGCATCGG AATTAATTAC TAAAGAAAAT | 780 |
| GTGAAAACAA GTGGCAGTGA GGTCGGAAAT GTTTATAACT TCTTAATTGT ATTAACAGCT | 840 |
| CTGCAAGCAA AAGCTTTTCT TACTTTAACA ACATGCCGAA AATTATTAGG CTTAGCAGAT | 900 |
| ATTGATTATA CTTCTATTAT GAATGAACAT TTAAATAAGG AAAAGAGGA ATTTAGAGTA | 960 |
| AACATCCTCC CTACACTTTC TAATACTTTT TCTAATCCTA ATTATGCAAA AGTTAAAGGA | 1020 |
| AGTGATGAAG ATGCAAAGAT GATTGTGGAA GCTAAACCAG GACATGCATT GATTGGGTTT | 1080 |
| GAAATTAGTA ATGATTCAAT TACAGTATTA AAAGTATATG AGGCTAAGCT AAAACAAAAT | 1140 |
| TATCAAGTCG ATAAGGATTC CTTATCGGAA GTTATTTATG GTGATATGGA TAAATTATTG | 1200 |
| TGCCCAGATC AATCTGAACA AATCTATTAT ACAAATAACA TAGTATTTCC AAATGAATAT | 1260 |
| GTAATTACTA AAATTGATTT CACTAAAAAA ATGAAAACTT TAAGATATGA GGTAACAGCG | 1320 |
| AATTTTTATG ATTCTTCTAC AGGAGAAATT GACTTAAATA AGAAAAAGT AGAATCAAGT | 1380 |
| GAAGCGGAGT ATAGAACGTT AAGTGCTAAT GATGATGGGG TGTATATGCC GTTAGGTGTC | 1440 |
| ATCAGTGAAA CATTTTTGAC TCCGATTAAT GGGTTTGGCC TCCAAGCTGA TGAAAATTCA | 1500 |
| AGATTAATTA CTTAACATG TAAATCATAT TTAAGAGAAC TACTGCTAGC AACAGACTTA | 1560 |
| AGCAATAAAG AAACTAAATT GATTGTCCCG CCAAGTGGTT TTATTAGCAA TATTGTAGAG | 1620 |
| AACGGGTCCA TAGAAGAGGA CAATTTAGAG CCGTGGAAAG CAAATAATAA GAATGCGTAT | 1680 |
| GTAGATCATA CAGGCGGAGT GAATGGAACT AAAGCTTTAT ATGTTCATAA GGACGGAGGA | 1740 |
| ATTTCACAAT TTATTGGAGA TAAGTTAAAA CCGAAAACTG AGTATGTAAT CCAATATACT | 1800 |
| GTTAAAGGAA AACCTTCTAT TCATTTAAAA GATGAAAATA CTGGATATAT TCATTATGAA | 1860 |
| GATACAAATA ATAATTTAGA AGATTATCAA ACTATTAATA AACGTTTTAC TACAGGAACT | 1920 |
| GATTTAAAGG GAGTGTATTT AATTTTAAAA AGTCAAAATG GAGATGAAGC TTGGGGAGAT | 1980 |
| AACTTTATTA TTTTGGAAAT TAGTCCTTCT GAAAAGTTAT TAAGTCCAGA ATTAATTAAT | 2040 |
| ACAAATAATT GGACGAGTAC GGGATCAACT AATATTAGCG GTAATACACT CACTCTTTAT | 2100 |

-continued

```
CAGGGAGGAC GAGGGATTCT AAAACAAAAC CTTCAATTAG ATAGTTTTTC AACTTATAGA    2160

GTGTATTTTT CTGTGTCCGG AGATGCTAAT GTAAGGATTA GAAATTCTAG GAAGTGTTA     2220

TTTGAAAAAA GATATATGAG CGGTGCTAAA GATGTTTCTG AAATGTTCAC TACAAAATTT    2280

GAGAAAGATA ACTTTTATAT AGAGCTTTCT CAAGGGAATA ATTTATATGG TGGTCCTATT    2340

GTACATTTTT ACGATGTCTC TATTAAGTAA                                    2370
```

(2) INFORMATION FOR SEQ ID NO: 96:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 96:

```
Met Asn Lys Asn Asn Thr Lys Leu Ser Thr Arg Ala Leu Pro Ser Phe
  1               5                  10                  15

Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asp Leu Thr Leu
         35                  40                  45

Asp Glu Ile Leu Lys Asn Gln Gln Leu Leu Asn Asp Ile Ser Gly Lys
     50                  55                  60

Leu Asp Gly Val Asn Gly Ser Leu Asn Asp Leu Ile Ala Gln Gly Asn
 65                  70                  75                  80

Leu Asn Thr Glu Leu Ser Lys Glu Ile Leu Lys Ile Ala Asn Glu Gln
                 85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300
```

```
Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
            325                 330                 335

Lys Val Lys Gly Ser Asp Glu Asp Ala Lys Met Ile Val Glu Ala Lys
                340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Asn Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720
```

```
Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785

(2) INFORMATION FOR SEQ ID NO: 97:

(i) SEQUENCE CHARACTERISTICS:
        (A) LENGTH: 2374 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:
```

| | | | | | |
|---|---|---|---|---|---|
| ATGAACAAGA | ATAATACTAA | ATTAAGCACA | AGAGCCTTAC | CAAGTTTTAT | TGATTATTTT | 60 |
| AATGGCATTT | ATGGATTTGC | CACTGGTATC | AAAGACATTA | TGAACATGAT | TTTTAAAACG | 120 |
| GATACAGGTG | GTGATCTAAC | CCTAGACGAA | ATTTTAAAGA | ATCAGCAGTT | ACTAAATGAT | 180 |
| ATTTCTGGTA | AATTGGATGG | GGTGAATGGA | AGCTTAAATG | ATCTTATCGC | ACAGGGAAAC | 240 |
| TTAAATACAG | AATTATCTAA | GGAAATATTA | AAAATTGCAA | ATGAACAAAA | TCAAGTTTTA | 300 |
| AATGATGTTA | TAACAAACT | CGATGCGATA | AATACGATGC | TTCGGGTATA | TCTACCTAAA | 360 |
| ATTACCTCTA | TGTTGAGTGA | TGTAATGAAA | CAAAATTATG | CGCTAAGTCT | GCAAATAGAA | 420 |
| TACTTAAGTA | AACAATTGCA | AGAGATTTCT | GATAAGTTGG | ATATTATTAA | TGTAAATGTA | 480 |
| CTTATTAACT | CTACACTTAC | TGAAATTACA | CCTGCGTATC | AAAGGATTAA | ATATGTGAAC | 540 |
| GAAAAATTTG | AGGAATTAAC | TTTTGCTACA | GAAACTAGTT | CAAAAGTAAA | AAAGGATGGC | 600 |
| TCTCCTGCAG | ATATTCTTGA | TGAGTTAACT | GAGTTAACTG | AACTAGCGAA | AAGTGTAACA | 660 |
| AAAAATGATG | TGGATGGTTT | TGAATTTTAC | CTTAATACAT | TCCACGATGT | AATGGTAGGA | 720 |
| AATAATTTAT | TCGGGCGTTC | AGCTTTAAAA | ACTGCATCGG | AATTAATTAC | TAAAGAAAAT | 780 |
| GTGAAAACAA | GTGGCAGTGA | GGTCGGAAAT | GTTTATAACT | TCTTAATTGT | ATTAACAGCT | 840 |
| CTGCAAGCAA | AAGCTTTTCT | TACTTTAACA | ACATGCCGAA | AATTATTAGG | CTTAGCAGAT | 900 |
| ATTGATTATA | CTTCTATTAT | GAATGAACAT | TTAAATAAGG | AAAAAGAGGA | ATTTAGAGTA | 960 |
| AACATCCTCC | CTACACTTTC | TAATACTTTT | TCTAATCCTA | ATTATGCAAA | AGTTAAAGGA | 1020 |
| AGTGATGAAG | ATGCAAAGAT | GATTGTGGAA | GCTAAACCAG | GACATGCATT | GATTGGGTTT | 1080 |
| GAAATTAGTA | ATGATTCAAT | TACAGTATTA | AAAGTATATG | AGGCTAAGCT | AAAACAAAAT | 1140 |
| TATCAAGTCG | ATAAGGATTC | CTTATCGGAA | GTTATTTATG | GTGATATGGA | TAAATTATTG | 1200 |
| TGCCCAGATC | AATCTGAACA | AATCTATTAT | ACAAATAACA | TAGTATTTCC | AAATGAATAT | 1260 |
| GTAATTACTA | AAATTGATTT | CACTAAAAAA | ATGAAAACTT | TAAGATATGA | GGTAACAGCG | 1320 |
| AATTTTTATG | ATTCTTCTAC | AGGAGAAATT | GACTTAAATA | AGAAAAACGT | CGAATCAAGT | 1380 |
| GAAGCGGAGT | ATAGAACGTT | AAGTGCTAAT | GATGATGGGG | TGTATATGCC | GTTAGGTGTC | 1440 |
| ATCAGTGAAA | CATTTTTGAC | TCCGATTAAT | GGGTTTGGCC | TCCAAGCTGA | TGAAAATTCA | 1500 |
| AGATTAATTA | CTTTAACATG | TAAATCATAT | TTAAGAGAAC | TACTGCTAGC | AACAGACTTA | 1560 |

```
AGCAATAAAG AAACTAAATT GATGTCCCGC CAAGTGGTTT TATTAGCAAT ATTGTAGAGA    1620

ACGGGTCCAT AGAAGAGGAC AATTTAGAGC CGTGGAAAGC AAATAATAAG AATGCGTATG    1680

TAGATCATAC AGGCGGAGTG AATGAACTA  AAGCTTTATA TGTTCATAAG GACGGAGGAA    1740

TTTCACAATT TATTGGAGAT AAGTTAAAAC CGAAAACTGA GTATGTAATC CAATATACTG    1800

TTAAAGGAAA ACCTTCTATT CATTTAAAAG ATGAAAATAC TGGATATATT CATTATGAAG    1860

ATACAAATAA TAATTTAGAA GATTATCAAA CTATTAATAA ACGTTTTACT ACAGGAACTG    1920

ATTTAAAGGG AGTGTATTTA ATTTTAAAAA GTCAAAATGG AGATGAAGCT TGGGGAGATA    1980

ACTTTATTAT TTTGGAAATT AGTCCTTCTG AAAAGTTATT AAGTCCAGAA TTAATTAATA    2040

CAAATAATTG GACGAGTACG GGATCAACTA ATATTAGCGG TAATACACTC ACTCTTTATC    2100

AGGGAGGACG AGGGATTCTA AAACAAAACC TTCAATTAGA TAGTTTTTCA ACTTATAGAG    2160

TGTATTTTTC TGTGTCCGGA GATGCTAATG TAAGGATTAG AAATTCTAGG GAAGTGTTAT    2220

TTGAAAAAAG ATATATGAGC GGTGCTAAAG ATGTTTCTGA AATGTTCACT ACAAAATTTG    2280

AGAAAGATAA CTTTTATATA GAGCTTTCTC AAGGGAATAA TTTATATGGT GGTCCTATTG    2340

TACATTTTTA CGATGTCTCT ATTAAGTAAC CCAA                                2374

(2) INFORMATION FOR SEQ ID NO: 98:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 98:

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
130                 135                 140

Gln Leu Xaa Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
```

-continued

```
            195                 200                 205
Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
                260                 265                 270

Asn Phe Leu Ile Val Leu Thr Ala Leu Gln Ala Lys Ala Phe Leu Thr
            275                 280                 285

Leu Thr Thr Cys Xaa Lys Leu Leu Gly Leu Ala Asn Ile Asp Tyr Thr
        290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
                340                 345                 350

Pro Gly Tyr Ala Leu Val Gly Phe Glu Met Ser Asn Asp Ser Ile Thr
                355                 360                 365

Val Leu Lys Val Tyr Glu Ala Lys Leu Lys Gln Asn Tyr Gln Val Asp
        370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Phe Tyr Asp Ser Ser Thr Gly
            435                 440                 445

Glu Ile Asp Leu Asn Lys Lys Lys Val Glu Ser Ser Glu Ala Glu Tyr
        450                 455                 460

Arg Thr Leu Ser Ala Asn Asp Asp Gly Val Tyr Met Pro Leu Gly Val
465                 470                 475                 480

Ile Ser Glu Thr Phe Leu Thr Xaa Ile Xaa Gly Phe Gly Leu Gln Ala
                485                 490                 495

Asp Gly Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
        530                 535                 540

Glu Glu Asp Asn Leu Glu Pro Trp Lys Ala Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Phe Ser Gln Phe Ile Gly Asp Xaa Leu Lys Pro Lys
                580                 585                 590

Thr Glu Tyr Xaa Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
        610                 615                 620
```

```
Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
                675                 680                 685

Ser Thr His Ile Ser Gly Asn Thr Leu Thr Leu Tyr Gln Gly Gly Arg
        690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Met Phe Thr Thr Lys Phe Glu Lys Asp Asn Phe Tyr Ile Glu
                755                 760                 765

Leu Ser Gln Gly Asn Asn Leu Tyr Gly Gly Pro Ile Val His Phe Tyr
                770                 775                 780

Asp Val Ser Ile Lys
785
```

(2) INFORMATION FOR SEQ ID NO: 99:

(i) SEQUENCE CHARACTERISTICS:
        (A) LENGTH: 2366 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

```
ATGAACAAGA ATAATACTAA ATTAAGCACA AGAGCCTTAC CGAGTTTTAT TGATTATTTT      60
AATGGCATTT ATGGATTTGC CACTGGTATC AAAGACATTA TGAATATGAT TTTTAAAACG     120
GATACAGGTG GTAATCTAAC CTTAGATGAA ATCCTAAAGA ATCAGCAGTT ACTAAATGAG     180
ATTTCTGGTA AATTGGATGG GGTAAATGGG AGCTTAAATG ATCTTATCGC ACAGGGAAAC     240
TTAAATACAG AATTATCTAA GGAAATCTTA AAAATTGCAA ATGAACAGAA TCAAGTCTTA     300
AATGATGTTA ATAACAAACT CGATGCGATA AATACGATGC TTCATATATA TCTACCTAAA     360
ATTACATCTA TGTTAAGTGA TGTAATGAAG CAAAATTATG CGCTAAGTCT GCAAATAGAA     420
TACTTAAGTA AACAATTGCA GAATTTCTGA TAAATTAGAT ATTATTAACG TAAATGTTCT     480
TATTAACTCT ACACTTACTG AAATTACACC TGCATATCAA CGGATTAAAT ATGTGAAGAA     540
AAATTTGAAG AATTAACTTT TGCTACAGAA ACCACTTTAA AAGTAAAAAA GGATAGCTCG     600
CCTGCTGATA TTCTTGATGA GTTAACTGAA TTAACTGAAC TAGCGAAAAG TGTTACAAAA     660
AATGACGTTG ATGGTTTTGA ATTTTACCTT AATACATTCC ACGATGTAAT GGTAGGAAAT     720
AATTTATTCG GGCGTTCAGC TTTAAAAACT GCTTCAGAAT TAATTGCTAA AGAAAATGTG     780
AAAACAAGTG GCAGTGAAGT AGGAAATGTT TATAATTTCT TAATTGTATT AACAGCTCTA     840
CAAGCAAAAG CTTTTCTTAC TTTAACAACA TGCCAAAATT ATTAGGCTTA GCAAATATTG     900
ATTATACTTC TATTATGAAT GAACATTTAA ATAAGGAAAA AGAGGAATTT AGAGTAAACA     960
```

```
TCCTTCCTAC ACTTTCTAAT ACTTTTTCTA ATCCTAATTA TGCAAAAGTT AAAGGAAGTG    1020

ATGAAGATGC AAAGATGATT GTGGAAGCTA AACCAGGATA TGCATTGGTT GGTTTTGAAA    1080

TGAGCAATGA TTCAATCACA GTATTAAAAG TATATGAGGC TAAGCTAAAA CAAAATTATC    1140

AAGTTGATAA GGATTCCTTA TCGGAGGTTA TTTATGGTGA TACGGATAAA TTATTGTGTC    1200

CAGATCAATC TGAACAAATA TATTATACAA ATAACATAGT ATTTCCAAAT GAATATGTAA    1260

TTACTAAAAT TGATTTCACT AAAAAAATGA AAACTTTAAG ATATGAGGTA ACAGCGAATT    1320

TTTATGATTC TTCTACAGGA GAAATTGACT TAAATAAGAA AAAAGTAGAA TCAAGTGAAG    1380

CGGAGTATAG AACGTTAAGT GCTAATGATG ATGGAGTGTA TATGCCATTA GGTGTCATCA    1440

GTGAAACATT TTTGACTCGA TTATGGGTTT GGCCTCCAAG CTGATGGAAA TTCAAGATTA    1500

ATTACTTTAA CATGTAAATC ATATTTAAGA GAACTACTGC TAGCAACAGA CTTAAGCAAT    1560

AAAGAAACTA AATTGATTGT CCCCCAAGTG GTTTTATTAG CAATATTGTA GAGAACGGGT    1620

CCATAGAAGA GGACAATTTA GAGCCGTGGA AGCAAATAA TAAGAATGCG TATGTAGATC    1680

ATACAGGCGG AGTGAATGGA ACTAAAGCTT TATATGTTCA TAAGGACGGA GGATTTTCAC    1740

AATTTATTGG AGATAATTAA AACCGAAAAC TGAGTATTAA TCCAATATAC TGTTAAAGGA    1800

AAACCTTCTA TTCATTTAAA AGATGAAAAT ACTGGATATA TTCATTATGA AGATACAAAT    1860

AATAATTTAA AAGATTATCA AACTATTACT AAACGTTTTA CTACAGGAAC TGATTTAAAG    1920

GGAGTGTATT TAATTTTAAA AAGTCAAAAT GGAGATGAAG CTTGGGGAGA TAACTTTATT    1980

ATTTTGGAAA TTAGTCCTTC TGAAAAGTTA TTAAGTCCAG AATTAATTAA TACAAATAAT    2040

TGGACGAGTA CGGGATCAAC TCATATTAGC GGTAATACAC TCACTCTTTA TCAGGGAGGA    2100

CGAGGAATTC TAAAACAAAA CCTTCAATTA GATAGTTTTT CAACTTATAG AGTGTATTTT    2160

TCTGTGTCCG GAGATGCTAA TGTAAGGATT AGAAATTCTA GGGAAGTGTT ATTTGAAAAA    2220

AGATATATGA GCGGTGCTAA AGATGTTTCT GAAATGTTCA CTACAAAATT TGAGAAAGAT    2280

AACTTTTATA TAGAGCTTTC TCAAGGGAAT AATTTATATG GTGGTCCTAT TGTACATTTT    2340

TACGATGTCT CTATTAAGTA ACCCAA                                         2366

(2) INFORMATION FOR SEQ ID NO: 100:

(i) SEQUENCE CHARACTERISTICS:
        (A) LENGTH: 789 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 100:

Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95
```

-continued

```
Asn Gln Val Leu Asn Asp Val Asn Asn Lys Leu Asp Ala Ile Asn Thr
            100                 105                 110

Met Leu Arg Val Tyr Leu Pro Lys Ile Thr Phe Met Leu Ser Asp Val
            115                 120                 125

Met Lys Gln Asn Tyr Ala Leu Ser Leu Gln Ile Glu Tyr Leu Ser Lys
            130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
            195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
            275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Ile Gly Phe Glu Ile Ser Asn Asp Ser Ile Thr
            355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
```

```
                515                 520                 525
Val Pro Pro Ser Gly Phe Ile Ser Asn Ile Val Glu Asn Gly Ser Ile
    530                 535                 540

Glu Glu Asp Asn Leu Glu Pro Trp Lys Ala Xaa Asn Xaa Asn Ala Tyr
545                 550                 555                 560

Val Asp His Thr Gly Val Asn Gly Thr Lys Ala Leu Tyr Val His
                565                 570                 575

Lys Asp Gly Gly Ile Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
    610                 615                 620

Asn Leu Xaa Xaa Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Xaa Glu
                645                 650                 655

Ala Trp Gly Asp Asn Phe Ile Ile Leu Glu Ile Ser Pro Ser Glu Lys
                660                 665                 670

Leu Leu Ser Pro Xaa Leu Ile Asn Thr Xaa Asn Trp Thr Ser Thr Gly
            675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Xaa Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Xaa Val
                740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
    770                 775                 780

Asp Val Ser Ile Lys
785

(2) INFORMATION FOR SEQ ID NO: 101:

(i) SEQUENCE CHARACTERISTICS:
        (A) LENGTH: 2362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 101:

ATGAACAAGA ATAATACTAA ATTAAGCACA AGAGCCTTAC CAAGTTTTAT TGATTATTTT      60

AATGGCATTT ATGGATTTGC CACTGGTATC AAAGACATTA TGAACATGAT TTTTAAAACG     120

GATACAGGTG GTGATCTAAC CCTAGACGAA ATTTTAAGGA ATCAGCAGTT ACTAAATGAT     180

ATTTCTGGTA AATTGGATGG GGTGAATGGA AGCTTAAATG ATCTTATCGC ACAGGGAAAC     240

TTAAATACAG AATTATCTAA GGAAATATTA AAAATTGCAA ATGAACAAAA TCAAGTTTTA     300

AATGATGTTA ATAACAAACT CGATGCGATA AATACGATGC TTCGGGTATA TCTACCTAAA     360

ATTACCTTTA TGTTGAGTGA TGTAATGAAA CAAAATTATG CGCTAAGTCT GCAAATAGAA     420
```

```
TACTTAAGTA AACAATTGCA AGAGATTTCT GATAAGTTGG ATATTATTAA TGTAAATGTA       480

CTTATTAACT CTACACTTAC TGAAATTACA CCTGCGTATC AAAGGATTAA ATATGTGAAC       540

GAAAAATTTG AGGAATTAAC TTTTGCTACA GAAACTAGTT CAAAAGTAAA AAAGGATGGC       600

TCTCCTGCAG ATATTCTTGA TGAGTTAACT GAGTTAACTG AACTAGCGAA AAGTGTAACA       660

AAAAATGATG TGGATGGTTT TGAATTTTAC CTTAATACAT TCCACGATGT AATGGTAGGA       720

AATAATTTAT TCGGGCGTTC AGCTTTAAAA ACTGCATCGG AATTAATTAC TAAAGAAAAT       780

GTGAAAACAA GTGGCAGTGA GGTCGGAAAT GTTTATAACT TCTTAATTGT ATTAACAGCT       840

CTGCAAGCAA AAGCTTTTCT TACTTTAACA ACATGCCGAA AATTATTAGG GTTAGCAGAT       900

ATTGATTATA CTTCTATTAT GAATGAACAT TTAAATAAGG AAAAAGAGGA ATTTAGAGTA       960

AACATCCTCC CTACACTTTC TAATACTTTT TCTAATCCTA ATTATGCAAA AGTTAAAGGA      1020

AGTGATGAAG ATGCAAAGAT GATTGTGGAA GCTAAACCAG GACATGCATT GATTGGGTTT      1080

GAAATTAGTA ATGATTCAAT TACAGTATTA AAAGTATATG AGGCTAAGCT AAAACAAAAT      1140

TATCAAGTCG ATAAGGATTC CTTATCGGAA GTTATTTATG GTGATATGGA TAAATTATTG      1200

TGCCCAGATC AATCTGAACA AATCTATTAT ACAAATAACA TAGTATTTCC AAATGAATAT      1260

GTAATTACTA AAATTGATTT CACTAAAAAA ATGAAAACTT TAAGATATGA GGTAACAGCG      1320

AATTTTTATG ATTCTTCTAC AGGAGAAATT GACTTAAATA AGAAAAAAGT AGAATCAAGT      1380

GAAGCGGAGT ATAGAACGTT AAGTGCTAAT GATGATGGGG TGTATATGCC GTTAGGTGTC      1440

ATCAGTGAAA CATTTTTGAC TCCGATTAAT GGGTTTGGCT CCAAGCTGAT GAAAATTCAA      1500

GATTAATTAC TTTAACATGT AAATCATATT TAAGAGAACT ACTGCTAGCA ACAGACTTAA      1560

GCAATAAAGA AACTAAATTG ATCGTCCCGC CAAGTGGTTT TATTAGCAAT ATTGTAGAGA      1620

ACGGGTCCAT AGAAGAGGAC AATTTAGAGC CCTGGAAAGC AATAATAGAA TGCGTATGTA      1680

GATCATACAG GCGGAGTGAA TGGAACTAAA GCTTTATATG TTCATAAGGA CGGAGGAATT      1740

TCACAATTTA TTGGAGATAA GTTAAAACCG AAAACTGAGT ATGTAATCCA ATATACTGTT      1800

AAAGGAAAAC CTTCTATTCA TTTAAAAGAT GAAAATACTG GATATATTCA TTATGAAGAT      1860

ACAAATAATA ATTTAAATTA TCAAACTATT AATAAACGTT TTACTACAGG AACTGATTTA      1920

AAGGGAGTGT ATTTAATTTT AAAAAGTCAA AATGGAATGA AGCTTGGGGA GATAACTTTA      1980

TTATTTTGGA AATTAGTCCT TCTGAAAAGT TATTAAGTCC AAATTAATTA ATACAATAAT      2040

TGGACAGTAC GGGATCAACT AATATTAGCG GTAAATACACT CACTCTTTAT CAGGGAGGAC      2100

GAGGGATTCT AAAACAAAAC CTTCAATTAG ATAGTTTTCA ACTTATAGAG TGTATTTTTC      2160

TGTGTCCGGA GATGCTAATG TAAGGATTAG AAATTCTAGG GAAGTGTTAT TTGAAAAAAG      2220

ATATATGAGC GGTGCTAAAA TGTTTCTGAA ATGTTCACAC AAAATTTGAG AAAGATAACT      2280

TTTATATAGA GCTTTCTCAA GGGAATAATT TATATGGTGG TCCTATTGTA CATTTTTACG      2340

ATGTCTCTAT TAAGTAACCC AA                                               2362
```

(2) INFORMATION FOR SEQ ID NO: 102:

(i) SEQUENCE CHARACTERISTICS:
        (A) LENGTH: 790 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 102:

```
Met His Glu Asn Asn Thr Lys Leu Ser Ala Arg Ala Leu Pro Ser Phe
 1               5                  10                 15

Ile Asp Tyr Phe Asn Gly Ile Tyr Gly Phe Ala Thr Gly Ile Lys Asp
             20                  25                  30

Ile Met Asn Met Ile Phe Lys Thr Asp Thr Gly Gly Asn Leu Thr Leu
         35                  40                  45

Asp Glu Ile Leu Lys Asn Gln Gln Leu Leu Asn Glu Ile Ser Gly Lys
     50                  55                  60

Leu Asp Gly Val Asn Gly Ser Leu Asn Asp Leu Ile Ala Gln Gly Asn
65                   70                  75                  80

Leu Asn Thr Glu Leu Ser Lys Glu Ile Leu Lys Ile Ala Asn Glu Gln
                 85                  90                  95

Ser Gln Val Leu Asn Asp Val Asn Asn Lys Leu Asp Ala Ile Asn Thr
             100                 105                 110

Met Leu His Ile Tyr Leu Pro Lys Ile Thr Ser Met Leu Ser Asp Val
         115                 120                 125

Met Lys Gln Asn Tyr Ala Leu Ser Leu Gln Ile Glu Tyr Leu Ser Lys
     130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                 165                 170                 175

Lys Tyr Val Asn Glu Lys Phe Glu Glu Leu Thr Phe Ala Thr Glu Thr
             180                 185                 190

Thr Leu Lys Val Lys Lys Asp Xaa Ser Pro Ala Asp Ile Leu Asp Glu
         195                 200                 205

Leu Thr Glu Leu Thr Glu Leu Ala Lys Ser Val Thr Lys Asn Asp Val
     210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
             245                 250                 255

Ala Lys Glu Asn Val Lys Thr Ser Gly Ser Glu Val Gly Asn Val Tyr
         260                 265                 270

Asn Phe Leu Ile Val Leu Thr Ala Leu Gln Ala Lys Ala Phe Leu Thr
     275                 280                 285

Leu Thr Thr Cys Arg Lys Leu Leu Gly Leu Ala Asp Ile Asp Tyr Thr
         290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
             325                 330                 335

Lys Val Lys Gly Ser Asp Glu Asp Ala Lys Met Ile Val Glu Ala Lys
         340                 345                 350

Pro Gly Tyr Ala Leu Val Gly Phe Glu Met Ser Asn Asp Ser Ile Thr
     355                 360                 365

Val Leu Lys Val Tyr Glu Ala Lys Leu Lys Gln Asn Tyr Gln Val Asp
     370                 375                 380

Lys Asp Ser Leu Ser Glu Val Ile Tyr Gly Asp Thr Asp Lys Leu Leu
385                 390                 395                 400

Cys Pro Asp Gln Ser Glu Gln Ile Tyr Tyr Thr Asn Asn Ile Val Phe
             405                 410                 415
```

-continued

```
Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
            435                 440                 445

Glu Ile Asp Leu Asn Lys Lys Val Glu Ser Glu Ala Glu Tyr
            450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Gly Asn Ser Arg Leu Ile Thr Leu Thr Cys Lys Ser Tyr Leu Arg
                500                 505                 510

Lys Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
        530                 535                 540

Glu Glu Asp Asn Leu Glu Pro Trp Lys Ala Asn Asn Lys Asn Ala Tyr
545                 550                 555                 560

Val Asp His Thr Gly Gly Val Lys Gly Thr Lys Ala Leu Tyr Val His
                565                 570                 575

Lys Asp Gly Gly Ile Ser Gln Phe Ile Gly Asp Xaa Leu Lys Pro Lys
                580                 585                 590

Thr Glu Tyr Val Ile Gln Tyr Thr Val Lys Gly Lys Pro Ser Ile His
                595                 600                 605

Leu Lys Asp Glu Asn Thr Gly Tyr Ile His Tyr Glu Asp Thr Asn Asn
            610                 615                 620

Asn Leu Lys Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
                660                 665                 670

Leu Leu Ser Pro Glu Leu Ile Asn Thr Asn Asn Trp Thr Ser Thr Gly
            675                 680                 685

Ser Thr His Ile Ser Gly Asn Thr Leu Thr Leu Tyr Gln Gly Gly Arg
            690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
            755                 760                 765

Leu Ser Gln Gly Asn Asn Leu Tyr Gly Gly Pro Ile Val His Phe Tyr
770                 775                 780

Asp Val Xaa Ile Lys Pro
785                 790
```

(2) INFORMATION FOR SEQ ID NO: 103:

(i) SEQUENCE CHARACTERISTICS:
      (A) LENGTH: 2375 base pairs
      (B) TYPE: nucleic acid
      (C) STRANDEDNESS: single (D) TOPOLOGY: linear (ii) MOLECULE TYPE: DNA (genomic)

(xi) SEQUENCE DESCRIPTION: SEQ ID NO: 103:

```
ATGCACGAGA ATAATACTAA ATTAAGCGCA AGGGCCTTAC CGAGTTTTAT TGATTATTTT      60

AATGGCATTT ATGGATTTGC CACTGGTATC AAAGACATTA TGAATATGAT TTTTAAAACG     120

GATACAGGTG GTAATCTAAC CTTAGATGAA ATCCTAAAGA ATCAGCAGTT ACTAAATGAG     180

ATTTCTGGTA AATTGGATGG GGTAAATGGG AGCTTAAATG ATCTTATCGC ACAGGGAAAC     240

TTAAATACAG AATTATCTAA GGAAATCTTA AAAATTGCAA ATGAACAGAG TCAAGTTTTA     300

AATGATGTTA ATAACAAACT CGATGCGATA AATACGATGC TTCATATATA TCTACCTAAA     360

ATTACATCTA TGTTAAGTGA TGTAATGAAG CAAAATTATG CGCTAAGTCT GCAAATAGAA     420

TACTTAAGTA AACAATTGCA AGAAATTTCT GATAAATTAG ATATTATTAA CGTAAATGTT     480

CTTATTAACT CTACACTTAC TGAAATTACA CCTGCATATC AACGGATTAA ATATGTGAAT     540

GAAAAATTTG AAGAATTAAC TTTTGCTACA GAAACCACTT TAAAAGTAAA AAAGGATRAC     600

TCGCCTGCTG ATATTCTTGA TGAATTAACT GAATTAACTG AACTAGCGAA AAGTGTTACA     660

AAAAATGACG TTGATGGTTT TGAATTTTAC CTTAATACAT TCCACGATGT AATGGTAGGA     720

AATAATTTAT TCGGGCGTTC AGCTTTAAAA ACTGCTTCAG AATTAATTGC TAAAGAAAAT     780

GTGAAAACAA GTGGCAGTGA AGTAGGAAAT GTTTATAATT TCTTAATTGT ATTAACAGCT     840

CTACAAGCAA AAGCTTTTCT TACTTTAACA ACATGCCGAA AATTATTAGG CTTAGCAGAT     900

ATTGATTATA CTTCTATTAT GAATGAACAT TTAAATAAGG AAAAGAGGA ATTTAGAGTA     960

AACATCCTTC CTACACTTTC TAATACTTTT TCTAATCCTA ATTATGCAAA AGTTAAAGGA    1020

AGTGATGAAG ATGCAAAGAT GATTGTGGAA GCTAAACCAG GATATGCATT GGTTGGTTTT    1080

GAAATGAGCA ATGATTCAAT CACAGTATTA AAAGTATATG AGGCTAAGCT AAAACAAAAT    1140

TATCAAGTTG ATAAGGATTC CTTATCGGAG GTTATTTATG GTGATACGGA TAAATTATTG    1200

TGTCCAGATC AATCTGAACA AATATATATT ACAAATAACA TAGTATTTCC AAATGAATAT    1260

GTAATTACTA AAATTGATTT CACTAAAAAA ATGAAAACTT TAAGATATGA GGTAACAGCG    1320

AATTTTTATG ATTCTTCTAC AGGAGAAATT GACTTAAATA AGAAAAAAGT AGAATCAAGT    1380

GAAGCGGAGT ATAGAACGTT AAGTGCTAAT GATGATGGAG TGTATATGCC ATTAGGTGTC    1440

ATCAGTGAAA CATTTTTGAC TCCGATAAAT GGGTTTGGCC TCCAAGCTGA TGGAAATTCA    1500

AGATTAATTA CTTTAACATG TAAATCATAT TTAAGAAAAC TACTGCTAGC AACAGACTTA    1560

AGCAATAAAG AAACTAAATT GATCGTCCCG CCAAGTGGTT TTATTAGCAA TATTGTAGAG    1620

AACGGGTCCA TAGAAGAGGA CAATTTAGAG CCGTGGAAAG CAAATAATAA GAATGCGTAT    1680

GTAGATCATA CAGGCGGAGT GAAAGGAACT AAAGCTTTAT ATGTTCATAA GGACGGAGGA    1740

ATTTCACAAT TTATTGGAGA TAAKTTAAAA CCGAAAACTG AGTATGTAAT CCAATATACT    1800

GTTAAAGGAA AACCTTCTAT TCATTTAAAA GATGAAAATA CTGGATATAT TCATTATGAA    1860

GATACAAATA ATAATTTAAA AGATTATCAA ACTATTACTA AACGTTTTAC TACAGGAACT    1920

GATTTAAAGG GAGTGTATTT AATTTTAAAA AGTCAAAATG GAGATGAAGC TTGGGGAGAT    1980

AACTTTATTA TTTTGGAAAT TAGTCCTTCT GAAAAGTTAT TAAGTCCAGA ATTAATTAAT    2040

ACAAATAATT GGACGAGTAC GGGATCAACT CATATTAGCG GTAATACACT CACTCTTTAT    2100

CAGGGAGGAC GAGGAATTCT AAAACAAAAC CTTCAATTAG ATAGTTTTTC AACTTATAGA    2160

GTGTATTTTT CTGTGTCCGG AGATGCTAAT GTAAGGATTA GAAATTCTAG GGAAGTGTTA    2220
```

```
TTTGAAAAAA GATATATGAG CGGTGCTAAA GATGTTTCTG AAATGTTCAC TACAAAATTT    2280

GAGAAAGATA ACTTTTATAT AGAGCTTTCT CAAGGGAATA ATTTATATGG TGGTCCTATT    2340

GTGCATTTTT ACGATGTCYC TATTAAGTAA CCCAA                               2375

(2) INFORMATION FOR SEQ ID NO: 104:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 104:

Thr Leu His Leu Leu Lys Leu His Leu Arg Ile Lys Gly Leu Asn Met
1               5                   10                  15

Thr Lys Asn Leu Arg Asn Leu Leu Xaa Xaa Leu Xaa Gln Lys Lys
            20                  25                  30

Arg Met Ala Leu Leu Gln Ile Phe Xaa Met Ser Leu Ser Xaa Asn Arg
        35                  40                  45

Lys Val Gln Lys Met Met Trp Met Val Leu Asn Phe Thr Leu Ile His
    50                  55                      60

Ser Thr Met Xaa Glu Ile Ile Tyr Ser Gly Val Gln Leu Lys Leu Xaa
65              70                  75                      80

Arg Asn Leu Leu Lys Lys Met Lys Gln Val Ala Val Xaa Xaa Glu Met
                85                  90                  95

Phe Ile Xaa Ser Leu Tyr Gln Leu Xaa Lys Gln Lys Leu Phe Leu Leu
            100                 105                 110

Gln His Ala Glu Asn Tyr Xaa Gln Ile Leu Ile Leu Leu Leu Met
        115                 120                 125

Asn Ile Ile Arg Lys Lys Arg Asn Leu Glu Thr Ser Xaa Leu His Phe
    130                 135                 140

Leu Ile Leu Phe Leu Ile Leu Ile Met Gln Lys Leu Lys Glu Val Met
145                 150                 155                 160

Lys Met Gln Arg Leu Trp Lys Leu Asn Gln Asp Met His Trp Leu Val
                165                 170                 175

Leu Lys Ala Met Ile Gln Ser Gln Tyr Lys Tyr Met Arg Leu Ser Asn
            180                 185                 190

Lys Ile Ile Lys Leu Ile Arg Ile Pro Tyr Arg Arg Leu Phe Met Val
        195                 200                 205

Ile Arg Ile Asn Tyr Cys Val Gln Ile Asn Leu Asn Lys Tyr Ile Ile
    210                 215                 220

Gln Ile Thr Tyr Phe Gln Met Asn Met Leu Leu Lys Leu Ile Ser Leu
225                 230                 235                 240

Lys Lys Lys Leu Asp Met Arg Gln Arg Ile Phe Met Ile Leu Leu Gln
                245                 250                 255

Glu Lys Leu Thr Ile Arg Lys Lys Asn Gln Val Lys Arg Ser Ile Glu
            260                 265                 270

Arg Val Leu Met Met Met Xaa Cys Ile Cys His Val Ser Ser Val Lys
        275                 280                 285

His Phe Leu Arg Met Gly Leu Ala Ser Lys Leu Arg Gln Ile Gln Asp
    290                 295                 300

Leu Leu His Val Asn His Ile Glu Asn Tyr Cys Gln Gln Thr Ala Ile
305                 310                 315                 320
```

```
Arg Lys Leu Asn Ser Ser Arg Gln Val Phe Tyr Gln Tyr Cys Arg Glu
            325                 330                 335

Arg Val Leu Arg Arg Gly Gln Phe Arg Ala Val Glu Ser Lys Glu Cys
            340                 345                 350

Val Cys Arg Ser Tyr Arg Arg Ser Glu Trp Asn Ser Phe Ile Cys Ser
            355                 360                 365

Gly Arg Arg Asn Phe Thr Ile Tyr Trp Arg Val Lys Thr Glu Asn Val
            370                 375             380

Cys Asn Pro Ile Tyr Cys Arg Lys Thr Phe Tyr Ser Phe Lys Arg Lys
385                 390                 395                 400

Tyr Trp Ile Tyr Ser Leu Arg Tyr Lys Phe Lys Arg Leu Ser Asn Tyr
            405                 410                 415

Tyr Thr Phe Tyr Tyr Arg Asn Phe Lys Gly Ser Val Phe Asn Phe Lys
            420                 425                 430

Lys Ser Lys Trp Arg Ser Leu Gly Arg Leu Tyr Tyr Phe Gly Asn Ser
            435                 440                 445

Phe Lys Val Ile Lys Ser Arg Ile Asn Tyr Lys Leu Asp Glu Tyr Gly
            450                 455             460

Ile Asn Ser Tyr Arg Tyr Thr His Ser Leu Ser Gly Arg Thr Arg Asn
465                 470                 475                 480

Ser Lys Thr Lys Pro Ser Ile Arg Phe Phe Asn Leu Ser Val Phe Phe
            485                 490                 495

Cys Val Arg Arg Cys Cys Lys Asp Lys Phe Gly Ser Val Ile Lys Lys
            500                 505             510

Ile Tyr Glu Arg Cys Arg Cys Phe Asn Val His Tyr Lys Ile Glu Arg
            515                 520             525

Leu Leu Tyr Arg Ala Phe Ser Arg Glu Phe Ile Trp Trp Ser Tyr Cys
            530                 535             540

Thr Phe Leu Arg Cys Leu Tyr Val Thr Gln
545                 550

(2) INFORMATION FOR SEQ ID NO: 105:

(i) SEQUENCE CHARACTERISTICS:
        (A) LENGTH: 1888 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 105:

ACTCTACACT TACTGAAATT ACACCTGCGT ATCAAAGGAT TAAATATGTG AACGAAAAAT      60

TTGAGGAATT AACTTTTGCT ACRGAMACTA KTTCAAAAGT AAAAAMGGAT GGCTCTCCTS    120

CAGATATTCT KGATGAGTTA ACTGAGTTAA CWGAACTAGC GAAAAGTGTA ACAAAAAATG    180

ATGTGGATGG TTTTRAATTT TACCTTAATA CATTCCACGA TGTAAKGGTA GGAAATAATT    240

TATTCGGGCG TTCAGCTTTA AAAACTGCWT CGGAATTAAT TRCTAAAGAA AATGTGAAAA    300

CAAGTGGCAG TGARGTMGGA AATGTTTATA AYTTCTTAAT TGTATTAACA GCTCTRCAAG    360

CAAAAGCTTT TCTTACTTTA ACAACATGCC GAAAATTATT AGGSTTAGCA GATATTGATT    420

ATACTTCTAT TATGAATGAA CATTTAAATA AGGAAAAAGA GGAATTTAGA GTAAACATCC    480

TYCCTACACT TTCTAATACT TTTTCTAATC CTAATTATGC AAAAGTTAAA GGAAGTGATG    540

AAGATGCAAA GATGATTGTG GAAGCTAAAC CAGGATATGC ATTGGTTGGT TTTGAAATGA    600
```

-continued

```
GCAATGATTC AATCACAGTA TTAAAAGTAT ATGAGGCTAA GCTAAAACAA AATTATCAAG    660

TTGATAAGGA TTCCTTATCG GAGGTTATTT ATGGTGATAC GGATAAATTA TTGTGTCCAG    720

ATCAATCTGA ACAAATATAT TATACAAATA ACATAGTATT TCCAAATGAA TATGTAATTA    780

CTAAAATTGA TTTCACTAAA AAAATGAAAA CTTTAAGATA TGAGGTAACA GCGAATTTTT    840

ATGATTCTTC TACAGGAGAA ATTGACTTAA ATAAGAAAAA AGTAGAATCA AGTGAAGCGG    900

AGTATAGAAC GTTAAGTGCT AATGATGATG GRGTGTATAT GCCATTAGGT GTCATCAGTG    960

AAACATTTTT GACTCCGATA AATGGGTTTG GCCTCCAAGC TGAGGCAAAT TCAAGATTAA   1020

TTACTTTAAC ATGTAAATCA TATTTAAGAG AACTACTGCT AGCAACAGAC TTAAGCAATW   1080

AGGAAACTAA ATTGATCTTC CCGCCAAGTG TTTTATTAGC AATATTGTAG AGAACGGGTC   1140

CTTAGAAGAG GACAATTTAG AGCCGTGGAA AGCAAATAAT AAGAATGCGT ATGTAGATCA   1200

TACAGGCGGA GTGAATGGAA CTAAAGCTTT ATATGTTCAT AAGGACGGAG GAATTTCACA   1260

ATTTATTGGA GATAAGTTAA AACCGAAAAC TGAGTATGTA ATCCAATATA CTGTTAAAGG   1320

AAAACCTTCT ATTCATTTAA AAGATGAAAA TACTGGATAT ATTCATTATG AAGATACAAA   1380

TAATAATTTA AAAGATTATC AAACTATTAC TAAACGTTTT ACTACAGGAA CTGATTTAAA   1440

GGGAGTGTAT TTAATTTTAA AAAGTCAAAA TGGAGATGAA GCTTGGGGAG ATAACTTTAT   1500

TATTTTGGAA ATTAGTCCTT CTGAAAAGTT ATTAAGTCCA GAATTAATTA ATACAAATAA   1560

TTGGACGAGT ACGGGATCAA CTCATATTAG CGGTAATACA CTCACTCTTT ATCAGGGAGG   1620

ACGAGGAATT CTAAAACAAA ACCTTCAATT AGATAGTTTT TCAACTTATA GAGTGTATTT   1680

TTCTGTGTCC GGAGATGCTA ATGTAAGGAT TAGAAATTCT AGGGAAGTGT TATTTGAAAA   1740

AAGATATATG AGCGGTGCTA AAGATGTTTC TGAAATGTTC ACTACAAAAT TTGAGAAAGA   1800

TAACTTTTAT ATAGAGCTTT CTCAAGGGAA TAATTTATAT GGTGGTCCTA TTGTACATTT   1860

TTACGATGTC TCTATTAAGT AACCCAAA                                     1888
```